United States Patent
Alet et al.

(10) Patent No.: US 9,150,544 B2
(45) Date of Patent: Oct. 6, 2015

(54) SULPHONYLAMINOPYRROLIDINONE DERIVATIVES, THEIR PREPARATION AND THEIR THERAPEUTIC APPLICATION

(71) Applicant: Sanofi, Paris (FR)

(72) Inventors: Nathalie Alet, Paris (FR); Jean-Michel Altenburger, Paris (FR); Jean-Pascal Herault, Paris (FR); Reinhard Kirsch, Paris (FR); Gilbert Lassalle, Paris (FR); Sergio Mallart, Paris (FR); Marie-Claire Philippo-Orts, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/366,402

(22) PCT Filed: Dec. 19, 2012

(86) PCT No.: PCT/EP2012/076224
§ 371 (c)(1),
(2) Date: Jun. 18, 2014

(87) PCT Pub. No.: WO2013/092756
PCT Pub. Date: Jun. 27, 2013

(65) Prior Publication Data
US 2014/0329801 A1    Nov. 6, 2014

(30) Foreign Application Priority Data

Dec. 21, 2011 (EP) .................................. 11306733

(51) Int. Cl.
| C07D 401/14 | (2006.01) |
| C07D 417/14 | (2006.01) |
| A61K 31/4709 | (2006.01) |

(52) U.S. Cl.
CPC ............ *C07D 401/14* (2013.01); *C07D 417/14* (2013.01)

(58) Field of Classification Search
None
See application file for complete search history.

(56) References Cited

U.S. PATENT DOCUMENTS

| 6,432,955 | B1 | 8/2002 | van Boeckel |
| 6,602,864 | B1 | 8/2003 | Choi-Sledeski |

FOREIGN PATENT DOCUMENTS

| WO | 98/25611 | 6/1998 |
| WO | 01/39759 | 6/2001 |

OTHER PUBLICATIONS

Gerbrand van Dieijen, Guido Tans, Jan Rosing, and H. Coenraad Hemker "The Role of Phospholipid and Factor VIII, in the Activation of Bovine Factor X" The Journal of Biological Chemistry, vol. 256, No. 7, pp. 333-3442, 1981 (Apr. 10, 1981).
A. Tuinenburg, E . P . Mauser-Bunschoten, M. C. Verhaar, D. H. Biesma and R. E . G. Schutgens "Cardiovascular disease in patients with hemophilia" Journal of Thrombosis and Haemostasis, 7: 247-254 (Oct. 20, 2008).
A. Weltermann, S . Eichinger, C. Bialonczyk, E . Minar, M. Hirschl, P. Quehenberger, V. Schonauer and P. A. Kyrle "The risk of recurrent venous thromboembolism among patients with high factor IX levels" Journal of Thrombosis and Haemostasis, 1: 28-32 (Jan. 3, 2003).
John W. Eikelboom, Steven L. Zelenkofske, and Christopher P. Rusconi "Coagulation Factor IXa as a Target for Treatment and Prophylaxis of Venous Thromboembolism" Arterioscler. Thromb. Vasc. Biol. 2010, 30, 382-387 (Feb. 5, 2010).
H. Coenraad Hemker, Peter Giesen, Raed Al Dieri, Véronique Regnault, Eric de Smedt, Rob Wagenvoord, Thomas Lecompte, Suzette Béguin "Calibrated Automated Thrombin Generation Measurement in Clotting Plasma" Pathophysiol. Haemost. Thromb. 2003, 33, 4-15 (Jun. 2003).
A. Šrámek, M. Kriek, F.R. Rosendaal "Decreased mortality of ischaemic heart disease among carriers of haemophilia" Lancet. 2003; 362: 351-354 (Aug. 2003).
Giora Z. Feuerstein, John R. Toomey, Richard Valocik, Paul Koster, Arun Patel, Michael N. Blackburn "An Inhibitory Anti-factor IX Antibody Effectively Reduces Thrombus Formation in a Rat Model of Venous Thrombosis" Thromb. Haemost. 1999 82 5: 1446-1450 (Nov. 1999).
Jerry W. Skiles, Ronald Sorcek, Stephen Jacober, Clara Miao, Philip W. Mui, Daniel McNeil, Alan S. Rosenthal "elastase inhibitors containing conformationally restricted lactams as P3-P2 dipeptide replacements" Bioorganic & Medicinal Chemistry Letters vol. 3, Issue 4, pp. 773-778 (Apr. 1993).
Franchini, et al., "A New era for anticoagulants," European Journal of Internal Medicine, vol. 20, No. 6, Oct. 1, 2009, pp. 562-568.
International Search Report from PCT published application WO2013/092756 published Jun. 27, 2013.

*Primary Examiner* — Zinna Northington Davis
(74) *Attorney, Agent, or Firm* — McDonnell Boehnen Hulbert & Berghoff

(57) ABSTRACT

The invention relates to new sulphonylaminopyrrolidinone compounds having antithrombotic activity which, in particular, inhibit blood clotting factor IXa and/or factor Xa, to processes for their preparation and to use thereof as drugs.

23 Claims, No Drawings

SULPHONYLAMINOPYRROLIDINONE DERIVATIVES, THEIR PREPARATION AND THEIR THERAPEUTIC APPLICATION

This application is a national stage application under 35 U.S.C. §371 of International Application No. PCT/EP2012/076224, filed December 19, 2012, the disclosure of which is explicitly incorporated by reference herein.

FIELD OF THE INVENTION

The invention relates to new sulphonylaminopyrrolidinone compounds having antithrombotic activity which, in particular, inhibit blood clotting factor IXa and/or factor Xa, to processes for their preparation and to use thereof as drugs.

BACKGROUND OF THE INVENTION

Blood clotting is a process of control of the blood stream essential for the survival of mammals. The process of clotting and the subsequent dissolution of the clot after wound healing has taken place, after vascular damage and can be divided into four phases:

1. The phase of the initiation of the coagulation cascade either after vessels injury or vasoconstriction leads to low amount of thrombin generation;
2. The next phase is the amplification phase where platelets are activated by thrombin. The platelets attach to the site of the vessel wall damage and form a platelet aggregate which is crosslinked by fibrinogen (fibrin). At the meantime, the complexes of clotting factors (tenase and prothrombinase) can form of the surface of activated platelets. The platelets accelerate blood clotting by means of this mechanism;
3. The formation of the thrombus is stabilized by the fibrin network which is formed consecutive to the cleavage of fibrinogen by the large amount of thrombin;
4. After wound healing, the thrombus is dissolved by the action of the key enzyme of the endogenous fibrinolysis system, plasmin.

In a more detailed scenario, the initiation phase can be driven by two alternative pathways: the intrinsic and the extrinsic pathway. These pathways are initiated by different mechanisms, but in the later phase they converge to give a common final path of the clotting cascade starting with the activation of clotting factor X. The activated factor X is responsible for the formation of thrombin from the inactive precursor prothrombin circulating in the blood. The formation of a thrombus on the bottom of a vessel wall abnormality without a wound is commonly described as the result of the intrinsic pathway. Whereas, fibrin clots formation as a response to tissue damage or an injury is the result of the extrinsic pathway. Both pathways comprise a relatively large number of proteins, which are known as clotting factors.

The "extrinsic" pathway is so called because an exogenous agent (i.e., TF) is required for activation of the clotting factors in plasma. The TF:FVIIa complex is the key initiator of the coagulation protease cascade and activates both FIX to FIXa and FX to FXa.

Alternatively, the "intrinsic" pathway is initiated when prekallikrein, high molecular weight kininogen, factor XI and XII bind to a negatively charged surface: it is the contact phase. The result of these processes is the activation of prekallikrein, factor XII, and finally factor XI that leads, in the presence of $Ca^{2+}$ ions, to the activation of factor IX.

Whatever the initiating pathway, the generation of factor IXa and factor Xa leads to the formation of low amounts of thrombin, which are able to activate the platelets through the cleavage of protease activated receptors and finally the cofactors factor V and factor VIII: it is the start of the amplification phase. Platelet activation plays a major role in the coagulation since it allows the formation of the two complexes which support the amplification phase: the tenase and the prothrombinase complexes. The tenase complex (FVIIIa:FIXa) plays a key role in amplifying the clotting cascade by activating factor X to factor Xa. The prothrombinase complex (FVa:FXa) activates prothrombin to thrombin, which is the central protease of the clotting cascade. Thrombin cleaves fibrinogen into unsoluble fibrin monomers that polymerize. Thrombin also activates the transglutaminase FXIII to FXIIIa that in turn cross-links soluble fibrin monomers into a fibrin matrix that leads to clot stabilization. Finally, the coagulation cascade is regulated by several natural anticoagulants (TFPI, Antithrombin, HCII, Prot C, Prot S . . . ).

Both clotting factor IX and factor X can be activated by means of the intrinsic pathway and the extrinsic pathway. Their activation are thus a central point of intersection between the two pathways of blood clotting. Moreover the activity of factor IXa is intimately linked to the presence of platelet since, after activation, platelets promote tenase complex formation that increases factor IXa activity by a fold of 200 000 (van Dieijen et al, J. Biol. Chem. 1981; 256: 3433-3442), giving it a central role in the rate limiting step of thrombin generation. Given its central role and its interdependency to platelets, we do know that factor IXa has an important role in both venous and arterial thrombosis.

Evidence is given by the fact that defects in factor IXa lead to hemophilia B. More precisely, the clinical phenotype of hemophilia B depends on the plasma FIX level. Thus, spontaneous bleeding occurs in patients with severe hemophilia (<1% FIX activity). Whereas mild FIX deficiency may not require prophylaxis to prevent bleeding during minor procedures, but interestingly, in epidemiological studies it has been associated with fewer cardiovascular events (Šrámek A et al, Lancet. 2003; 362: 351-354; Tuinenburg A el al, J Thromb Haemost. 2009; 7: 247-254). In mirror, increased concentrations of factor IXa in the blood lead to a significantly increased risk of thrombosis formation (Weltermann A, et al., J Thromb Haemost. 2003; 1: 28-32). And finally the regulation of factor IXa activity can reduce thrombus formation in animal models (Feuerstein G Z, et al., Thromb Haemost. 1999; 82: 1443-1445).

In conclusion, as described by Eikelboom in his recent review (Arterioscler Thromb Vasc Biol. 2010; 30: 382-7), "the narrow window for clinically important bleeding with a wider window for reduced cardiovascular events in hemophilia B carriers lends further support for FIXa as an attractive target for anticoagulant therapy."

Numerous documents describe compounds with antithrombotic activity.

For instance, the U.S. Pat. No. 6,432,955 B1 is directed to anti-thrombotic compounds all comprising the following core:

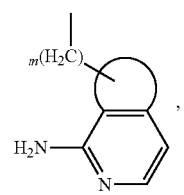

which may be linked to a variety of side-chains.

Another example is the U.S. Pat. No. 6,602,864 B1 describing factor Xa inhibitors of formula:

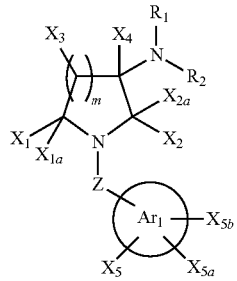

where Z is an alkylenyl group.

The compounds of the formula I according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

The invention therefore relates to a compound corresponding to the formula (I):

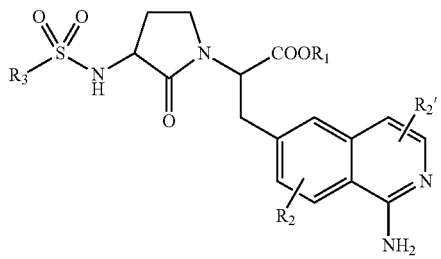

(I)

in which:

$R_1$ represents a hydrogen atom, a $(C_1-C_6)$alkyl group, a $(C_3-C_7)$cycloalkyl group, a $(C_3-C_7)$cycloalkyl-$(C_1-C_6)$alkyl- group, a Rb—O—Ra— group where Rb represents a $(C_1-C_6)$alkyl group or a $(C_3-C_7)$cycloalkyl group and Ra represents a $(C_1-C_6)$alkyl group, or a Rd-O—C(O)—O-Rc- group where Rd represents a $(C_1-C_6)$alkyl group or a $(C_3-C_7)$cycloalkyl group and Rc represents a $(C_1-C_6)$alkyl group, or a Rf—C(O)—O—Re— group where Re represents a $(C_1-C_6)$alkyl group and Rf represents a $(C_1-C_6)$alkyl group, $R_2$ represents a halogen atom, —OH, —CN, or a $(C_1-C_6)$ alkyl group, or an —O—$(C_1-C_6)$alkyl group, said alkyl groups being non-substituted or substituted by one or more halogen atoms, identical to or different from one another, or a Rg-O—Rh—O— group where Rg represents a $(C_1-C_6)$alkyl group and Rh represents a $(C_1-C_6)$ alkyl group, $R_2'$ represents a hydrogen atom or a $(C_1-C_6)$alkyl group, $R_3$ represents:

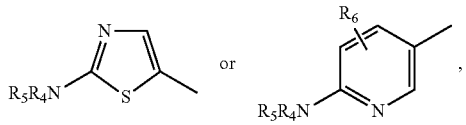

$R_4$ and $R_5$ represent, independently of one another, a $(C_1-C_6)$ alkyl group or a $(C_3-C_7)$cycloalkyl group, or $R_4$ and $R_5$ together form, with the nitrogen atom to which they are attached, a 3 to 7 membered heterocycloalkyl group comprising from 1 to 2 heteroatoms chosen from nitrogen, oxygen and sulphur, said heterocycloalkyl group being non-substituted or substituted by one or more groups, identical or different from one another, chosen from halogen atom and $(C_1-C_6)$alkyl group, $(C_1-C_6)$alkoxy group, —$CF_3$, —$OCF_3$, $R_6$ represents a halogen atom, a hydrogen atom, a $(C_1-C_6)$ alkyl group, a $(C_1-C_6)$alkoxy group or —CN.

The compounds of formula (I) comprise at least two asymmetric carbon atoms, identified by the asterisks (*1 and *2) in the formula below. They can thus exist in the form of enantiomers or diastereoisomers. These enantiomers, diastereoisomers, and their mixtures, including racemic mixtures, come within the invention.

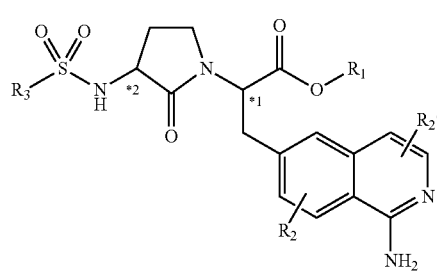

(I)

The asymmetric carbon identified by the asterisk *1 in the above formula advantageously exhibits the (R) configuration. The asymmetric carbon identified by the asterisk *2 in the above formula advantageously exhibits the (S) configuration.

The compounds of formula (I) can exist in the form of bases or of addition salts with acids or bases. Such addition salts come within the invention.

These salts are advantageously prepared with pharmaceutically acceptable acids or bases but the salts of other acids or bases, for example of use in the purification or isolation of the compounds of formula (I), also come within the invention.

In the context of the present invention:

a halogen atom is understood to mean a fluorine, chlorine, a bromine or an iodine;

a $(C_1-C_6)$alkyl group is understood to mean a saturated aliphatic group which comprises from 1 to 6 carbon atoms (advantageously from 1 to 4 carbon atoms) and which is linear or branched. Mention may be made, by way of examples, of the methyl, ethyl, propyl, isopropyl, butyl, isobutyl, tert-butyl, pentyl, hexyl and the like;

a $(C_3-C_7)$cycloalkyl group is understood to mean a cyclic alkyl group comprising between 3 and 7 carbon atoms, all the carbon atoms being involved in the cyclic structure. Mention may be made, by way of examples, of the cyclopropyl, cyclobutyl, cyclopentyl or cyclohexyl groups, and the like;

a heterocycloalkyl group is understood to mean a cycloalkyl group as defined above additionally comprising from 1 to 2 heteroatoms chosen from nitrogen, oxygen and sulphur. Mention may be made, by way of examples, of the azetidinyl, pyrrolidinyl, piperidinyl, morpholinyl and piperazinyl groups. This heterocycloalkyl group can be substituted, in any position, by one or more (for example by 1 to 3) groups, identical to or different from one another, chosen from halogen atoms and alkyl groups, alcoxy groups, —CF$_3$, —OCF$_3$;

a cycloalkyl-alkyl group is understood to mean a cyclic alkyl group as defined above and linked to an alkyl group as defined above. Mention may be made, by way of examples, of the cyclopropyl-methyl group, cyclopropyl-ethyl group and cyclobutyl-methyl group;

an alkoxy group is understood to mean an —O-alkyl radical where the alkyl group is as defined above;

an alkoxyalkyl group is understood to mean a radical of formula alkyl-O-alkyl, where the alkyl groups, which are identical to or different from one another, are as defined above.

According to the present invention, the following stand out:

the compounds of Formula (IA) in which in formula $R_3$ represents:

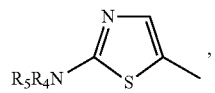

or the compounds of Formula (IB) in which $R_3$ represents:

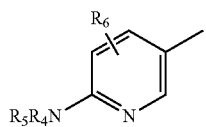

and/or the compounds of formula (I), (IA) or (IB) in which $R_2$ represents a —OCF$_3$ group, the other substituents being as defined for the compounds of Formula (I).

In the formula (I), (IA), (IB), the following in particular stand out, or any of their combination:

$R_1$ represents a hydrogen atom, a (C$_1$-C$_6$)alkyl group, a (C$_3$-C$_7$)cycloalkyl group, a (C$_3$-C$_7$)cycloalkyl-(C$_1$-C$_6$)alkyl group, a Rb—O—Ra— group where Rb represents a (C$_1$-C$_6$)alkyl group and Ra represents a (C$_1$-C$_6$)alkyl group, or a Rd-O—C(O)—O-Rc- where Rd represents a (C$_1$-C$_6$)alkyl group or a (C$_3$-C$_7$)cycloalkyl group and Rc represents a (C$_1$-C$_6$)alkyl group, or a Rf—C(O)—O—Re— where Re represents a (C$_1$-C$_6$)alkyl group and Rf represents a (C$_1$-C$_6$)alkyl group, and/or $R_2$ represents an halogen atom, —OH, —CN, or a (C$_1$-C$_6$) alkyl group, or a —O—(C$_1$-C$_6$)alkyl group, said alkyl groups being non-substituted or substituted by one or more halogen atom, identical to or different from one another, or a Rg-O—Rh—O— group where Rg represents a (C$_1$-C$_6$)alkyl group and Rh represents a (C$_1$-C$_6$)alkyl group, and/or $R_2$' represents a hydrogen atom or a (C$_1$-C$_6$)alkyl group, and/or $R_3$ represents:

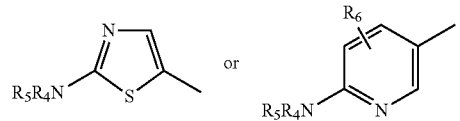

and/or $R_4$ and $R_5$ represent, independently of one another, a (C$_1$-C$_6$) alkyl group or a (C$_3$-C$_7$)cycloalkyl group, and/or or $R_4$ and $R_5$ together form, with the nitrogen atom to which they are attached, a 3 to 7 membered N-heterocycloalkyl group comprising from 1 to 2 heteroatoms chosen from nitrogen, oxygen and sulphur, said heterocycloalkyl group being non-substituted or substituted by one or more halogen atoms, and/or $R_6$ represents a halogen atom, a hydrogen atom, a (C$_1$-C$_6$) alkyl group.

According to the present invention, preference is given to the compounds of formula (I) in which:

$R_1$ represents a hydrogen atom, a methyl, an ethyl, a propyl, an isopropyl, a butyl, an isobutyl, a cyclopentyl, a cyclopropylmethyl, a cyclobutylmethyl, a 2-methoxyethyl, a cyclohexyloxycarbonyloxymethyl, a 1-cyclohexyloxycarbonyl oxymethyl, a 2,2-dimethylpropionyloxymethyl, $R_2$ represents a chlorine atom, a fluorine atom, —OH, —CN, a methyl, an ethyl, a methoxy, an ethoxy, —CF$_3$, —OCF$_3$, a 2-methoxyethoxy, $R_2$' represents a hydrogen atom, a methyl, $R_3$ represents:

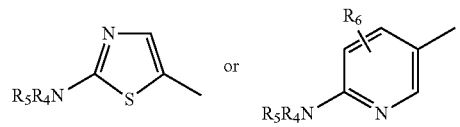

$R_4$ and $R_5$ represent, independently of one another, a methyl or a cyclobutyl, or $R_4$ and $R_5$ together form, with the nitrogen atom to which they are attached, a heterocycloalkyl group chosen from azetidin-1-yl or pyrrolidin-1-yl, said heterocycloalkyl group being non-substituted or substituted by one or two fluorine atoms, $R_6$ represents a hydrogen atom, a chlorine atom, a methyl.

According to the present invention, preference is particularly given to the compounds of formula (I) in which:

$R_1$ represents a hydrogen atom or a methyl,
$R_2$ represents a chlorine atom, —CF$_3$, —OCF$_3$,
$R_2$' represents a hydrogen atom,
$R_3$ represents:

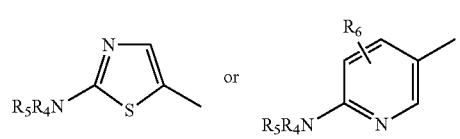

R₄ and R₅ represent, independently of one another, a methyl, or R₄ and R₅ together form, with the nitrogen atom to which they are attached, a heterocycloalkyl group chosen from azetidin-1-yl or pyrrolidin-1-yl, said heterocycloalkyl group being non-substituted or substituted by one or two fluorine atoms, R₆ represents a hydrogen atom.

Among the compounds according to the invention, mention may in particular be made of the compounds hereinafter:

TABLE I

| | IUPAC Name generated from AutoNom ® (MDL, Elsevier) | Chemical Structure | IC 50 (μM) IXa | IC50 (μM) Xa |
|---|---|---|---|---|
| 1 | (R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid | 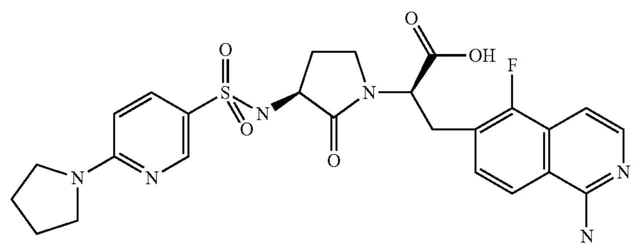 [SMILES: Nc1nccc2c(F)c(C[C@H](C(=O)O)N3CC[C@H](NS(=O)(=O)c4ccc(N5CCCC5)nc4)C3=O)ccc12] | 0.1 | 4.68 |
| 2 | (R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid methyl ester | 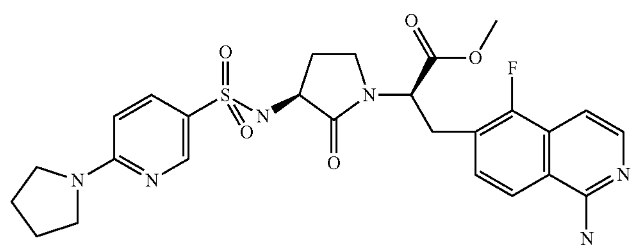 [SMILES: COC(=O)[C@@H](Cc1ccc2c(N)nccc2c1F)N1CC[C@H](NS(=O)(=O)c2ccc(N3CCCC3)nc2)C1=O] | >5 | >5 |
| 3 | (R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid ethyl ester | 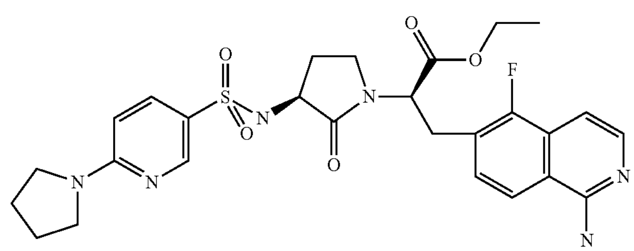 [SMILES: CCOC(=O)[C@@H](Cc1ccc2c(N)nccc2c1F)N1CC[C@H](NS(=O)(=O)c2ccc(N3CCCC3)nc2)C1=O] | >5 | ND |
| 4 | (R)-3-(1-Amino-5-fluoro-isoquinolin-6-yl)-2-[(S)-3-(6-dimethylamino-pyridine-3-sulfonylamino)-2-oxo-pyrrolidin-1-yl]-propionic acid | 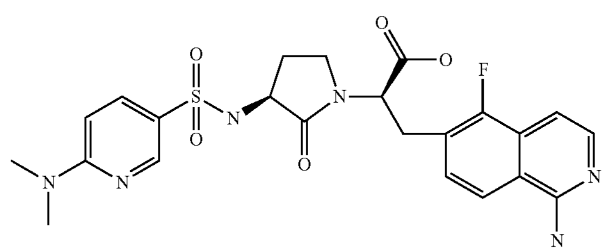 [SMILES: CN(C)c1ccc(S(=O)(=O)N[C@H]2CCN([C@H](Cc3ccc4c(N)nccc4c3F)C(=O)O)C2=O)cn1] | 0.17 | ND |
| 5 | (R)-3-(1-Amino-5-fluoro-isoquinolin-6-yl)-2-[(S)-3-(6-dimethylamino-pyridine-3-sulfonylamino)-2-oxo-pyrrolidin-1-yl]-propionic acid methyl ester | 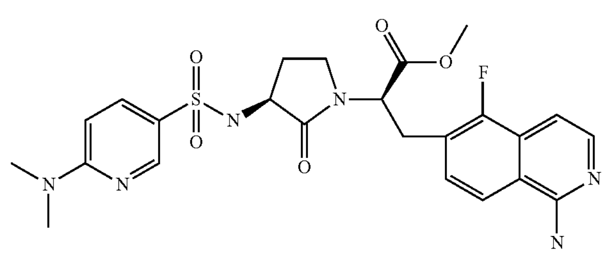 [SMILES: COC(=O)[C@@H](Cc1ccc2c(N)nccc2c1F)N1CC[C@H](NS(=O)(=O)c2ccc(N(C)C)nc2)C1=O] | ND | ND |

TABLE I-continued

| | IUPAC Name generated from AutoNom ® (MDL, Elsevier) | Chemical Structure | IC 50 (µM) IXa | IC50 (µM) Xa |
|---|---|---|---|---|
| 6 | (R)-3-(1-Amino-5-fluoro-isoquinolin-6-yl)-2-[(S)-3-(2-dimethylamino-thiazole-5-sulfonylamino)-2-oxo-pyrrolidin-1-yl]-propionic acid | 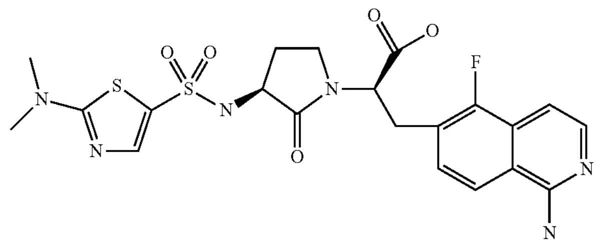 [SMILES: CN(C)c1ncc(S(=O)(=O)N[C@H]2CCN([C@H](Cc3ccc4c(N)nccc4c3F)C(=O)O)C2=O)s1] | 0.16 | 0.20 |
| 7 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid | 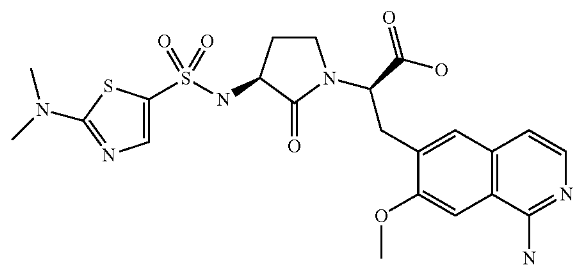 [SMILES: COc1cc2c(N)nccc2cc1C[C@H](C(=O)O)N1CC[C@H](NS(=O)(=O)c2cnc(N(C)C)s2)C1=O] | 0.11 | 2 |
| 8 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid isobutyl ester | 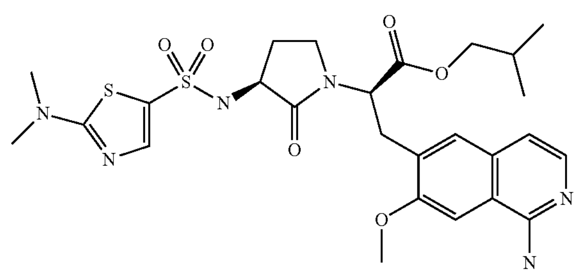 [SMILES: COc1cc2c(N)nccc2cc1C[C@H](C(=O)OCC(C)C)N1CC[C@H](NS(=O)(=O)c2cnc(N(C)C)s2)C1=O] | 1.60 | 0.10 |
| 9 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid cyclopropylmethyl ester | 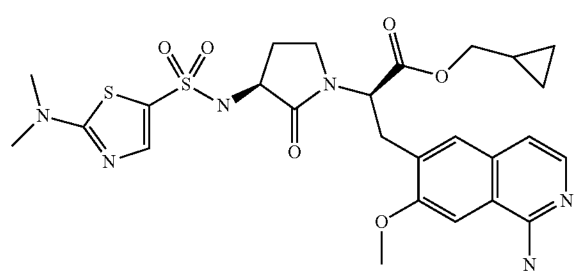 [SMILES: COc1cc2c(N)nccc2cc1C[C@H](C(=O)OCC1CC1)N1CC[C@H](NS(=O)(=O)c2cnc(N(C)C)s2)C1=O] | 0.76 | 0.029 |
| 10 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid cyclobutylmethyl ester | 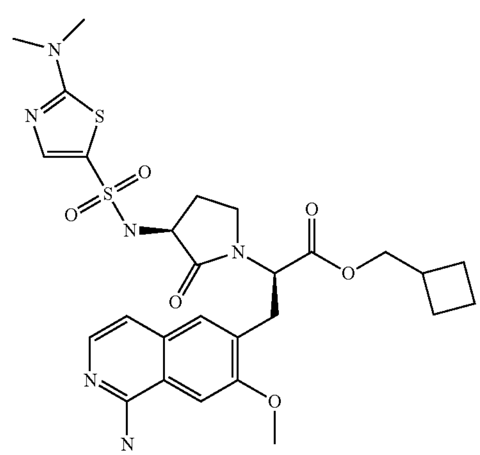 [SMILES: COc1cc2c(N)nccc2cc1C[C@H](C(=O)OCC1CCC1)N1CC[C@H](NS(=O)(=O)c2cnc(N(C)C)s2)C1=O] | 1.30 | 0.086 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 11 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid isopropyl ester | 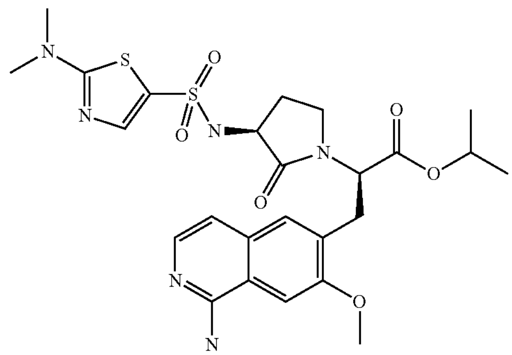 [SMILES: COc1cc2c(N)nccc2cc1C[C@H](C(=O)OC(C)C)N1CC[C@H](NS(=O)(=O)c2cnc(N(C)C)s2)C1=O] | 1.60 | 0.021 |
| 12 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid cyclopentyl ester | 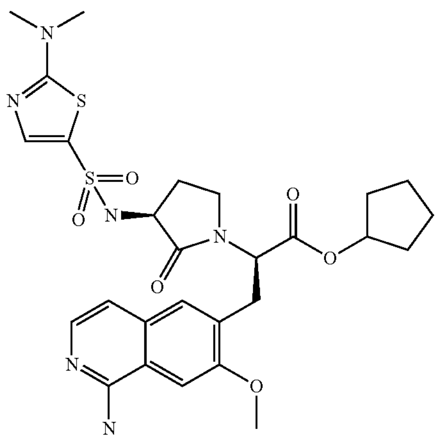 [SMILES: COc1cc2c(N)nccc2cc1C[C@H](C(=O)OC1CCCC1)N1CC[C@H](NS(=O)(=O)c2cnc(N(C)C)s2)C1=O] | 1.50 | 0.043 |
| 13 | (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid ethyl ester | 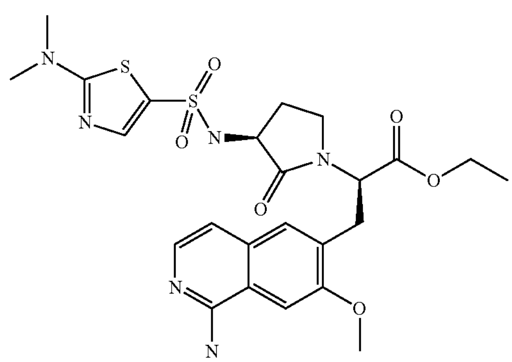 [SMILES: CCOC(=O)[C@@H](Cc1cc2ccnc(N)c2cc1OC)N1CC[C@H](NS(=O)(=O)c2cnc(N(C)C)s2)C1=O] | 1.60 | 0.021 |
| 14 | (R)-3-(1-Amino-7-methoxy-isoquinolin-6-yl)-2-[(S)-2-oxo-3-(2-pyrrolidin-1-yl-thiazole-5-sulfonylamino)-pyrrolidin-1-yl]-propionic acid | 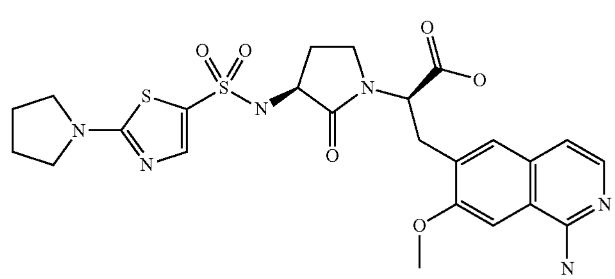 [SMILES: COc1cc2c(N)nccc2cc1C[C@H](C(=O)O)N1CC[C@H](NS(=O)(=O)c2cnc(N3CCCC3)s2)C1=O] | 0.11 | 0.004 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 15 | (R)-3-(1-Amino-7-methoxy-isoquinolin-6-yl)-2-[(S)-2-oxo-3-(2-pyrrolidin-1-yl-thiazole-5-sulfonylamino)-pyrrolidin-1-yl]-propionic acid cyclopropylmethyl ester | 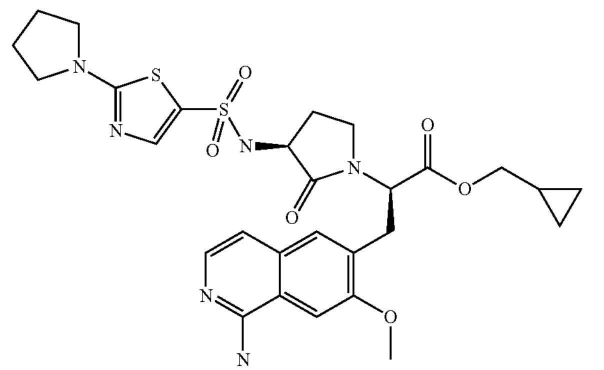 [SMILES: COc1cc2c(N)nccc2cc1C[C@H](C(=O)OCC1CC1)N1CC[C@H](NS(=O)(=O)c2cnc(N3CCCC3)s2)C1=O] | 0.78 | 0.12 |
| 16 | (R)-3-(1-Amino-7-methoxy-isoquinolin-6-yl)-2-[(S)-2-oxo-3-(2-pyrrolidin-1-yl-thiazole-5-sulfonylamino)-pyrrolidin-1-yl]-propionic acid ethyl ester | 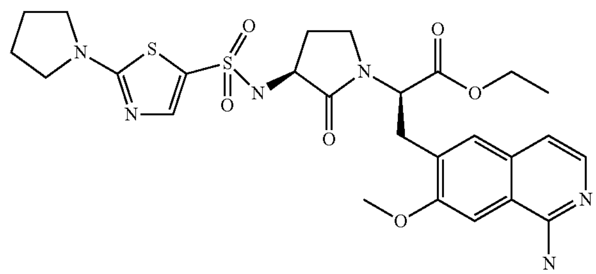 [SMILES: CCOC(=O)[C@@H](Cc1cc2ccnc(N)c2cc1OC)N1CC[C@H](NS(=O)(=O)c2cnc(N3CCCC3)s2)C1=O] | 1.30 | 0.074 |
| 17 | (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid | 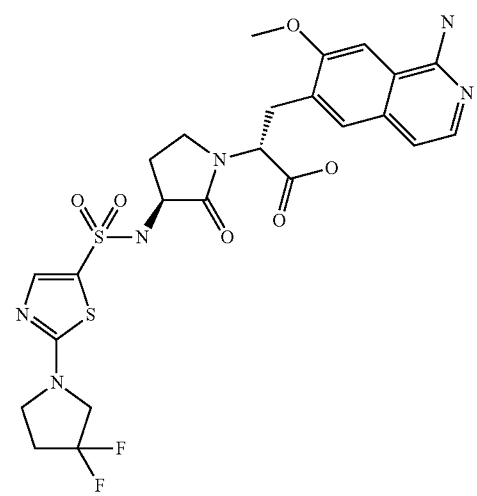 [SMILES: COc1cc2c(N)nccc2cc1C[C@H](C(=O)O)N1CC[C@H](NS(=O)(=O)c2cnc(N3CCC(F)(F)C3)s2)C1=O] | 0.070 | 0.017 |
| 18 | (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid ethyl ester | 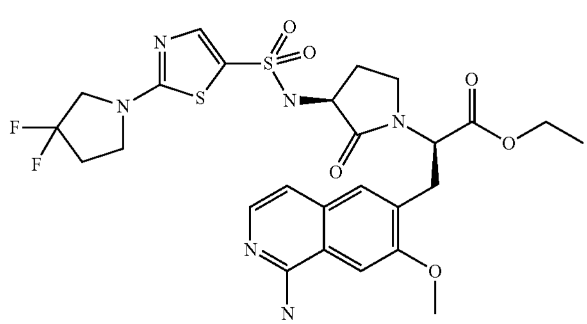 [SMILES: CCOC(=O)[C@@H](Cc1cc2ccnc(N)c2cc1OC)N1CC[C@H](NS(=O)(=O)c2cnc(N3CCC(F)(F)C3)s2)C1=O] | 2.50 | 0.12 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 19 | (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid cyclopropylmethyl ester | 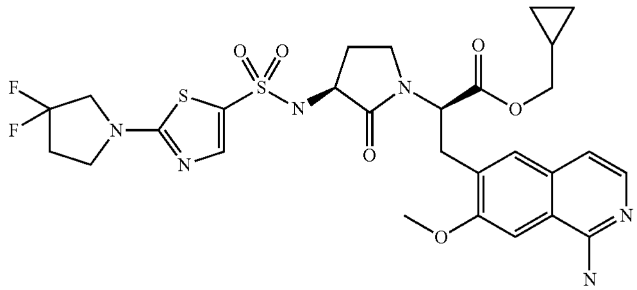 [SMILES: COc1cc2c(N)nccc2cc1C[C@H](C(=O)OCC1CC1)N1CC[C@H](NS(=O)(=O)c2cnc(N3CCC(F)(F)C3)s2)C1=O] | 1.10 | 1 |
| 20 | (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid isopropyl ester | 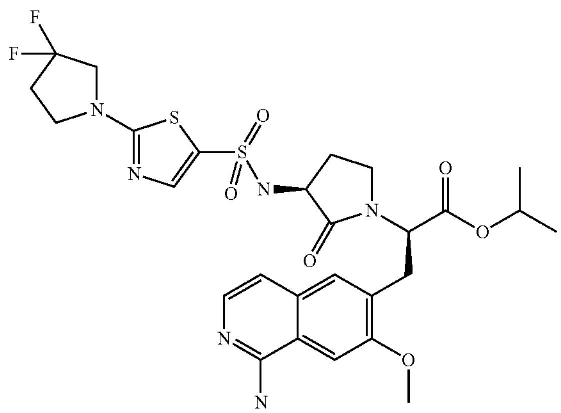 [SMILES: COc1cc2c(N)nccc2cc1C[C@H](C(=O)OC(C)C)N1CC[C@H](NS(=O)(=O)c2cnc(N3CCC(F)(F)C3)s2)C1=O] | 1.50 | 0.63 |
| 21 | (R)-3-(1-Amino-7-methoxy-isoquinolin-6-yl)-2-{(S)-3-[2-((R)-3-fluoro-pyrrolidin-1-yl)-thiazole-5-sulfonylamino]-2-oxo-pyrrolidin-1-yl}-propionic acid | 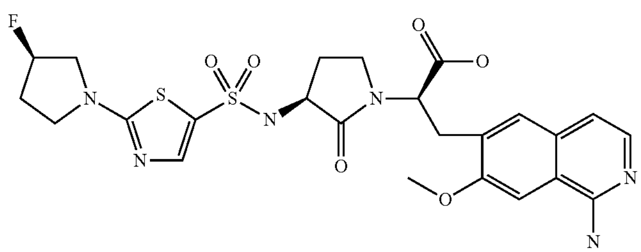 [SMILES: COc1cc2c(N)nccc2cc1C[C@H](C(=O)O)N1CC[C@H](NS(=O)(=O)c2cnc(N3CC[C@@H](F)C3)s2)C1=O] | 0.14 | 0.008 |
| 22 | (R)-3-(1-Amino-7-methoxy-isoquinolin-6-yl)-2-[(S)-3-(6-dimethylamino-5-methyl-pyridine-3-sulfonylamino)-2-oxo-pyrrolidin-1-yl]-propionic acid | 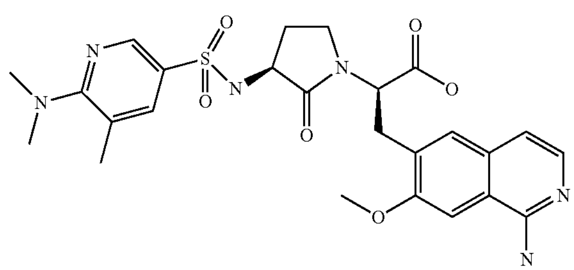 [SMILES: COc1cc2c(N)nccc2cc1C[C@H](C(=O)O)N1CC[C@H](NS(=O)(=O)c2cnc(N(C)C)c(C)c2)C1=O] | 0.15 | 0.073 |
| 23 | (R)-3-(1-Amino-7-methoxy-isoquinolin-6-yl)-2-[(S)-3-(6-dimethylamino-5-methyl-pyridine-3-sulfonylamino)-2-oxo-pyrrolidin-1-yl]-propionic acid ethyl ester | 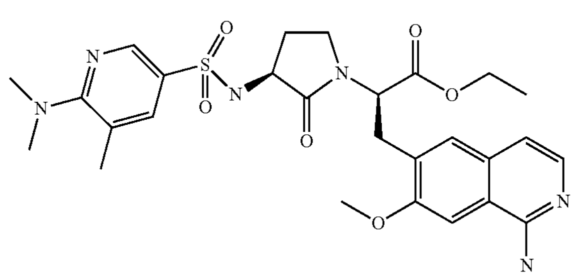 [SMILES: CCOC(=O)[C@@H](Cc1cc2ccnc(N)c2cc1OC)N1CC[C@H](NS(=O)(=O)c2cnc(N(C)C)c(C)c2)C1=O] | >5 | 1.60 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 24 | (R)-3-(1-Amino-7-methoxy-isoquinolin-6-yl)-2-[(S)-3-(6-dimethylamino-pyridine-3-sulfonylamino)-2-oxo-pyrrolidin-1-yl]-propionic acid | 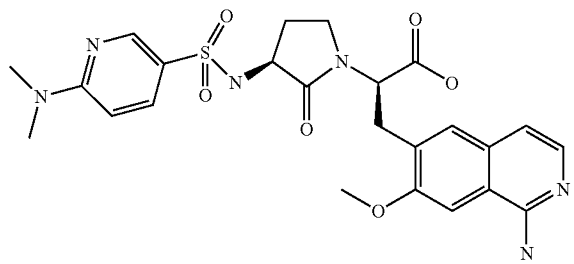 [SMILES: COc1cc2c(N)nccc2cc1C[C@H](C(=O)O)N1CC[C@H](NS(=O)(=O)c2ccc(N(C)C)nc2)C1=O] | 0.14 | 0.002 |
| 25 | (R)-3-(1-Amino-7-methoxy-isoquinolin-6-yl)-2-[(S)-3-(6-dimethylamino-pyridine-3-sulfonylamino)-2-oxo-pyrrolidin-1-yl]-propionic acid ethyl ester | 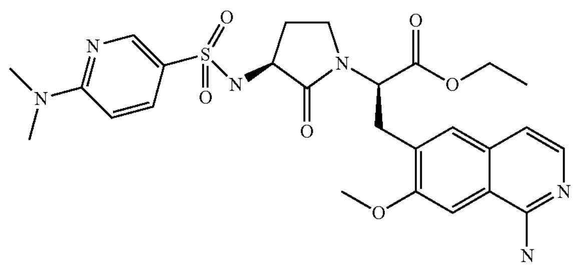 [SMILES: CCOC(=O)[C@@H](Cc1cc2ccnc(N)c2cc1OC)N1CC[C@H](NS(=O)(=O)c2ccc(N(C)C)nc2)C1=O] | 1.10 | 0.097 |
| 26 | (R)-3-(1-Amino-7-methoxy-isoquinolin-6-yl)-2-[(S)-3-(5-chloro-6-dimethylamino-pyridine-3-sulfonylamino)-2-oxo pyrrolidin-1-yl]-propionic acid | 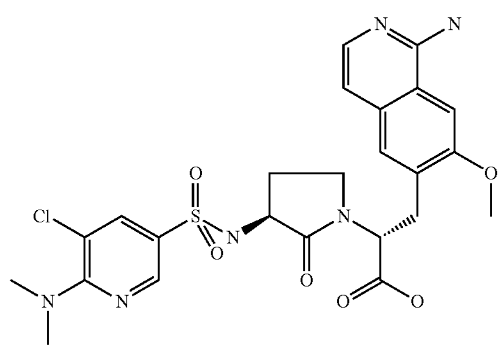 | 0.12 | 0.10 |
| 27 | (R)-3-(1-Amino-7-methoxy-isoquinolin-6-yl)-2-[(S)-3-(5-chloro-6-dimethylamino-pyridine-3-sulfonylamino)-2-oxo pyrrolidin-1-yl]-propionic acid ethyl ester | 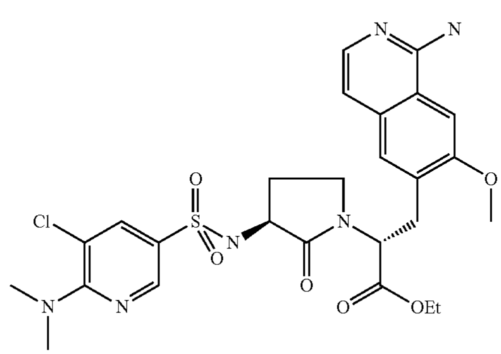 | ND | ND |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 28 | (R)-3-(1-Amino-7-methyl-isoquinolin-6-yl)-2-[(S)-3-(2-dimethylamino-thiazole-5-sulfonylamino)-2-oxo-pyrrolidin-1-yl]-propionic acid | 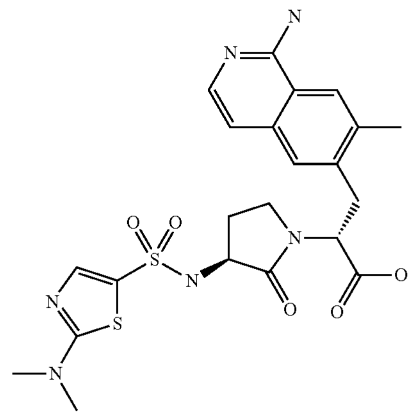 | 0.15 | 0.034 |
| 29 | (R)-3-(1-Amino-7-methyl-isoquinolin-6-yl)-2-[(S)-2-oxo-3-(2-pyrrolidin-1-yl-thiazole-5-sulfonylamino)-pyrrolidin-1-yl]-propionic acid | 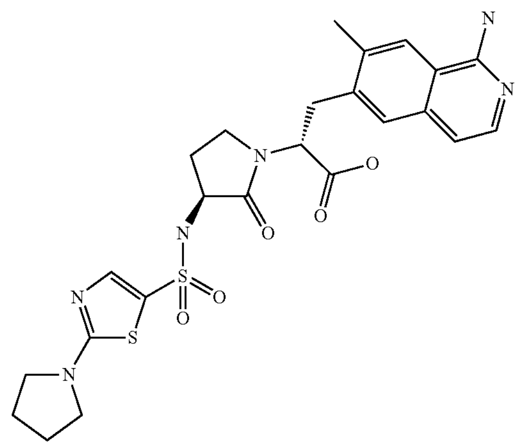 [SMILES: Cc1cc2c(N)nccc2cc1C[C@H](C(=O)O)N1CC[C@H](NS(=O)(=O)c2cnc(N3CCCC3)s2)C1=O] | 0.19 | 0.15 |
| 30 | (R)-3-(1-Amino-7-ethyl-isoquinolin-6-yl)-2-[(S)-3-(2-dimethylamino-thiazole-5-sulfonylamino)-2-oxo-pyrrolidin-1-yl]-propionic acid | 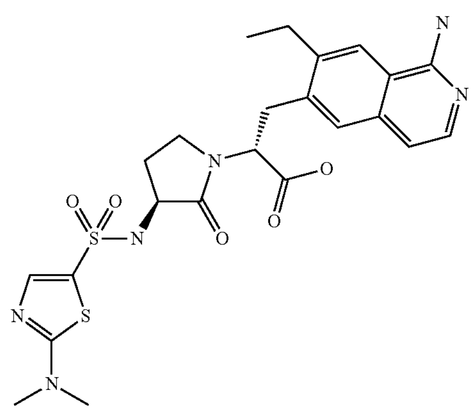 [SMILES: CCc1cc2c(N)nccc2cc1C[C@H](C(=O)O)N1CC[C@H](NS(=O)(=O)c2cnc(N(C)C)s2)C1=O] | 0.15 | 0.012 |
| 31 | (R)-3-(1-Amino-7-ethyl-isoquinolin-6-yl)-2-[(S)-3-(2-dimethylamino-thiazole-5-sulfonylamino)-2-oxo-pyrrolidin-1-yl]-propionic acid ethyl ester | 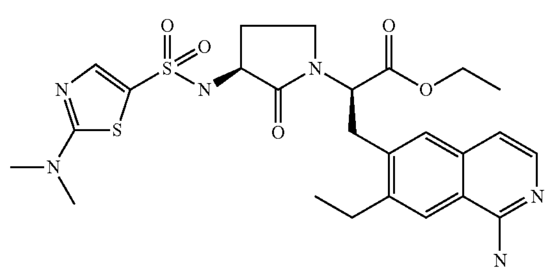 [SMILES: CCOC(=O)[C@@H](Cc1cc2ccnc(N)c2cc1CC)N1CC[C@H](NS(=O)(=O)c2cnc(N(C)C)s2)C1=O] | 2.90 | ND |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 32 | (R)-3-(1-Amino-7-ethyl-isoquinolin-6-yl)-2-[(S)-2-oxo-3-(2-pyrrolidin-1-yl-thiazole-5-sulfonylamino)-pyrrolidin-1-yl]-propionic acid | 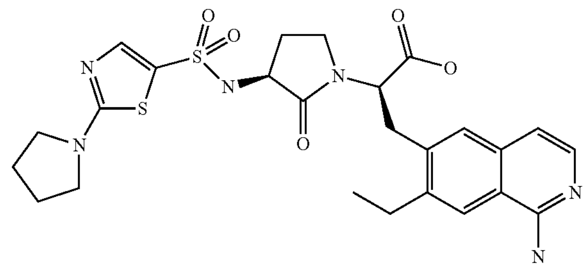 [SMILES: CCc1cc2c(N)nccc2cc1C[C@H](C(=O)O)N1CC[C@H](NS(=O)(=O)c2cnc(N3CCCC3)s2)C1=O] | 0.18 | 0.048 |
| 33 | (R)-3-(1-Amino-7-ethyl-isoquinolin-6-yl)-2-[(S)-2-oxo-3-(2-pyrrolidin-1-yl-thiazole-5-sulfonylamino)-pyrrolidin-1-yl]-propionic acid ethyl ester | 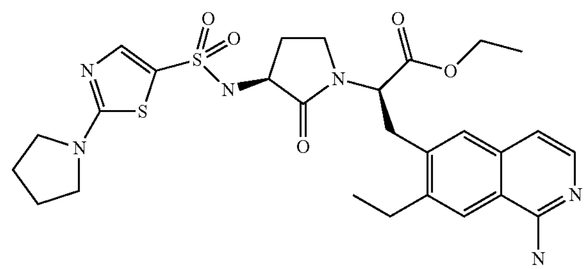 [SMILES: CCOC(=O)[C@@H](Cc1cc2ccnc(N)c2cc1CC)N1CC[C@H](NS(=O)(=O)c2cnc(N3CCCC3)s2)C1=O] | >5 | ND |
| 34 | (R)-3-(1-Amino-7-ethyl-isoquinolin-6-yl)-2-[(S)-3-(6-dimethylamino-pyridine-3-sulfonylamino)-2-oxo-pyrrolidin-1-yl]-propionic acid | 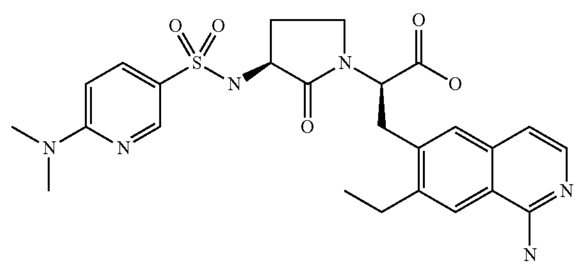 [SMILES: CCc1cc2c(N)nccc2cc1C[C@H](C(=O)O)N1CC[C@H](NS(=O)(=O)c2ccc(N(C)C)nc2)C1=O] | ND | 0.032 |
| 35 | (R)-3-(1-Amino-7-ethyl-isoquinolin-6-yl)-2-[(S)-3-(6-dimethylamino-pyridine-3-sulfonylamino)-2-oxo-pyrrolidin-1-yl]-propionic acid ethyl ester | 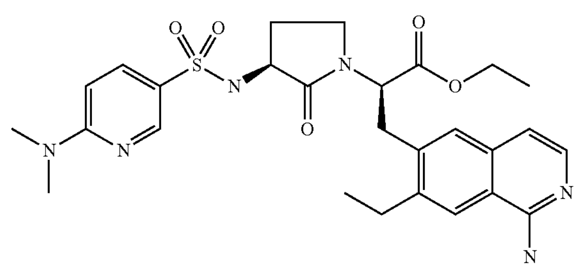 [SMILES: CCOC(=O)[C@@H](Cc1cc2ccnc(N)c2cc1CC)N1CC[C@H](NS(=O)(=O)c2ccc(N(C)C)nc2)C1=O] | ND | ND |
| 36 | (R)-3-(1-Amino-7-ethyl-isoquinolin-6-yl)-2-[(S)-2-oxo-3-(6-pyrrolidin-1-yl-pyridine-3-sulfonylamino)-pyrrolidin-1-yl]-propionic acid | 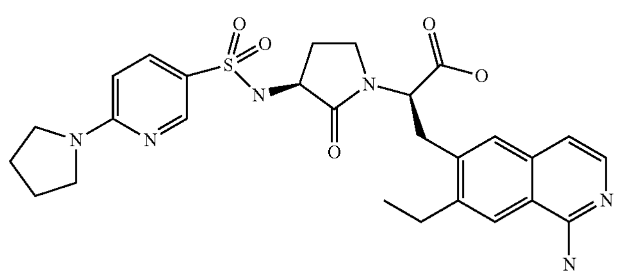 [SMILES: CCc1cc2c(N)nccc2cc1C[C@H](C(=O)O)N1CC[C@H](NS(=O)(=O)c2ccc(N3CCCC3)nc2)C1=O] | 0.15 | 0.47 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 37 | (R)-3-(1-Amino-7-ethyl-isoquinolin-6-yl)-2-[(S)-2-oxo-3-(6-pyrrolidin-1-yl-pyridine-3-sulfonylamino)-pyrrolidin-1-yl]-propionic acid ethyl ester | 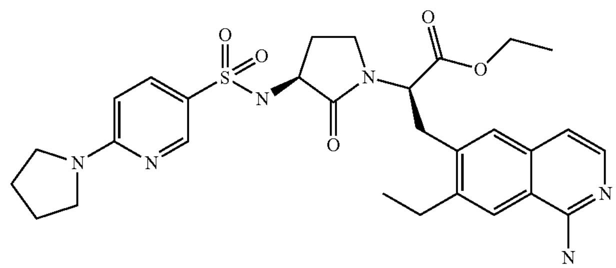 [SMILES: CCOC(=O)[C@@H](Cc1cc2ccnc(N)c2cc1CC)N1CC[C@H](NS(=O)(=O)c2ccc(N3CCCC3)nc2)C1=O] | ND | ND |
| 38 | (R)-3-(1-Amino-7-ethyl-isoquinolin-6-yl)-2-[(S)-3-(5-chloro-6-dimethylamino-pyridine-3-sulfonylamino)-2-oxo-pyrrolidin-1-yl]-propionic acid | 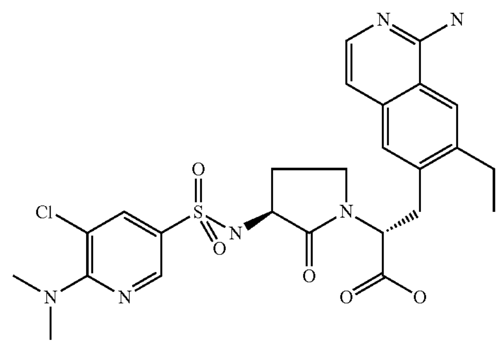 [SMILES: CCc1cc2c(N)nccc2cc1C[C@H](C(=O)O)N1CC[C@H](NS(=O)(=O)c2cnc(N(C)C)c(Cl)c2)C1=O] | ND | ND |
| 39 | (R)-3-(1-Amino-7-ethyl-isoquinolin-6-yl)-2-[(S)-3-(5-chloro-6-dimethylamino-pyridine-3-sulfonylamino)-2-oxo-pyrrolidin-1-yl]-propionic acid ethyl ester | 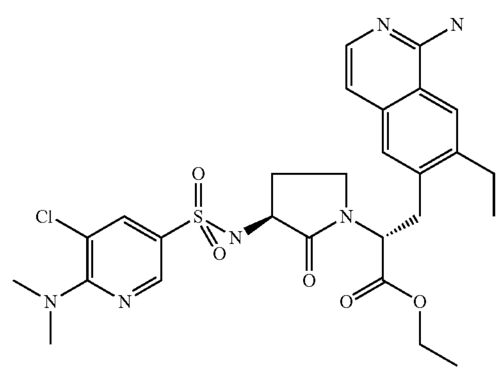 [SMILES: CCOC(=O)[C@@H](Cc1cc2ccnc(N)c2cc1CC)N1CC[C@H](NS(=O)(=O)c2cnc(N(C)C)c(Cl)c2)C1=O] | ND | ND |
| 40 | (R)-3-(1-Amino-7-fluoro-isoquinolin-6-yl)-2-[(S)-3-(2-dimethylamino-thiazole-5-sulfonylamino)-2-oxo-pyrrolidin-1-yl]-propionic acid | 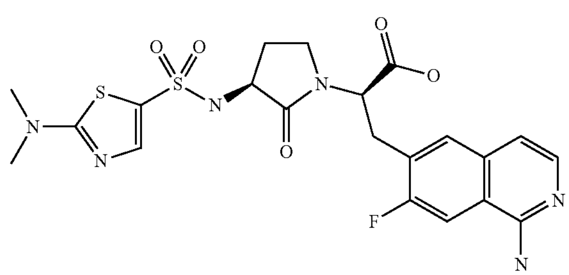 [SMILES: CN(C)c1ncc(S(=O)(=O)N[C@H]2CCN([C@H](Cc3cc4ccnc(N)c4cc3F)C(=O)O)C2=O)s1] | 0.10 | 0.022 |
| 41 | (R)-3-(1-Amino-7-fluoro-isoquinolin-6-yl)-2-[(S)-2-oxo-3-(2-pyrrolidin-1-yl-thiazole-5-sulfonylamino)-pyrrolidin-1-yl]-propionic acid | 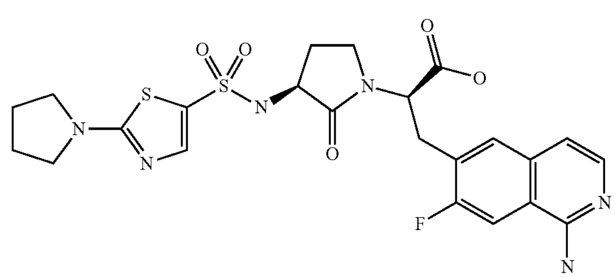 [SMILES: Nc1nccc2cc(C[C@H](C(=O)O)N3CC[C@H](NS(=O)(=O)c4cnc(N5CCCC5)s4)C3=O)c(F)cc12] | 0.12 | 0.047 |

TABLE I-continued

| | IUPAC Name generated from AutoNom ® (MDL, Elsevier) | Chemical Structure | IC 50 (µM) IXa | IC50 (µM) Xa |
|---|---|---|---|---|
| 42 | (R)-3-(1-Amino-7-fluoro-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid | 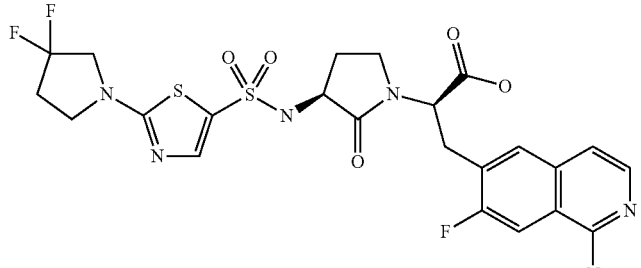 | 0.12 | 1.20 |
| 43 | (R)-3-(1-Amino-7-trifluoromethoxy-isoquinolin-6-yl)-2-[(S)-3-(2-dimethylamino-thiazole-5-sulfonylamino)-2-oxo-pyrrolidin-1-yl]-propionic acid methyl ester | 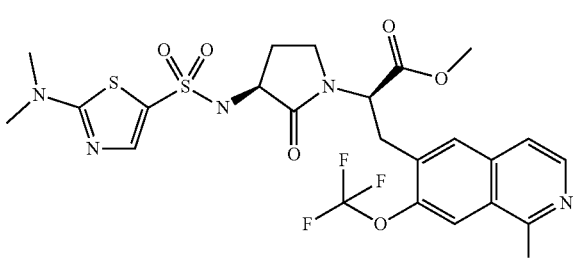 | 0.53 | 0.060 |
| 44 | (R)-3-(1-Amino-7-trifluoromethoxy-isoquinolin-6-yl)-2-[(S)-3-(2-dimethylamino-thiazole-5-sulfonylamino)-2-oxo-pyrrolidin-1-yl]-propionic acid | 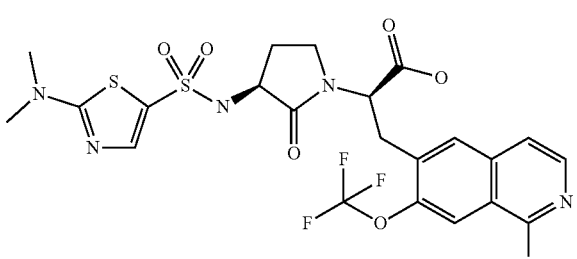 | 0.12 | 0.014 |
| 45 | (R)-3-(1-Amino-7-ethoxy-isoquinolin-6-yl)-2-[(S)-3-(2-dimethylamino-thiazole-5-sulfonylamino)-2-oxo-pyrrolidin-1-yl]-propionic acid | 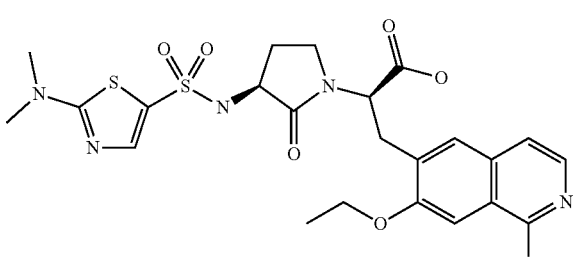 | 0.16 | 0.067 |
| 46 | (R)-3-(1-Amino-7-ethoxy-isoquinolin-6-yl)-2-[(S)-2-oxo-3-(2-pyrrolidin-1-yl-thiazole-5-sulfonylamino)-pyrrolidin-1-yl]-propionic acid | 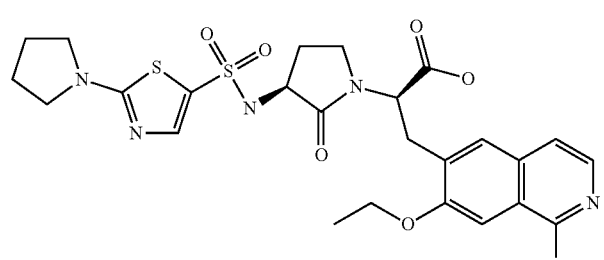 | 0.13 | 0.0084 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 47 | (R)-3-(1-Amino-7-ethoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid | 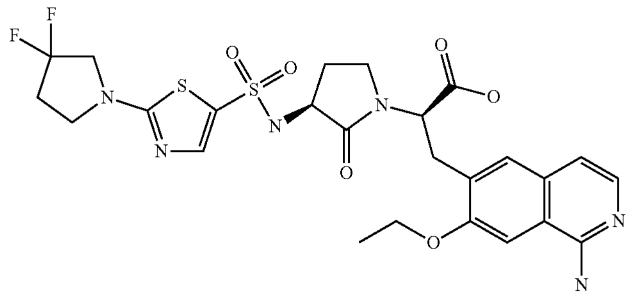 [SMILES: CCOc1cc2c(N)nccc2cc1C[C@H](C(=O)O)N1CC[C@H](NS(=O)(=O)c2cnc(N3CCC(F)(F)C3)s2)C1=O] | 0.16 | 0.19 |
| 48 | (R)-3-(1-Amino-7-hydroxy-isoquinolin-6-yl)-2-[(S)-3-(6-dimethylamino-pyridine-3-sulfonylamino)-2-oxo-pyrrolidin-1-yl]-propionic acid | 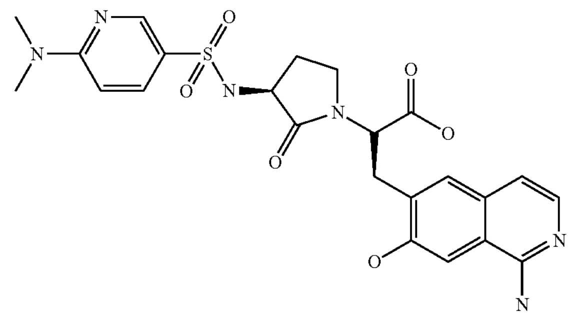 | ND | 0.0064 |
| 49 | (R)-3-(1-Amino-7-chloro-isoquinolin-6-yl)-2-{(S)-3-[2-(cyclobutyl-methyl-amino)-thiazole-5-sulfonylamino]-2-oxo-pyrrolidin-1-yl}-propionic acid | 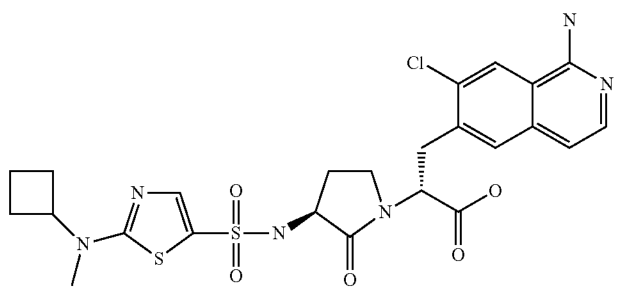 [SMILES: CN(c1ncc(S(=O)(=O)N[C@H]2CCN([C@H](Cc3cc4ccnc(N)c4cc3Cl)C(=O)O)C2=O)s1)C1CCC1] | 0.13 | 0.27 |
| 50 | (R)-3-(1-Amino-7-chloro-isoquinolin-6-yl)-2-[(S)-3-(2-dimethylamino-thiazole-5-sulfonylamino)-2-oxo-pyrrolidin-1-yl]-propionic acid | 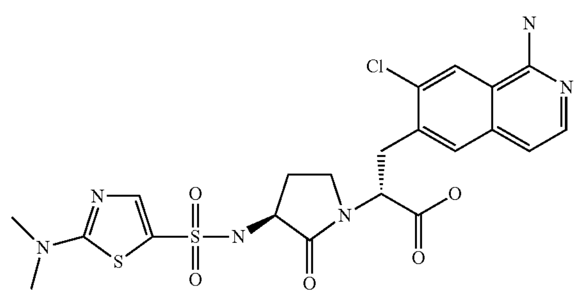 [SMILES: CN(C)c1ncc(S(=O)(=O)N[C@H]2CCN([C@H](Cc3cc4ccnc(N)c4cc3Cl)C(=O)O)C2=O)s1] | 0.16 | 0.005 |
| 51 | (R)-3-(1-Amino-7-chloro-isoquinolin-6-yl)-2-[(S)-3-(2-dimethylamino-thiazole-5-sulfonylamino)-2-oxo-pyrrolidin-1-yl]-propionic acid methyl ester | 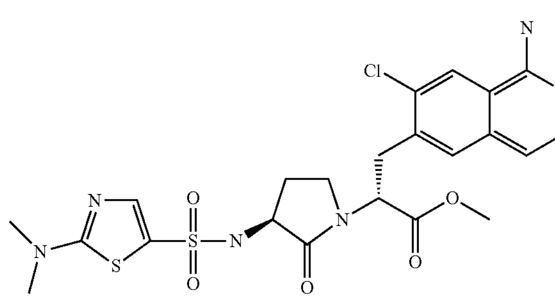 | 1.53 | 0.24 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 52 | (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid methyl ester | 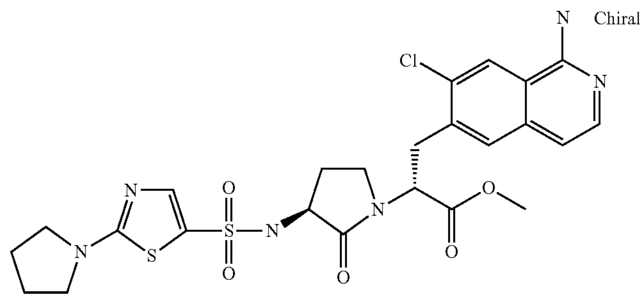 [SMILES: COC(=O)[C@@H](Cc1cc2ccnc(N)c2cc1Cl)N1CC[C@H](NS(=O)(=O)c2cnc(N3CCCC3)s2)C1=O] | 2.08 | 0.41 |
| 53 | (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid | 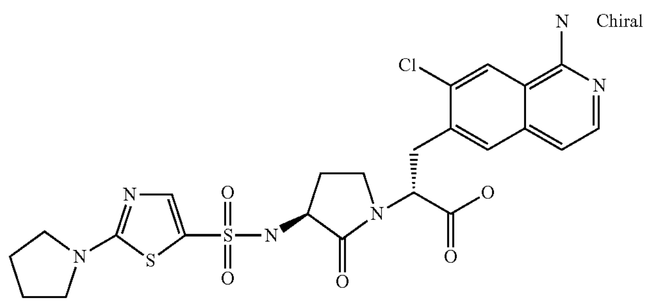 [SMILES: Nc1nccc2cc(C[C@H](C(=O)O)N3CC[C@H](NS(=O)(=O)c4cnc(N5CCCC5)s4)C3=O)c(Cl)cc12] | 0.084 | 0.027 |
| 54 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid methyl ester | 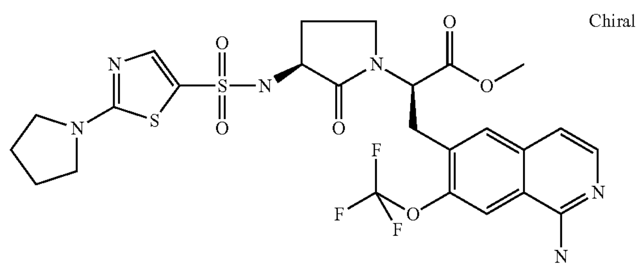 [SMILES: COC(=O)[C@@H](Cc1cc2ccnc(N)c2cc1OC(F)(F)F)N1CC[C@H](NS(=O)(=O)c2cnc(N3CCCC3)s2)C1=O] | 1.09 | 1.12 |
| 55 | (R)-3-(1-Amino-7-trifluoromethoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid methyl ester | 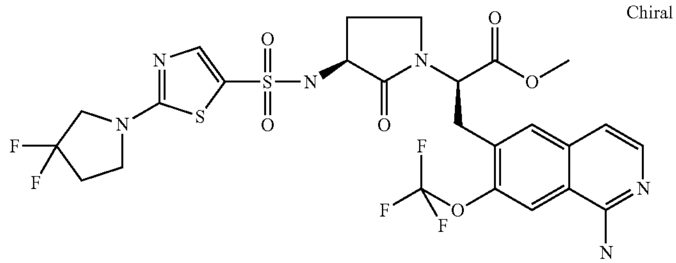 [SMILES: COC(=O)[C@@H](Cc1cc2ccnc(N)c2cc1OC(F)(F)F)N1CC[C@H](NS(=O)(=O)c2cnc(N3CCC(F)(F)C3)s2)C1=O] | 0.55 | 6.12 |
| 56 | (R)-3-(1-Amino-7-trifluoromethoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid | 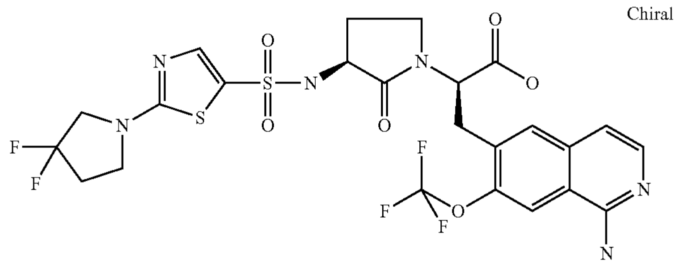 [SMILES: Nc1nccc2cc(C[C@H](C(=O)O)N3CC[C@H](NS(=O)(=O)c4cnc(N5CCC(F)(F)C5)s4)C3=O)c(OC(F)(F)F)cc12] | 0.076 | 0.56 |

TABLE I-continued

| | IUPAC Name generated from AutoNom ® (MDL, Elsevier) | Chemical Structure | | IC 50 (μM) IXa | IC50 (μM) Xa |
|---|---|---|---|---|---|
| 57 | (R)-3-(1-Amino-7-trifluoromethoxy-isoquinolin-6-yl)-2-[(S)-3-(2-azetidin-1-yl-thiazole-5-sulfonylamino)-2-oxo-pyrrolidin-1-yl]-propionic acid methyl ester | 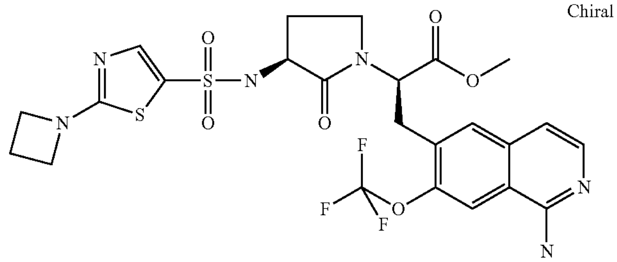 [SMILES: COC(=O)[C@@H](Cc1cc2ccnc(N)c2cc1OC(F)(F)F)N1CC[C@H](NS(=O)(=O)c2cnc(N3CCC3)s2)C1=O] | Chiral | 2.64 | 1.97 |
| 58 | (R)-3-(1-Amino-7-trifluoromethoxy-isoquinolin-6-yl)-2-[(S)-3-(2-azetidin-1-yl-thiazole-5-sulfonylamino)-2-oxo-pyrrolidin-1-yl]-propionic acid | 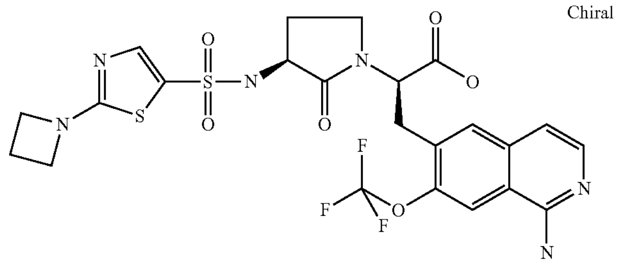 [SMILES: Nc1nccc2cc(C[C@H](C(=O)O)N3CC[C@H](NS(=O)(=O)c4cnc(N5CCC5)s4)C3=O)c(OC(F)(F)F)cc12] | Chiral | 0.14 | 0.035 |
| 59 | (R)-3-(1-Amino-7-trifluoromethoxy-isoquinolin-6-yl)-2-[(S)-3-(6-dimethylamino-pyridine-3-sulfonylamino)-2-oxo-pyrrolidin-1-yl]-propionic acid methyl ester | 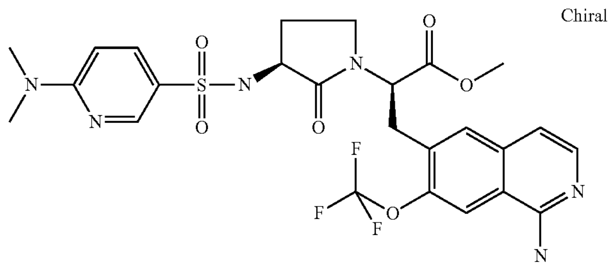 [SMILES: COC(=O)[C@@H](Cc1cc2ccnc(N)c2cc1OC(F)(F)F)N1CC[C@H](NS(=O)(=O)c2ccc(N(C)C)nc2)C1=O] | Chiral | 2.05 | 1.09 |
| 60 | (R)-3-(1-Amino-7-trifluoromethoxy-isoquinolin-6-yl)-2-[(S)-3-(6-dimethylamino-pyridine-3-sulfonylamino)-2-oxo-pyrrolidin-1-yl]-propionic acid | 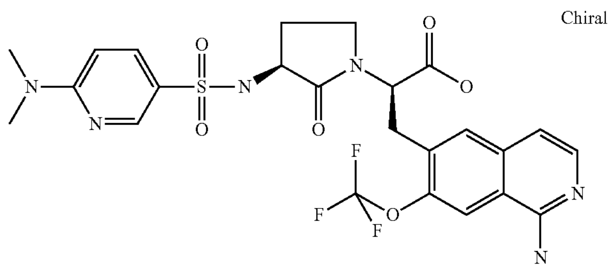 [SMILES: CN(C)c1ccc(S(=O)(=O)N[C@H]2CCN([C@H](Cc3cc4ccnc(N)c4cc3OC(F)(F)F)C(=O)O)C2=O)cn1] | Chiral | 0.13 | 0.034 |
| 61 | (R)-3-(1-Amino-7-chloro-isoquinolin-6-yl)-2-[(S)-3-(6-dimethylamino-pyridine-3-sulfonylamino)-2-oxo-pyrrolidin-1-yl]-propionic acid methyl ester | 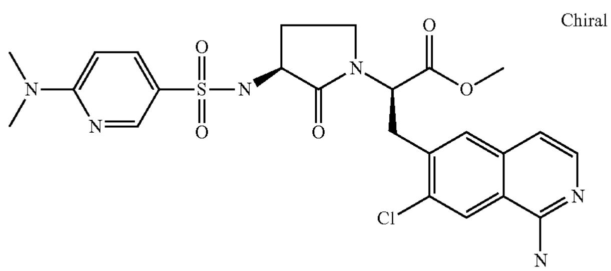 [SMILES: COC(=O)[C@@H](Cc1cc2ccnc(N)c2cc1Cl)N1CC[C@H](NS(=O)(=O)c2ccc(N(C)C)nc2)C1=O] | Chiral | 5.60 | 0.47 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 62 | (R)-3-(1-Amino-7-chloro-isoquinolin-6-yl)-2-[(S)-3-(6-dimethylamino-pyridine-3-sulfonylamino)-2-oxo-pyrrolidin-1-yl]-propionic acid | Chiral | 0.092 | 0.016 |
| 63 | (R)-3-(1-Amino-7-fluoro-isoquinolin-6-yl)-2-[(S)-3-(6-dimethylamino-pyridine-3-sulfonylamino)-2-oxo-pyrrolidin-1-yl]-propionic acid | Chiral | 0.11 | 0.042 |
| 64 | (R)-3-(1-Amino-7-fluoro-isoquinolin-6-yl)-2-[(S)-3-(6-dimethylamino-pyridine-3-sulfonylamino)-2-oxo-pyrrolidin-1-yl]-propionic acid methyl ester | Chiral | 0.62 | 0.40 |
| 65 | (R)-3-(1-Amino-7-chloro-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid methyl ester | Chiral | 3.68 | 5.50 |
| 66 | (R)-3-(1-Amino-7-chloro-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid | Chiral | 0.11 | 0.19 |

TABLE I-continued

| | IUPAC Name generated from AutoNom ® (MDL, Elsevier) | Chemical Structure | | IC 50 (μM) IXa | IC50 (μM) Xa |
|---|---|---|---|---|---|
| 67 | (R)-3-(1-Amino-7-fluoro-isoquinolin-6-yl)-2-[(S)-3-(5-chloro-6-dimethylamino-pyridine-3-sulfonylamino)-2-oxo-pyrrolidin-1-yl]-propionic acid methyl ester | 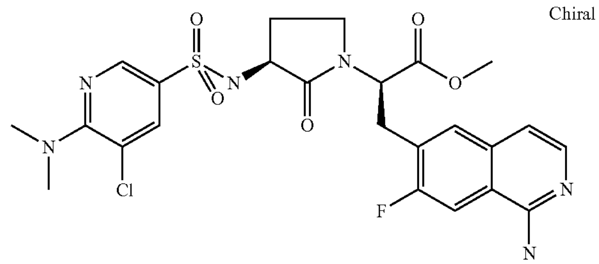 [SMILES: COC(=O)[C@@H](Cc1cc2ccnc(N)c2cc1F)N1CC[C@H](NS(=O)(=O)c2cnc(N(C)C)c(Cl)c2)C1=O] | Chiral | 0.67 | 3.85 (Imax 73%) |
| 68 | (R)-3-(1-Amino-7-fluoro-isoquinolin-6-yl)-2-[(S)-3-(5-chloro-6-dimethylamino-pyridine-3-sulfonylamino)-2-oxo-pyrrolidin-1-yl]-propionic acid | 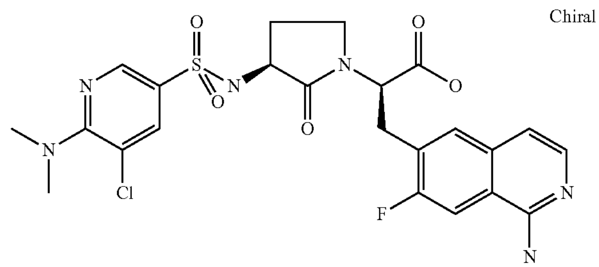 [SMILES: CN(C)c1ncc(S(=O)(=O)N[C@H]2CCN([C@H](Cc3cc4ccnc(N)c4cc3F)C(=O)O)C2=O)cc1Cl] | Chiral | 0.29 | 1.91 (Imax 81%) |
| 69 | (R)-3-(1-Amino-7-chloro-isoquinolin-6-yl)-2-[(S)-3-(5-chloro-6-dimethylamino-pyridine-3-sulfonylamino)-2-oxo-pyrrolidin-1-yl]-propionic acid methyl ester | 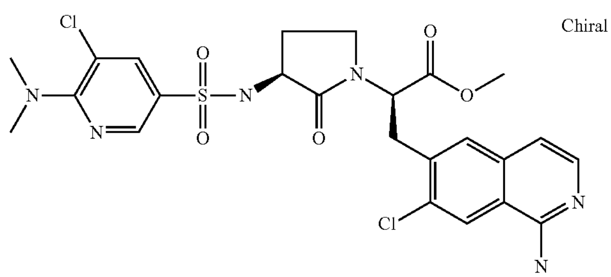 [SMILES: COC(=O)[C@@H](Cc1cc2ccnc(N)c2cc1Cl)N1CC[C@H](NS(=O)(=O)c2cnc(N(C)C)c(Cl)c2)C1=O] | Chiral | >2 | 3.85 (Imax 73%) |
| 70 | (R)-3-(1-Amino-7-chloro-isoquinolin-6-yl)-2-[(S)-3-(5-chloro-6-dimethylamino-pyridine-3-sulfonylamino)-2-oxo-pyrrolidin-1-yl]-propionic acid | 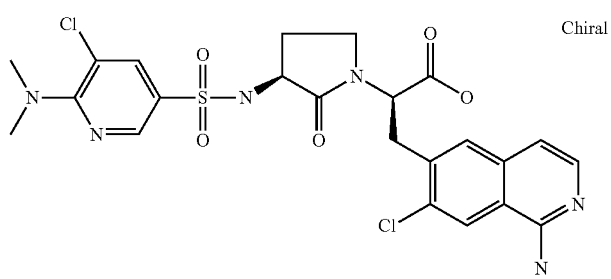 [SMILES: CN(C)c1ncc(S(=O)(=O)N[C@H]2CCN([C@H](Cc3cc4ccnc(N)c4cc3Cl)C(=O)O)C2=O)cc1Cl] | Chiral | 0.27 | 0.59 |
| 71 | (R)-3-(1-Amino-7-fluoro-isoquinolin-6-yl)-2-[(S)-3-(6-dimethylamino-5-methyl-pyridine-3-sulfonylamino)-2-oxo-pyrrolidin-1-yl]-propionic acid methyl ester | 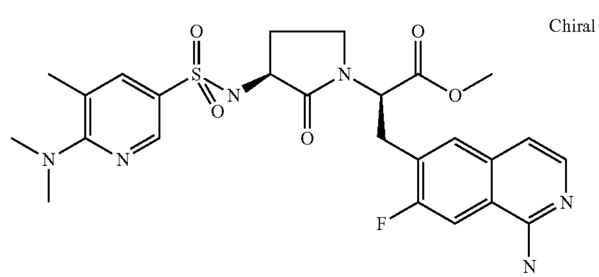 [SMILES: COC(=O)[C@@H](Cc1cc2ccnc(N)c2cc1F)N1CC[C@H](NS(=O)(=O)c2cnc(N(C)C)c(C)c2)C1=O] | Chiral | >2 | ND |

TABLE I-continued

| | IUPAC Name generated from AutoNom ® (MDL, Elsevier) | Chemical Structure | | IC 50 (μM) IXa | IC50 (μM) Xa |
|---|---|---|---|---|---|
| 72 | (R)-3-(1-Amino-7-trifluoromethoxy-isoquinolin-6-yl)-2-[(S)-3-(6-dimethylamino-5-methyl-pyridine-3-sulfonylamino)-2-oxo-pyrrolidin-1-yl]-propionic acid methyl ester | 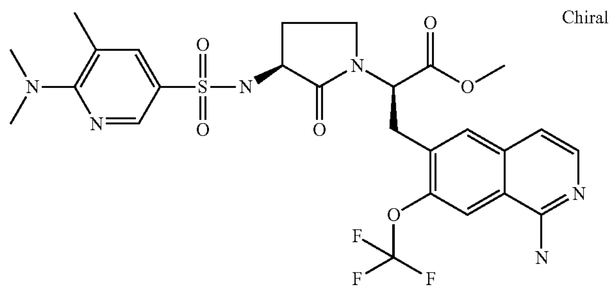 [SMILES: COC(=O)[C@@H](Cc1cc2ccnc(N)c2cc1OC(F)(F)F)N1CC[C@H](NS(=O)(=O)c2cnc(N(C)C)c(C)c2)C1=O] | Chiral | >2 | 5.45 (Imax 71%) |
| 73 | (R)-3-(1-Amino-7-fluoro-isoquinolin-6-yl)-2-[(S)-3-(6-dimethylamino-5-methyl-pyridine-3-sulfonylamino)-2-oxo-pyrrolidin-1-yl]-propionic acid | 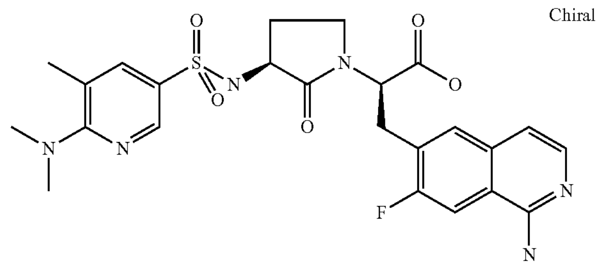 | Chiral | 0.35 | 2.77 (Imax 80%) |
| 74 | (R)-3-(1-Amino-7-trifluoromethoxy-isoquinolin-6-yl)-2-[(S)-3-(6-dimethylamino-5-methyl-pyridine-3-sulfonylamino)-2-oxo-pyrrolidin-1-yl]-propionic acid | 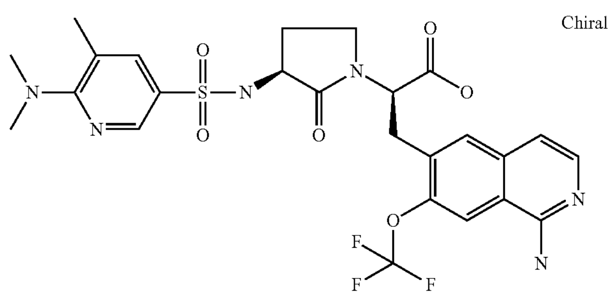 [SMILES: Cc1cc(S(=O)(=O)N[C@H]2CCN([C@H](Cc3cc4ccnc(N)c4cc3OC(F)(F)F)C(=O)O)C2=O)cnc1N(C)C] | Chiral | 0.10 | 0.81 |
| 75 | (R)-3-(1-Amino-7-chloro-isoquinolin-6-yl)-2-[(S)-3-(6-dimethylamino-5-methyl-pyridine-3-sulfonylamino)-2-oxo-pyrrolidin-1-yl]-propionic acid methyl ester | 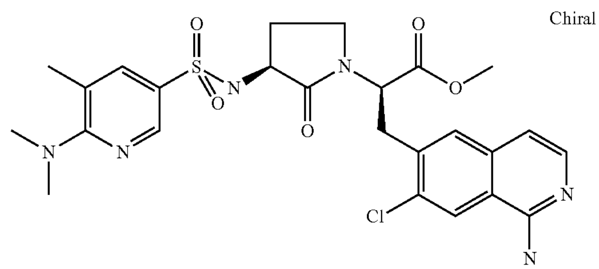 [SMILES: COC(=O)[C@@H](Cc1cc2ccnc(N)c2cc1Cl)N1CC[C@H](NS(=O)(=O)c2cnc(N(C)C)c(C)c2)C1=O] | Chiral | >2 | ND |
| 76 | (R)-3-(1-Amino-7-chloro-isoquinolin-6-yl)-2-[(S)-3-(6-dimethylamino-5-methyl-pyridine-3-sulfonylamino)-2-oxo-pyrrolidin-1-yl]-propionic acid | 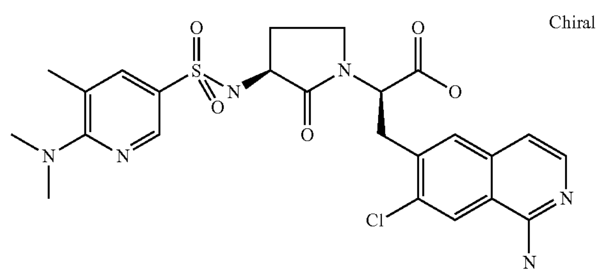 [SMILES: Cc1cc(S(=O)(=O)N[C@H]2CCN([C@H](Cc3cc4ccnc(N)c4cc3Cl)C(=O)O)C2=O)cnc1N(C)C] | Chiral | 0.23 | 0.65 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 77 | (R)-3-(1-Amino-7-trifluoromethoxy-isoquinolin-6-yl)-2-[(S)-3-(2-dimethylamino-thiazole-5-sulfonylamino)-2-oxo-pyrrolidin-1-yl]-propionic acid methyl ester | Chiral | 0.75 | 0.11 |
| 78 | (R)-3-(1-Amino-7-trifluoromethyl-isoquinolin-6-yl)-2-[(S)-3-(2-dimethylamino-thiazole-5-sulfonylamino)-2-oxo-pyrrolidin-1-yl]-propionic acid methyl ester | Chiral | 1.89 | 0.80 |
| 79 | (R)-3-(1-Amino-7-trifluoromethyl-isoquinolin-6-yl)-2-[(S)-3-(2-dimethylamino-thiazole-5-sulfonylamino)-2-oxo-pyrrolidin-1-yl]-propionic acid | Chiral | 0.070 | 0.033 |
| 80 | (R)-3-(1-Amino-7-trifluoromethyl-isoquinolin-6-yl)-2-[(S)-2-oxo-3-(2-pyrrolidin-1-yl-thiazole-5-sulfonylamino)-pyrrolidin-1-yl]-propionic acid methyl ester | Chiral | 2.32, Imax 64% | 3.23, Imax 63% |
| 81 | (R)-3-(1-Amino-7-trifluoromethyl-isoquinolin-6-yl)-2-[(S)-2-oxo-3-(2-pyrrolidin-1-yl-thiazole-5-sulfonylamino)-pyrrolidin-1-yl]-propionic acid | Chiral | 0.086 | 0.37 |

TABLE I-continued

| | IUPAC Name generated from AutoNom ® (MDL, Elsevier) | Chemical Structure | | IC 50 (μM) IXa | IC50 (μM) Xa |
|---|---|---|---|---|---|
| 82 | (R)-3-(1-Amino-7-trifluoromethyl-isoquinolin-6-yl)-2-[(S)-3-(6-dimethylamino-pyridine-3-sulfonylamino)-2-oxo-pyrrolidin-1-yl]-propionic acid methyl ester | 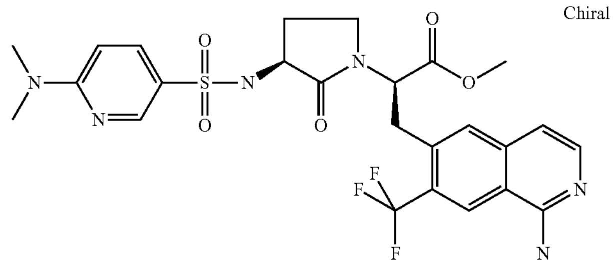 [SMILES: COC(=O)[C@@H](Cc1cc2ccnc(N)c2cc1C(F)(F)F)N1CC[C@H](NS(=O)(=O)c2ccc(N(C)C)nc2)C1=O] | Chiral | 2.42, Imax 59% | 2.43, Imax 69% |
| 83 | (R)-3-(1-Amino-7-trifluoromethyl-isoquinolin-6-yl)-2-[(S)-3-(6-dimethylamino-pyridine-3-sulfonylamino)-2-oxo-pyrrolidin-1-yl]-propionic acid | 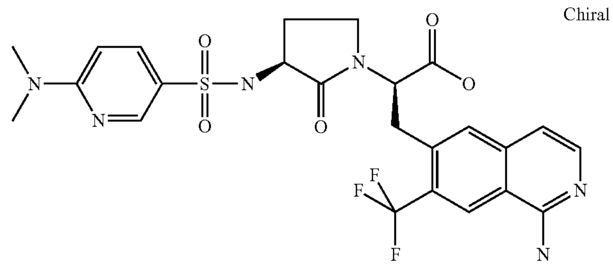 [SMILES: CN(C)c1ccc(S(=O)(=O)N[C@H]2CCN([C@H](Cc3cc4ccnc(N)c4cc3C(F)(F)F)C(=O)O)C2=O)cn1] | Chiral | 0.069 | 0.24 |
| 84 | (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid ethyl ester | 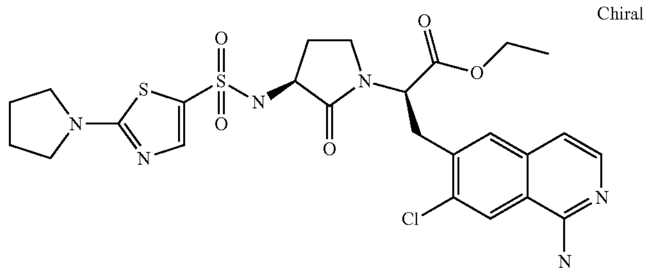 [SMILES: CCOC(=O)[C@@H](Cc1cc2ccnc(N)c2cc1Cl)N1CC[C@H](NS(=O)(=O)c2cnc(N3CCCC3)s2)C1=O] | Chiral | 3.59, Imax = 60% | 0.94 |
| 85 | (R)-3-(1-Amino-7-chloro-isoquinolin-6-yl)-2-[(S)-3-(2-azetidin-1-yl-thiazole-5-sulfonylamino)-2-oxo-pyrrolidin-1-yl]-propionic acid methyl ester | 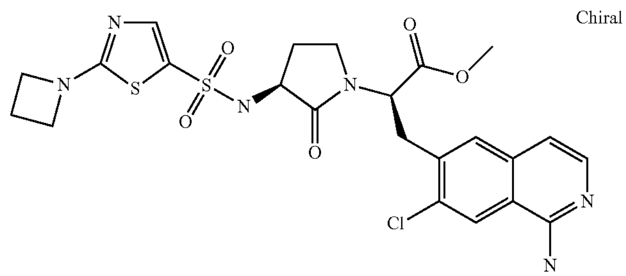 [SMILES: COC(=O)[C@@H](Cc1cc2ccnc(N)c2cc1Cl)N1CC[C@H](NS(=O)(=O)c2cnc(N3CCC3)s2)C1=O] | Chiral | 3.32, Imax = 63% | 0.78 |
| 86 | (R)-3-(1-Amino-7-trifluoromethoxy-isoquinolin-6-yl)-2-[(S)-3-(5-chloro-6-dimethylamino-pyridine-3-sulfonylamino)-2-oxo-pyrrolidin-1-yl]-propionic acid methyl ester | 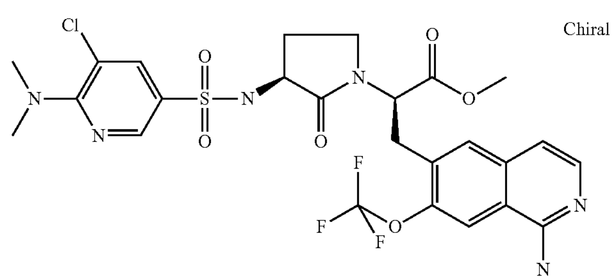 [SMILES: COC(=O)[C@@H](Cc1cc2ccnc(N)c2cc1OC(F)(F)F)N1CC[C@H](NS(=O)(=O)c2cnc(N(C)C)c(Cl)c2)C1=O] | Chiral | 3.1, Imax 50% | 2.84, Imax 43% |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 87 | (R)-3-(1-Amino-7-trifluoromethoxy-isoquinolin-6-yl)-2-[(S)-3-(5-chloro-6-dimethylamino-pyridine-3-sulfonylamino)-2-oxo-pyrrolidin-1-yl]-propionic acid | Chiral | 0.11 | 1.65, Imax 85% |
| 88 | (R)-3-(1-Amino-7-trifluoromethyl-isoquinolin-6-yl)-2-[(S)-3-(2-azetidin-1-yl-thiazole-5-sulfonylamino)-2-oxo-pyrrolidin-1-yl]-propionic acid methyl ester | Chiral | 4.30, Imax 46% | 3.08, Imax 58% |
| 89 | (R)-3-(1-Amino-7-trifluoromethyl-isoquinolin-6-yl)-2-[(S)-3-(2-azetidin-1-yl-thiazole-5-sulfonylamino)-2-oxo-pyrrolidin-1-yl]-propionic acid | Chiral | 0.19 | 0.56 |
| 90 | (R)-3-(1-Amino-7-trifluoromethyl-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid methyl ester | Chiral | 2.05, Imax = 41% | ND |
| 91 | (R)-3-(1-Amino-7-trifluoromethyl-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid | Chiral | 0.12 | 2.18, Imax = 68% |

TABLE I-continued

| | IUPAC Name generated from AutoNom ® (MDL, Elsevier) | Chemical Structure | | IC 50 (μM) IXa | IC50 (μM) Xa |
|---|---|---|---|---|---|
| 92 | (R)-3-(1-Amino-7-chloro-isoquinolin-6-yl)-2-[(S)-3-(2-azetidin-1-yl-thiazole-5-sulfonylamino)-2-oxo-pyrrolidin-1-yl]-propionic acid | 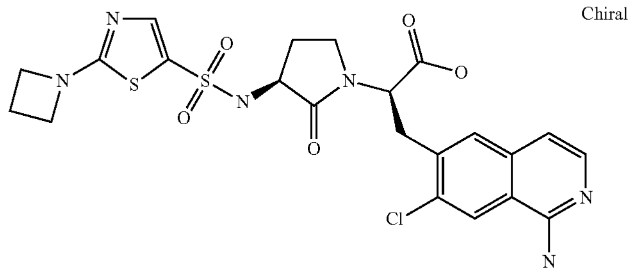 [SMILES: Nc1nccc2cc(C[C@H](C(=O)O)N3CC[C@H](NS(=O)(=O)c4cnc(N5CCC5)s4)C3=O)c(Cl)cc12] | Chiral | 0.12 | 0.019 |
| 93 | (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid butyl ester | 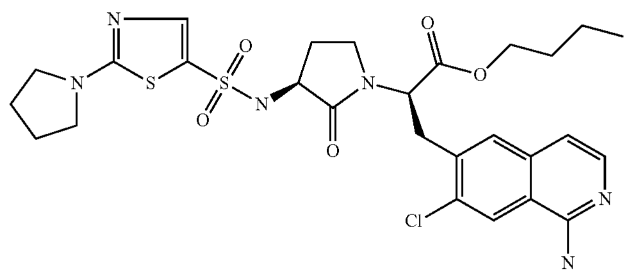 | Chiral | 2.112, Imax = 63% | 1.0 |
| 94 | (R)-3-(1-Amino-7-cyano-isoquinolin-6-yl)-2-[(S)-2-oxo-3-(2-pyrrolidin-1-yl-thiazole-5-sulfonylamino)-pyrrolidin-1-yl]-propionic acid methyl ester | 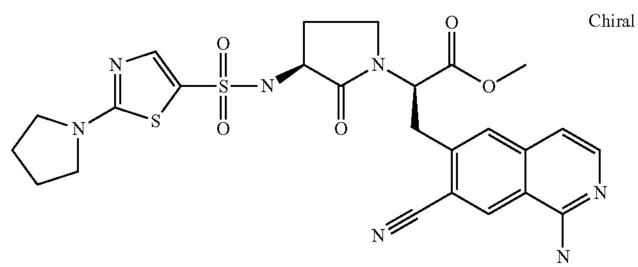 [SMILES: COC(=O)[C@@H](Cc1cc2ccnc(N)c2cc1C#N)N1CC[C@H](NS(=O)(=O)c2cnc(N3CCCC3)s2)C1=O] | Chiral | 2.56, Imax = 58% | 1.06 |
| 95 | (R)-3-(1-Amino-7-cyano-isoquinolin-6-yl)-2-[(S)-2-oxo-3-(2-pyrrolidin-1-yl-thiazole-5-sulfonylamino)-pyrrolidin-1-yl]-propionic acid | 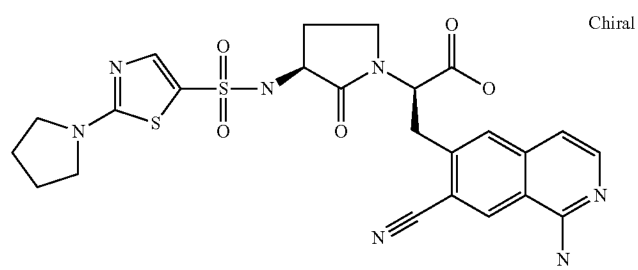 [SMILES: N#Cc1cc2c(N)nccc2cc1C[C@H](C(=O)O)N1CC[C@H](NS(=O)(=O)c2cnc(N3CCCC3)s2)C1=O] | Chiral | 0.080 | 0.025 |
| 96 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid | 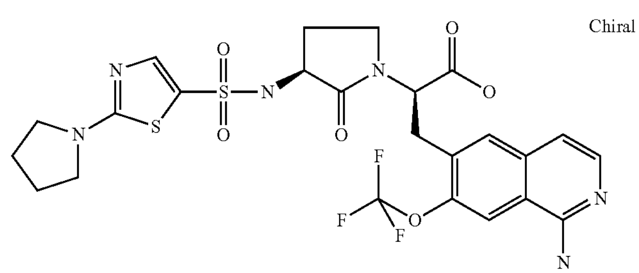 [SMILES: Nc1nccc2cc(C[C@H](C(=O)O)N3CC[C@H](NS(=O)(=O)c4cnc(N5CCCC5)s4)C3=O)c(OC(F)(F)F)cc12] | Chiral | 0.083 | 0.042 |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 97 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid ethyl ester | 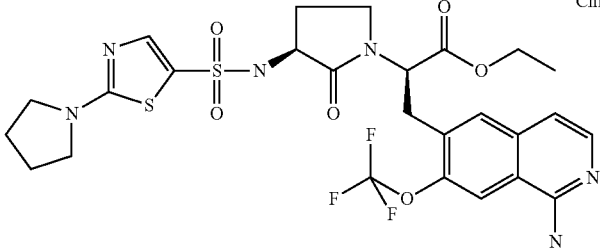 Chiral | ND | ND |
| 98 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid propyl ester | 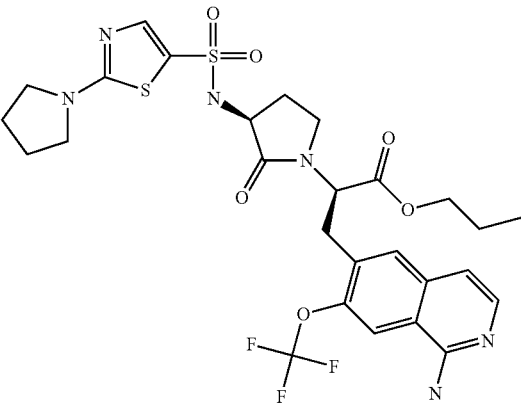 Chiral | ND | ND |
| 99 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid cyclopropylmethyl ester | 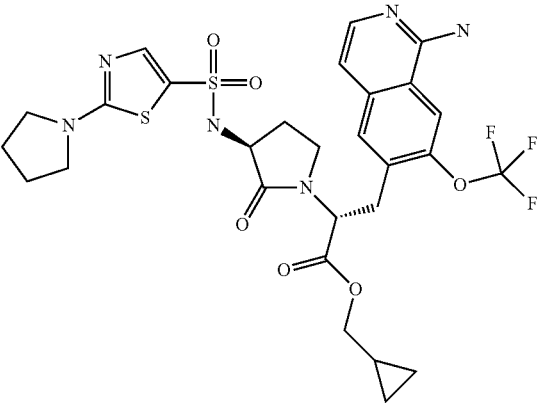 [SMILES: Nc1nccc2cc(C[C@H](C(=O)OCC3CC3)N3CC[C@H](NS(=O)(=O)c4cnc(N5CCCC5)s4)C3=O)c(OC(F)(F)F)cc12] | ND | ND |
| 100 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid butyl ester | 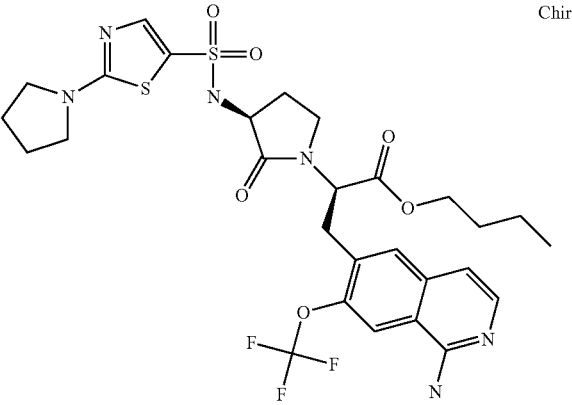 Chiral | ND | ND |

TABLE I-continued

| | IUPAC Name generated from AutoNom ® (MDL, Elsevier) | Chemical Structure | IC 50 (μM) IXa | IC50 (μM) Xa |
|---|---|---|---|---|
| 101 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid isopropyl ester | Chiral | ND | ND |
| 102 | (R)-3-[1-Amino-7-(2-methoxy-ethoxy)-isoquinolin-6-yl]-2-[(S)-3-(2-dimethylamino-thiazole-5-sulfonylamino)-2-oxo-pyrrolidin-1-yl]-propionic acid ethyl ester | 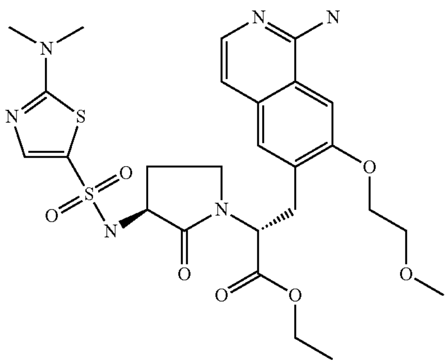 | 3.80 | 0.037 |
| 103 | (R)-3-[1-Amino-7-(2-methoxy-ethoxy)-isoquinolin-6-yl]-2-[(S)-3-(2-dimethylamino-thiazole-5-sulfonylamino)-2-oxo-pyrrolidin-1-yl]-propionic acid | 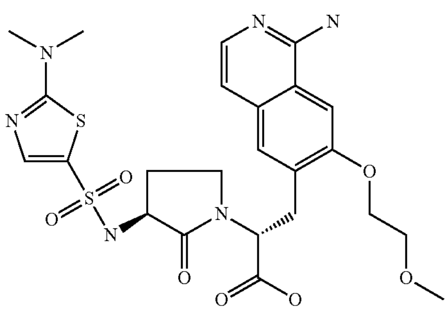 | 0.17 | 0.0014 |
| 104 | (R)-3-(1-Amino-5-fluoro-3-methyl-isoquinolin-6-yl)-2-[(S)-2-oxo-3-(6-pyrrolidin-1-yl-pyridine-3-sulfonylamino)-pyrrolidin-1-yl]-propionic acid | 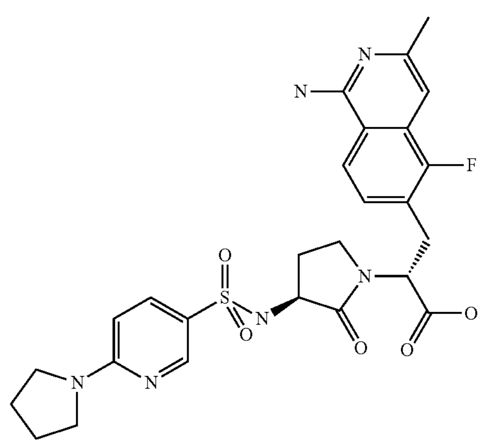 [SMILES: Cc1cc2c(F)c(C[C@H](C(=O)O)N3CC[C@H](NS(=O)(=O)c4ccc(N5CCCC5)nc4)C3=O)ccc2c(N)n1] | ND | ND |

TABLE I-continued

| | IUPAC Name generated from AutoNom ® (MDL, Elsevier) | Chemical Structure | IC 50 (µM) IXa | IC50 (µM) Xa |
|---|---|---|---|---|
| 105 | (R)-3-(1-Amino-5-fluoro-3-methyl-isoquinolin-6-yl)-2-[(S)-2-oxo-3-(6-pyrrolidin-1-yl-pyridine-3-sulfonylamino)-pyrrolidin-1-yl]-propionic acid methyl ester | 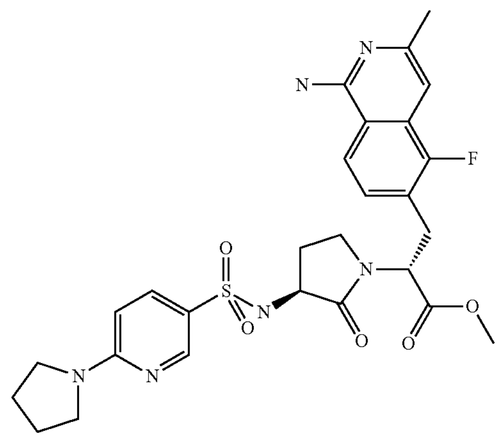 [SMILES: COC(=O)[C@@H](Cc1ccc2c(N)nc(C)cc2c1F)N1CC[C@H](NS(=O)(=O)c2ccc(N3CCCC3)nc2)C1=O] | ND | ND |
| 106 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 2-methoxy-ethyl ester | Chiral | ND | ND |
| 107 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 2,2-dimethyl-propionyloxymethyl ester | Chiral | ND | ND |
| 108 | (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 1-cyclohexyloxycarbonyloxy-ethyl ester | Chiral | ND | ND |

TABLE I-continued

| IUPAC Name generated from AutoNom ® (MDL, Elsevier) | Chemical Structure | IC 50 (µM) IXa | IC50 (µM) Xa |
|---|---|---|---|
| 109 (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid cyclohexyloxycarbonyloxymethyl ester | | ND | ND |
| 110 (2R)-3-[1-amino-7-(trifluoromethoxy)isoquinolin-6-yl]-2-[(3S)-2-oxo-3-{[(2-pyrrolidin-1-yl-1,3-thiazol-5-yl)sulfonyl]amino}pyrrolidin-1-yl]propionic acid methoxymethyl ester | | ND | ND | as well as their enantiomers, diastereoisomers and their mixtures, and the pharmaceutically acceptable salts thereof.

According to a further object, the present invention concerns the process of preparation of the compounds of formula (I) of the invention.

In that which follows, Pg, Pg₁ and Pg₂ are protective groups. Said protective groups are to be understood to mean a group which makes it possible, on the one hand, to protect a reactive functional group, such as a hydroxyl or an amine, during a synthesis and, on the other hand, to regenerate the reactive functional group intact at the end of the synthesis. Examples of protective groups and also of methods for protection and deprotection are given in "Protective Groups in Organic Synthesis", Green et al., 4$^{th}$ Edition (John Wiley & Sons Inc., New York), 2007.

In accordance with the invention, the compounds of general formula (I) can be prepared according to the process presented in Scheme 1.

In Scheme 1, an aminopyrrolidinone is used as starting material.

Scheme 1:

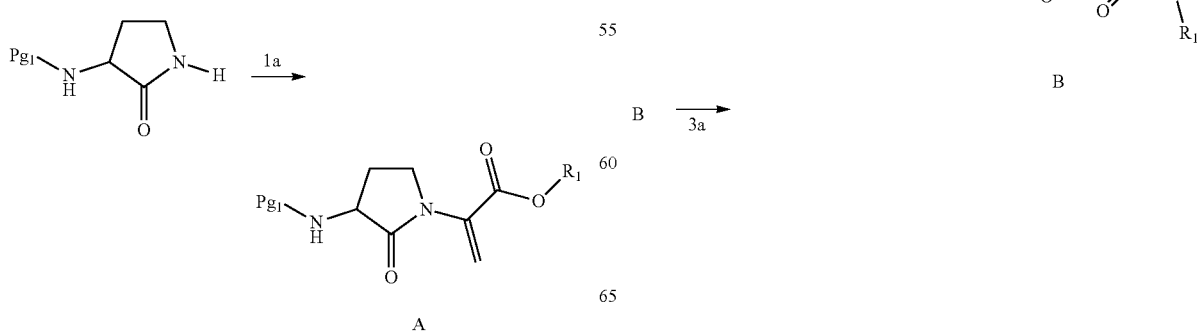

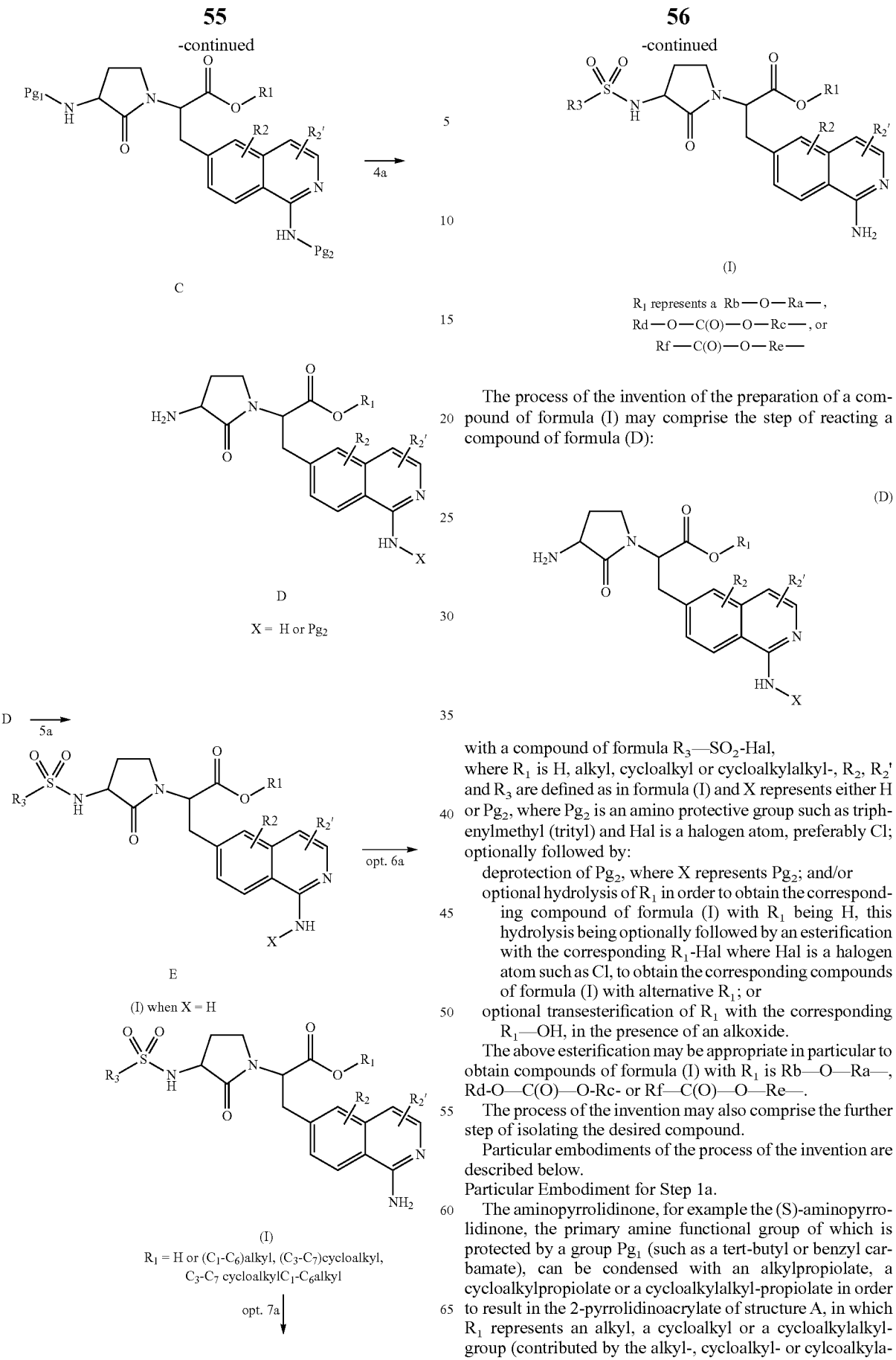

The process of the invention of the preparation of a compound of formula (I) may comprise the step of reacting a compound of formula (D):

with a compound of formula R₃—SO₂-Hal,
where R₁ is H, alkyl, cycloalkyl or cycloalkylalkyl-, R₂, R₂' and R₃ are defined as in formula (I) and X represents either H or Pg₂, where Pg₂ is an amino protective group such as triphenylmethyl (trityl) and Hal is a halogen atom, preferably Cl; optionally followed by:
- deprotection of Pg₂, where X represents Pg₂; and/or
- optional hydrolysis of R₁ in order to obtain the corresponding compound of formula (I) with R₁ being H, this hydrolysis being optionally followed by an esterification with the corresponding R₁-Hal where Hal is a halogen atom such as Cl, to obtain the corresponding compounds of formula (I) with alternative R₁; or
- optional transesterification of R₁ with the corresponding R₁—OH, in the presence of an alkoxide.

The above esterification may be appropriate in particular to obtain compounds of formula (I) with R₁ is Rb—O—Ra—, Rd-O—C(O)—O-Rc- or Rf—C(O)—O—Re—.

The process of the invention may also comprise the further step of isolating the desired compound.

Particular embodiments of the process of the invention are described below.

Particular Embodiment for Step 1a.

The aminopyrrolidinone, for example the (S)-aminopyrrolidinone, the primary amine functional group of which is protected by a group Pg₁ (such as a tert-butyl or benzyl carbamate), can be condensed with an alkylpropiolate, a cycloalkylpropiolate or a cycloalkylalkyl-propiolate in order to result in the 2-pyrrolidinoacrylate of structure A, in which R₁ represents an alkyl, a cycloalkyl or a cycloalkylalkyl-group (contributed by the alkyl-, cycloalkyl- or cylcoalkylalkyl-propiolate). This reaction is advantageously carried out between 0° C. and 110° C., preferably between 20° C. and 40° C., in the presence of a catalytic amount of a phosphine (such as triphenylphosphine) and in an aprotic solvent, such as tetrahydrofuran (THF), dioxane, toluene or dichloromethane.

Particular Embodiment for Step 2a.

The acrylate of structure A can subsequently react with a 6-halogeno-1-aminoisoquinoline, such as a 6-bromo-1-aminoisoquinoline (which is substituted by a $R_2$ group as defined above), the primary amine functional group of which is protected by a group $Pg_2$, for example a triphenylmethyl (trityl) group, in the presence of a transition metal complex (for example, palladium acetate in combination with a tetraalkylammonium halide hydrate such as tetraethylammonium chloride hydrate), in an aprotic solvent, such as THF, dioxane, N,N-dimethylformamide (DMF) or N,N-dimethylacetamide (DMA), at a temperature of between 20 and 150° C., to give the compound of 3-(1-aminoisoquinolin-6-yl)-2-pyrrolidinoacrylate type of structure B.

Particular Embodiment for Step 3a.

The derivative B can subsequently be reduced to give the derivative of structure C using hydrogen at a pressure of 1 to 5 bar, at a temperature of between 20 and 100° C., in a protic solvent, such as methanol, ethanol or isopropanol, optionally in combination with an aprotic solvent, such as THF, ethyl acetate or DMF. This hydrogenation can be catalysed by a complex of a transition metal, such as rhodium or ruthenium, with a chiral phosphine, such as 2,2'-bis(diphenylphosphino)-1,1'-binaphthyl (BINAP) or 1,2-bis(2,5-dimethylphospholano)benzene (DUPHOS), such as (R,R)-(DUPHOS)Rh(COD). The derivative of 3-(1-aminoisoquinolin-6-yl)-2-pyrrolidinopropanoate type of structure C thus obtained has the 2R or 2S configuration according to the enantiomer of the chiral phosphine used.

Particular Embodiment for Step 4a.

The derivative D is subsequently obtained by deprotection of $Pg_1$, by techniques known to a person skilled in the art, of the primary amine functional protective group Pg, present on the pyrrolidinone ring. During this stage, the protective group of the primary amine $Pg_2$ of the isoquinoline can either remain present (X=$Pg_2$) or be also removed (X=H). A salt of the compound D may also optionally be formed in acidic medium.

For example, in the case where $Pg_1$ represents a tert-butyl carbamate, the amine of the derivative C is released using an acid in an anhydrous medium, such as hydrogen chloride in dioxane or trifluoroacetic acid in dichloromethane. The amine carried by the isoquinolinyl group will also be released to give the compound D in which $Pg_2$ becomes a hydrogen atom (X=H). Furthermore, in the case where $Pg_1$ represents a benzyl carbamate, the amine of the derivative C can be selectively released by catalytic hydrogenolysis in ethanol or methanol, in the presence of palladium-on-charcoal, in which case the protective group $Pg_2$ on the amine of the isoquinoline will remain present in the derivative D (X=$Pg_2$).

Particular Embodiment for Step 5a.

The derivative D can subsequently be reacted in an aprotic solvent, such as dichloromethane, THF or DMF, with a sulphonyl halide of formula $R_3$—$SO_2$Hal, where $R_3$ is as defined above in connection with the formula (I) and Hal represent a halogen atom, preferably Cl. The reaction is carried out in the presence of a base, in particular a tertiary amine, such as triethylamine or N,N-diisopropylethylamine, at a temperature of between −10° C. and 50° C., to result in the sulphonamide of structure E.

Particular Embodiment for Optional Step 6a.

Optionally, the sulphonamide E is subsequently deprotected to result in the compound of formula (I) in accordance with the present invention.

During this stage, the removal of the protective group $Pg_2$ and optionally the cleavage of the O—$R_1$ bond ($R_1$ being not H) are carried out using organic chemistry techniques well known to a person skilled in the art.

For example, when $R_1$ is methyl and $Pg_2$ is trityl, the $Pg_2$ group is removed by reaction with trifluoroacetic acid in dichloromethane or else with anhydrous hydrogen chloride in dioxane and then the $R_1$ group can optionally be removed by hydrolysis of the ester using sodium hydroxide in an appropriate solvent or mixture of solvents, such as THF, ethanol and water.

The salt of the compound of formula (I) may be obtained by the addition of the corresponding acid.

Particular Embodiments for Optional Step 7a.

According to a first embodiment, compounds of formula (I) in which $R_1$ represents an alkyl, a cycloalkyl or a cycloalkylalkyl may be obtained by transesterification of a compound of formula (I) as obtained in step 6a with the corresponding $R_1$—OH (alcohol, cycloalkylalcohol or cycloalkylalkylalcohol), in the presence of an alkoxide of metal such as titanium (IV) isopropoxide. This reaction is generally conducted at a temperature comprised between 20° C. and the reflux temperature of the reaction mixture.

According to a second embodiment, compounds of formula (I) in which $R_1$ represents a H atom may be obtained from a compound of formula (I) where $R_1$ is $C_1$-$C_6$ alkyl, cycloalkyl or cycloalkylalkyl as obtained in step 6a by hydrolysis of $R_1$.

More particularly, the hydrolysis may be carried out in aqueous acidic media such as 1M hydrochloric acid at a temperature comprised between 20° C. and the reflux temperature of the reaction mixture, such as 80° C. to provide the corresponding carboxylic acid where $R_1$ is Hydrogen.

According to a third embodiment, compounds of formula (I) in which $R_1$ represents a Rb—O—Ra—, Rd-O—C(O)—O-Rc-, or Rf—C(O)—O—Re— group as defined above may be obtained from a compound of formula (I) where $R_1$ is $C_1$-$C_6$ alkyl, cycloalkyl or cycloalkylalkyl as obtained in step 6a by hydrolysis of $R_1$ in order to obtain the corresponding compound of formula (I) with $R_1$ being H, this hydrolysis being optionally followed by an esterification with the corresponding $R_1$-Hal where Hal is a halogen atom such as Cl.

More particularly, the hydrolysis may be carried out in aqueous acidic media such as 1M hydrochloric acid at a temperature comprised between 20° C. and the reflux temperature of the reaction mixture, such as 80° C. to provide the corresponding carboxylic acid where $R_1$ is Hydrogen. The resulting carboxylic acid is then esterified by reacting the acid with the corresponding compound Rb—O—Ra-Hal, Rd-O—C(O)—O-Rc-Hal, or Rf—C(O)—O—Re-Hal where Hal represents a halogen atom, such as Cl. The compound Rb—O—Ra-Hal may be formed in situ in the presence of Rb—O—Ra—OH with thionyl halogenide, such as thionyl chloride. This esterification reaction may be carried out in the presence of an organic base such as diethylisopropylamine or an inorganic base such as potassium or cesium carbonate at room temperature. Additionally, potassium iodide could be added in the reaction medium for halogen exchange and to improve the alkylation process leading to esters of formula (I) where $R_1$ represents Rb—O—Ra—, Rd-O—C(O)—O-Rc-, or Rf—C(O)—O—Re—, Ra, Rb, Rc, Rd, Re and Rf having the above definitions.

In Scheme 1, the starting compounds and the reactants, when their method of preparation is not described or cited above or below (for instance in the examples), are commercially available or are described in the literature or else can be prepared according to methods which are described therein or which are known to a person skilled in the art.

According to another of its aspects, another subject-matter of the invention is the compounds of formula A, B, C, D and E. These compounds are of use as intermediates in the synthesis of the compounds of formula (I).

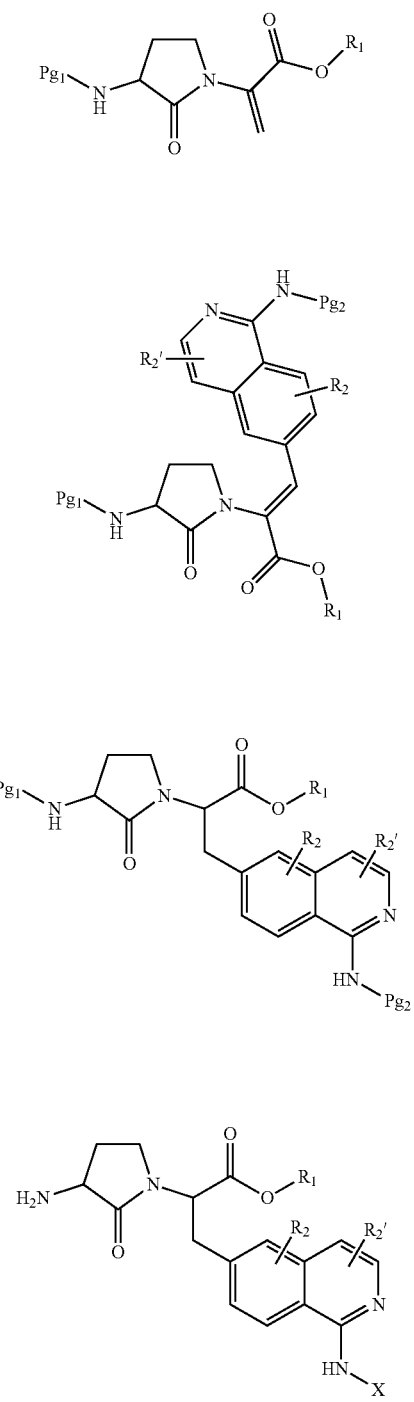

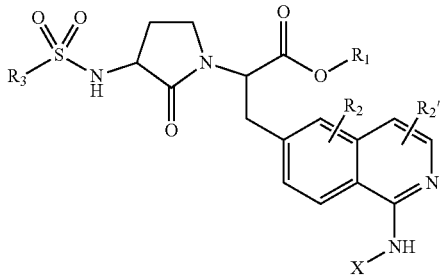

where $R_1$ is H or an alkyl, a cycloalkyl or a cycloalkylalkyl-, $R_2$, $R_2'$ and $R_3$ are defined above, Pg, is an amino protective group, X is H or $Pg_2$ and $Pg_2$ is an amino protective group.

EXAMPLES

The following examples describe the preparation of certain compounds in accordance with the invention. These examples are not limiting and serve only to illustrate the present invention. The numbers of the compounds exemplified refer to those given in the table below, in which the chemical structures and the physical properties of a few compounds according to the invention are illustrated.

In the examples, the following abbreviations are used:
AcOEt: Ethyl acetate
$CH_2Cl_2$: Dichloromethane
$NH_4OH$: ammonium hydroxide
$NH_4OAc$: ammonium acetate
DIEA: Diisopropylethylamine
DMF: N,N-dimethylformamide.
HPLC: High-pressure liquid chromatography
MeOH: Methanol
$MgSO_4$: Magnesium sulfate
M.p.: Melting point
$Na_2SO_4$: Sodium sulfate
$NaHSO_4$: Sodium hydrogeno sulfate
$NaN_3$: sodium azide
r.t: room temperature
Rf: Frontal ratio
TFA: Trifluoroacetic Acid
THF: Tetrahydrofurane
TOTU: O-[(ethoxycarbonyl)cyanomethylenamino]-N,N,N',N'-tetramethyluronium tetrafluoroborate
UPLC: Ultra Performance Liquid Chromatography The nuclear magnetic resonance spectra ($^1$H NMR) are recorded at 400 MHz in d6-DMSO. The following abbreviations are used for the interpretation of the spectra:
s: singulet,
d: doublet,
t: triplet,
q: quadruplet,
qui: quintuplet,
up: unresolved peak,
bs: broad singlet,
dd: doublet of doublet.

Some of the compounds according to the invention are as well analysed by LC/UV/MS coupling (liquid chromatography/UV detection/mass spectrometry). The characteristic molecular peak (MH$^+$, MNa$^+$, etc.) and the retention time (tr) in minutes (min) are measured.

The compounds are analysed by HPLC-UV-MS or alternatively UPLC-UV-MS (liquid chromatography-UV detection and mass detection) coupling.

The analytical conditions are the following:

Conditions A (HPLC):
Use is made of a column: Symmetry C18 (50×2.1 mm; 3.5 μm)
Eluent A: 0.05% of trifluoroacetic acid (TFA) in water at approximately pH 3.1
Eluent B: 0.05% of TFA in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute.
Detection: $\lambda$=210 nm-220 nm Conditions B (HPLC):
Use is made of an XTerra MS C18 column (50×2.1 mm; 3.5 μm)
Eluent A: 5 mM $NH_4OAc$ at approximately pH 7
Eluent B: acetonitrile
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute.
Detection: $\lambda$=220 nm Conditions C (UPLC):
Use is made of an Acquity BEH C18 column (50×2.1 mm; 1.7 μm)
Eluent A: 0.05% of TFA in water at approximately pH 3.1/acetonitrile (97/3)
Eluent B: 0.035% of TFA in acetonitrile.
Gradient:

| Time (min) | % A | % B |
|---|---|---|
| 0 | 100 | 0 |
| 2.3 | 5 | 95 |
| 2.9 | 5 | 95 |
| 3 | 100 | 0 |
| 3.5 | 100 | 0 |

Column temperature: 40° C.; flow rate: 1 ml/minute.
Detection: $\lambda$=220 nm

Conditions D (UPLC):
Use is made of a Jsphere C18 column (33×2 mm; 4 μm)
Eluent A: 0.05% of TFA in water
Eluent B: 0.05% of TFA in acetonitrile.
Gradient:

| Time (min) | % A | % B |
|---|---|---|
| 0 | 95 | 5 |
| 2.5 | 5 | 95 |
| 2.9 | 5 | 95 |
| 3 | 95 | 5 |
| 3.2 | 95 | 5 |

Column temperature: 40° C.; flow rate: 1 ml/minute.
Detection: $\lambda$=220, 254 nm Conditions E (UPLC):
Use is made of a Jsphere C18 column (33×2 mm; 4 μm)
Eluent A: 0.1% of Formic acid in water
Eluent B: 0.08% of Formic acid in acetonitrile.
Gradient:

| Time (min) | % A | % B |
|---|---|---|
| 0 | 95 | 5 |
| 2.5 | 5 | 95 |
| 2.9 | 5 | 95 |
| 3 | 95 | 5 |
| 3.2 | 95 | 5 |

Column temperature: 40° C.; flow rate: 1 ml/minute.
Detection: $\lambda$=220, 254 nm Conditions F (UPLC):
Use is made of a Waters XBridge C18 column (50×4.6 mm; 2.5 μm)
Eluent A: 0.05% of TFA in water
Eluent B: 0.05% of TFA in acetonitrile.
Gradient:

| Time (min) | % A | % B |
|---|---|---|
| 0 | 95 | 5 |
| 3.5 | 5 | 95 |
| 4 | 95 | 5 |

Column temperature: 40° C.; flow rate: 1 ml/minute.
Detection: $\lambda$=220, 254 nm Conditions G (UPLC):
Use is made of a Jsphere C18 column (33×2 mm; 4 μm)
Eluent A: 0.05% of TFA in water
Eluent B: 0.05% of TFA in acetonitrile.
Gradient:

| Time (min) | % A | % B |
|---|---|---|
| 0 | 98 | 2 |
| 1 | 98 | 2 |
| 5 | 5 | 95 |
| 6.25 | 95 | 5 |

Column temperature: 40° C.; flow rate: 1 ml/minute.
Detection: $\lambda$=220, 254 nm Conditions H
Use is made of a Symmetry C18 3.5 μm (2.1×50 mm) column (Waters)

Eluents: A: $H_2O$+0.005% TFA
B: CH3CN+0.005% TFA
Flow rate: 0.4 ml/min.
Gradient:

| Temps (min.) | % B |
|---|---|
| 0 | 0 |
| 30 | 100 |
| 35 | 100 |

Column Temp.: 25° C.
Post run: 5 min.
UV detection: λ=220 nm
Injection volume Volume d'injection: 2 μl of a solution at 0.5 mg/ml
Mass Spectrometry Conditions:

The mass spectra are recorded in positive electrospray mode (ESI), in order to observe the ions derived from the protonation of analysed compounds ($MH^+$), or from the formation of adducts with other cations, such as $Na^+$, $K^+$, etc.

Example 1

(R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid methyl ester hydrochloride (Compound No. 2)

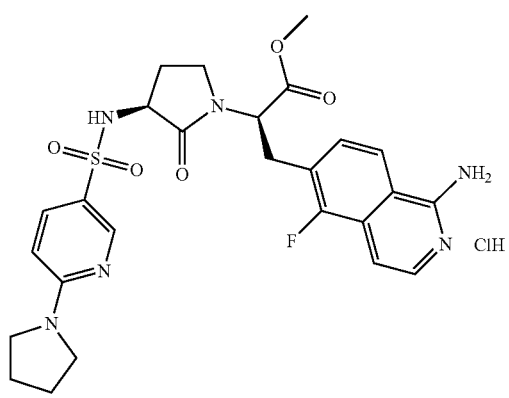 [SMILES: COC(=O)[C@@H](Cc1ccc2c(N)nccc2c1F)N1CC[C@H](NS(=O)(=O)c2ccc(N3CCCC3)nc2)C1=O ; Cl]

1.1: 3-Bromo-2-fluorobenzaldehyde 2,2,6,6-Tetramethylpiperidine (30 g, 212 mmol) and 150 ml of anhydrous THF are introduced into a 500 ml three-necked flask. The medium is cooled to 0° C. under argon and a 1.6M solution of n-butyllithium in hexane (131 ml, 210 mmol) is added dropwise. After stirring at 0° C. for 30 min, the medium is coded to −78° C. and a solution of 1-bromo-2-fluorobenzene (35 g, 200 mmol) in 150 ml of THF is added dropwise. After stirring at −78° C. for 1 hour, 32 ml of anhydrous DMF (412 mmol) are added. The medium is stirred at −78° C. for 30 min. It is run on to a saturated aqueous ammonium chloride solution (300 ml) and extracted with 3×200 ml of ether. The organic phases are washed with a saturated aqueous sodium chloride solution and dried over $MgSO_4$.

The slurry is filtered and the filtrate concentrated. 34 g of an oil are obtained. Rf=0.4 (cyclohexane/ethyl acetate; 90:10).

1.2: 3-(3-Bromo-2-fluorophenyl) acrylic acid

3-Bromo-2-fluorobenzaldehyde (33 g, 163 mmol), ethyl diethylphosphonoacetate (37 g, 167 mmol) and 150 ml of anhydrous THF are introduced into a 500 ml three-necked flask. The medium is cooled to 0° C. under argon and a solution of 1,8-diazabicyclo[5.4.0]undec-7-ene (DBU) (25 ml, 163 mmol) in 100 ml of THF is added dropwise. After stirring at 20° C. for 1 hour, the THF is removed under vacuum and the medium is run on to 200 ml of a 1M aqueous hydrochloric acid solution. The product is extracted with 3×100 ml of ethyl acetate. The organic phases are washed with a saturated aqueous sodium bicarbonate solution and a saturated aqueous sodium chloride solution and dried over $MgSO_4$. The slurry is filtered and the filtrate concentrated. The residue (42 g, 100% crude) is taken up in 200 ml of THF and cooled to 0° C. 200 ml of a 1M aqueous sodium hydroxide solution are added and the medium is stirred at 20° C. for 18 h. 200 ml of a 1M aqueous hydrochloric acid solution are added and the medium is concentrated in order to remove the THF. A suspension is obtained and is filtered, and the solid is washed with water and dried over $P_2O_5$.

36 g of beige solid are obtained. Rf=0.2 ($CH_2Cl_2$/MeOH; 95:5).

1.3: 6-Bromo-5-fluoro-2H-isoquinolin-1-one 3-(3-Bromo-2-fluorophenyl)acrylic acid (30 g, 123 mmol) is suspended in 250 ml of toluene. 10 ml (135 mmol) of thionyl chloride are added and the medium is brought to reflux for 6 h. It is concentrated to dryness and a solid is obtained.

The acid chloride thus obtained is dissolved in 120 ml of dioxane and added at 0° C. to a solution of sodium azide (12 g, 185 mmol) in 100 ml of a 50:50 mixture of dioxane and water. The medium is stirred for 1 h and extracted with 3×200 ml of ether. The organic phases are washed with a saturated aqueous sodium bicarbonate solution and a saturated aqueous sodium chloride solution and dried over $MgSO_4$. The slurry is filtered, 100 ml of diphenyl ether are added and the medium is concentrated at a temperature of less than 40° C. behind a protective screen. The residue comprising the acyl azide is added over 1 hour to 100 ml of diphenyl ether at 250° C. The medium is maintained at 250° C. for 3 h after the addition. After cooling, the medium is run on to 1 litre of a cyclohexane/ethyl acetate mixture (90:10). The mixture is left standing for 18 h and filtered. The solid is washed with cyclohexane and then dried over $P_2O_5$.

12 g of beige solid are obtained. Rf=0.33 ($CH_2Cl_2$/MeOH; 95:5).

1.4: 6-Bromo-1-chloro-5-fluoroisoquinoline

6-Bromo-5-fluoro-2H-isoquinolin-1-one (12 g, 49.5 mmol) is suspended in 50 ml of phosphoryl chloride. The medium is brought to 110° C. for 2 h. It is concentrated to dryness and then run on to 200 ml of ice. 200 ml of dichloromethane are added and neutralization is carried out with solid sodium bicarbonate. Extraction is carried out with 3×200 ml of dichloromethane and the organic phases are washed with a saturated aqueous sodium chloride solution and dried over $MgSO_4$. The slurry is filtered and the filtrate concentrated.

12 g of beige solid are obtained. Rf=0.5 (cyclohexane/ethyl acetate; 80:20).

1.5: 6-Bromo-5-fluoro-1-phenoxyisoquinoline 32 g of phenol (345 mmol) and 4.5 g (80.5 mmol) of potassium hydroxide are introduced into a 100 ml round-bottomed flask. The medium is brought to 50° C. until a homogeneous solution is obtained and 6-bromo-1-chloro-5-fluoroisoquinoline (12 g, 46 mmol) is added. The medium is brought to 160° C. for 2 h. After cooling, it is run on to a mixture of ice (150 ml) and 10N sodium hydroxide (50 mmol). Extraction is carried out with 3×200 ml of dichloromethane and the organic phases are washed with a saturated aqueous sodium chloride solution and dried over $MgSO_4$. The slurry is filtered and the filtrate concentrated.

14 g of a brown solid are obtained. Rf=0.45 (cyclohexane/ethyl acetate 80:20).

1.6: 6-Bromo-5-fluoroisoquinolin-1-ylamine 66 g of ammonium acetate (850 mmol) and 6-bromo-5-fluoro-1-phenoxyisoquinoline (13.8 g, 43 mmol) are introduced into a 100 ml round-bottomed flask. The medium is brought to 160° C. for 6 h. After cooling, it is run on to a mixture of ice (150 ml) and 10N sodium hydroxide (50 mmol). The mixture is stirred vigorously and brought to pH=14 with 10N sodium hydroxide. The precipitate is filtered off and washed with cold water. The yellow solid is dried over $P_2O_5$.

9 g of a yellow solid are obtained. Rf=0.25 ($CH_2Cl_2$/MeOH; 95:5).

1.7: (6-Bromo-5-fluoroisoquinolin-1-yl)tritylamine

6-Bromo-5-fluoroisoquinolin-1-ylamine (8.5 g, 35 mmol) and 50 ml of anhydrous DMF are introduced in a 25 ml round-bottomed flask. 5.9 ml of triethylamine (42 mmol) and then trityl chloride (10 g, 36 mmol) are added. The medium is brought to 50° C. for 16 h. It is concentrated to dryness and the residue taken up in 100 ml of water. The precipitate is filtered off, washed with water and dried over $P_2O_5$. The solid is filtered through 300 g of silica with pure dichloromethane as eluent.

14.8 g of an off-white solid are obtained. Rf=0.85 (cyclohexane/ethyl acetate; 60:40).

1.8: Methyl (S)-2-(3-benzyloxycarbonylamino-2-oxopyrrolidin-1-yl)acrylate 4.68 g (20 mmol) of benzyl (S)-(2-oxopyrrolidin-3-yl)carbamate (J. W. Skiles et al., Bioorg. and Med. Chem., 1993, 3(4), 773) and 524 mg (2 mmol) of triphenylphosphine are suspended in 40 ml of dichloromethane. A solution of methyl propiolate (2 g, 24 mmol) in 10 ml of dichloromethane is added over 5 min. The medium is stirred at 20° C. for 2 h and then partially concentrated. The product is purified by chromatography on a column of silica (200 g), elution being carried out with an ethyl acetate/cyclohexane mixture (40:60).

4.16 g of a solid are obtained. Rf=0.4 (MeOH/$CH_2Cl_2$; 5:95).

1.9: Methyl Z-(S)-2-(3-benzyloxycarbonylamino-2-oxopyrrolidin-1-yl)-3-(5-fluoro-1-(tritylamino)isoquinolin-6-yl)acrylate 1.8 g (3.72 mmol) of (6-bromo-5-fluoroisoquinolin-1-yl)tritylamine obtained in 1.7, 0.46 g (3.72 mmol) of tetraethylammonium chloride hydrate and 0.94 g (11.2 mmol) of sodium hydrogen carbonate are suspended in 7.5 ml of anhydrous DMF in a 50 ml round-bottomed flask surmounted by a reflux condenser. The solution is degassed by sparging with argon and 1.18 g (3.72 mmol) of methyl (S)-2-(3-benzyloxycarbonylamino-2-oxopyrrolidin-1-yl)acrylate obtained in 1.8 are added, followed by 25 mg of palladium acetate (0.11 mmol). The medium is brought to 90° C. for 16 h. After cooling, the medium is poured on to ice (50 ml) and extracted with ethylacetate (3×50 ml). The combined organic layers are washed with brine, dried over sodium sulphate, filtered and concentrated under vacuum.

After chromatographing on silica gel (120 g, eluent: cyclohexane/ethyl acetate; 60:40), 2.4 g of a yellow solid are obtained. Rf=0.27 (cyclohexane/ethyl acetate; 60:40).

1.10: Methyl (2R)-2-[(3S)-3-benzyloxycarbonylamino-2-oxopyrrolidin-1-yl]-3-(5-fluoro-1-(tritylamino)isoquinolin-6-yl)propanoate 2.4 g (3.3 mmol) of methyl Z-(S)-2-(3-benzyloxycarbonylamino-2-oxopyrrolidin-1-yl)-3-(5-fluoro-1-(tritylamino)isoquinolin-6-yl)acrylate, obtained in 1.9, 2.4 g (3.3 mmol) is suspended in 20 ml of methanol in a 250 ml Parr bottle. The medium is degassed by sparging with nitrogen (30 min) and 155 mg (0.23 mmol) of (R,R)-(DuPhos)Rh(COD) triflate (Strem Chemicals Inc.) are added. The medium is placed under 50 psi of $H_2$ and stirred at 20° C. for 48 h. The medium is concentrated, and the product is purified by chromatography on silica gel (40 g, eluent: cyclohexane/ethyl acetate; 60:40), 2 g (71%) of an amorphous solid are obtained.

Rf=0.18 (cyclohexane/ethyl acetate; 60:40).

1.11: Methyl (2R)-2-[(3S)-3-amino-2-oxopyrrolidin-1-yl]-3-(5-fluoro-1-(tritylamino)isoquinolin-6-yl)propanoate Methyl (2R)-2-[(3S)-3-benzyloxycarbonylamino-2-oxopyrrolidin-1-yl]-3-(5-fluoro-1-(tritylamino)isoquinolin-6-yl)propanoate (2 g, 2.77 mmol) is dissolved in 50 ml of methanol. 200 mg of 10% palladium-on-charcoal are added and the medium is placed under 3 atmospheres of hydrogen for 6 h. It is filtered and then concentrated.

1.5 g of an amorphous solid are obtained. Rf=0.2 ($CH_2Cl_2$/MeOH; 95:5).

1.12: Methyl (2R)-2-[(3S)-2-oxo-3-(6-(pyrrolidin-1-yl)pyridin-3-ylsulphonylamino)pyrrolidin-1-yl]-3-(5-fluoro-1-(tritylamino)isoquinolin-6-yl)propanoate Methyl (2R)-2-[(3S)-3-amino-2-oxopyrrolidin-1-yl]-3-(5-fluoro-1-(tritylamino)isoquinolin-6-yl)propanoate (0.75 g, 1.27 mmol) is dissolved in 5 ml of dichloromethane in a 25 ml round-bottomed flask. The medium is cooled to 0° C. aid 0.45 ml of triethylamine (3.19 mmol) and then a solution of 6-(pyrrolidin-1-yl)pyridine-3-sulphonyl chloride (0.37 g, 1.53 mmol) in 3 ml of dichloromethane are added. The medium is stirred at 20° C. for 18 h. It is diluted with 50 ml of ethyl acetate, then washed with 20 ml of water and dried over magnesium sulphate. The slurry is filtered and the filtrate concentrated. The residue is purified on a column of silica (40 g, gradient $CH_2Cl_2$/AcOEt; 90:10 to 80:20).

1.13: (R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid methyl ester hydrochloride The methyl (2R)-2-[(3S)-2-oxo-3-(6-(pyrrolidin-1-yl)pyridin-3-ylsulphonylamino)pyrrolidin-1-yl]-3-(5-fluoro-1-(tritylamino)isoquinolin-6-yl)propanoate obtained above (0.7 g, 0.88 mmol) is dissolved in 5 ml of dichloromethane. The medium is cooled to 0° C. and 2 ml of a 4N solution of hydrochloric acid in dioxane are added. The medium is stirred at 20° C. for 18 h. It is concentrated to dryness and the residue is triturated from ether and filtered off. It is purified on a column of silica (40 g, gradient $CH_2Cl_2$/MeOH/$NH_4OH$; 100:0 to 90:10:0.5). The product thus obtained (300 mg, 76%) is dissolved in 5 ml of dichloromethane and salified with 0.5 ml of a 4N solution of hydrochloric acid in dioxane. The medium is concentrated and the residue is triturated from ether and dried over $P_2O_5$.

318 mg of a solid are obtained. Rf=0.33 ($CH_2Cl_2$/MeOH/$NH_4OH$; 90:10:0.5)
M.p.=115° C.
$[\alpha]_D^{20}$=−20° (c=0.15; MeOH).
$MH^+$=557.
$^1H$ NMR ($d_6$-DMSO, 200 MHz, δ ppm): 9.2 (b, 2H); 8.35 (m, 2H); 7.8 (m, 4H); 7.2 (d, 8.4 Hz, 1H); 6.55 (d, 8.4 Hz, 1H); 5.0 (dd, 10 and 4.2 Hz, 1H); 3.8 (m, 1H); 3.7 (s, 3H); 3.7-3.4 (m, 7H); 3.1 (m, 1H); 2.2 (m, 1H); 2.1 (m, 4H); 1.4 (m, 1H).

Example 2

(R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid ethyl ester hydrochloride (Compound No. 13)

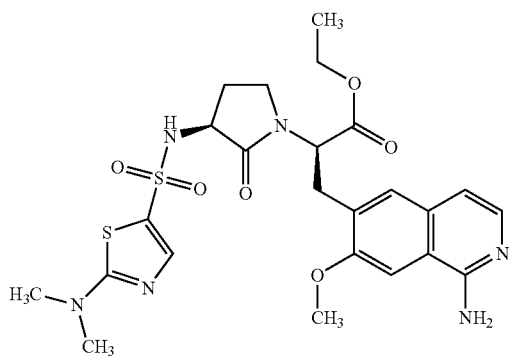 [SMILES: CCOC(=O)[C@@H](Cc1cc2ccnc(N)c2cc1OC)N1CC[C@H](NS(=O)(=O)c2cnc(N(C)C)s2)C1=O]

2.1: 3-(3-Bromo-4-methoxyphenyl) acrylic acid

3-Bromo-4-methoxybenzaldehyde (50 g, 232 mmol), malonic acid (36.3 g, 348 mmol) and 250 ml of anhydrous pyridine are introduced into a 500 ml round-bottomed flask. Piperidine (11.4 ml, 116 mmol) is added and the medium is brought to reflux for 3 h. The pyridine is removed under vacuum and the medium is run on to 500 ml of a 1M aqueous hydrochloric acid solution. The solid is filtered off, washed with water and dried over $P_2O_5$.

60 g of a white solid are obtained.

2.2: 6-Bromo-7-methoxy-2H-isoquinolin-1-one 3-(3-Bromo-4-methoxyphenyl)acrylic acid (59 g, 229 mmol) is suspended in 100 ml of toluene. 27.3 ml (344 mmol) of thionyl chloride are added and the medium is brought to reflux for 6 h. It is concentrated to dryness and a solid is obtained.

The acid chloride thus obtained is dissolved in 200 ml of dioxane and added, at 0° C., to a solution of sodium azide (28 g, 435 mmol) in 400 ml of a 50:50 mixture of dioxane and water. The medium is stirred for 2 h, diluted with 500 ml of water and extracted with 3×400 ml of ether. The organic phases are washed with a saturated aqueous sodium bicarbonate solution and a saturated aqueous sodium chloride solution and dried over $MgSO_4$. The slurry is filtered and the filtrate is concentrated to a volume of 100 ml at a temperature of less than 40° C. behind a protective screen. The residue comprising the acyl azide is added over 1 hour to a solution of tri(n-butyl)amine (52 ml, 217 mmol) in 750 ml of diphenyl ether at 250° C. The medium is maintained at 250° C. for 1 h after the addition. After cooling, it is run on to 1 litre of a cyclohexane/ethyl acetate mixture (90:10). The mixture is left standing for 18 h and filtered. The solid is washed with cyclohexane and then dried over $P_2O_5$.

44 g of a beige solid are obtained. Rf=0.35 ($CH_2Cl_2$/MeOH; 95:5).

2.3: 6-Bromo-1-chloro-7-methoxyisoquinoline

6-Bromo-7-methoxy-2H-isoquinolin-1-one (44 g, 173 mmol) is suspended in 50 ml of toluene and phosphoryl chloride (70 ml, 692 mmol, 4 eq.) is added. The medium is brought to 110° C. for 6 h. It is concentrated to dryness and then run on to 400 ml of ice. 400 ml of dichloromethane are added and neutralization is carried out with solid sodium bicarbonate. Extraction is carried out with 3×400 ml of dichloromethane and the organic phases are washed with a saturated aqueous sodium chloride solution and dried over $MgSO_4$. The slurry is filtered and the filtrate concentrated. The product is decoloured with animal charcoal in an ethyl acetate/toluene mixture (1:1).

31 g of a beige solid are obtained. Rf=0.46 (cyclohexane/ethyl acetate; 80:20).

2.4: 1-Amino-6-bromo-7-methoxyisoquinoline 12 g of 6-bromo-1-chloro-7-methoxyisoquinoline (44 mmol), 40 g (660 mmol, 15 eq.) of ammonium acetate and 62 g of phenol (660 mmol, 15 eq.) are introduced into a 250 ml round-bottomed flask. The medium is brought to 150° C. for 16 hours. After cooling, it is run on to 10N sodium hydroxide (200 ml) and extracted with dichloromethane (3×400 ml). The organic phases are washed with a saturated aqueous sodium chloride solution and dried over $Na_2SO_4$. The slurry is filtered and the filtrate concentrated. The product is purified by chromatography on silica gel (300 g, methanol/dichloromethane; 3:97 to 5:95).

9 g of a solid are obtained. Rf=0.13 (methanol/dichloromethane; 5:95).

2.5: (6-Bromo-7-methoxyisoquinolin-1-yl)tritylamine

1-Amino-6-bromo-7-methoxyisoquinoline (9 g, 35.5 mmol) and 35 ml of anhydrous DMF are introduced into a 100 ml round-bottomed flask. 6 ml of triethylamine (43 mmol) and then trityl chloride (10.9 g, 39 mmol) are added. The medium is brought to 50° C. for 16 h. After cooling, it is run on to a mixture of water and ethyl acetate (200 ml) and extracted with 3×150 ml of ethyl acetate. The organic phases are washed with a saturated aqueous sodium chloride solution and dried over $MgSO_4$. The slurry is filtered and the filtrate concentrated. The product is purified by chromatography on silica gel (300 g, ethyl acetate/cyclohexane; 10:90).

15 g of a solid are obtained. Rf=0.7 (cyclohexane/ethyl acetate; 90:10).

2.6: Ethyl (S)-2-(3-benzyloxycarbonylamino-2-oxopyrrolidin-1-yl)acrylate 18 g (77 mmol) of benzyl (S)-(2-oxopyrrolidin-3-yl)carbamate (J. W. Skiles et al., Bioorg. and Med. Chem., 1993, 3(4), 773) and 4 g (15 mmol) of triphenylphosphine are suspended in 50 ml of dichloromethane. A solution of ethyl propiolate (8.3 g, 84 mmol) in 50 ml of dichloromethane is added over 15 min. The medium is stirred at 20° C. for 4 h and then partially concentrated. The product is purified by chromatography on a column of silica (400 g) with a gradient of an ethyl acetate/dichloromethane mixture (from 10:90 to 20:80).

18 g of an oil are obtained. Rf=0.4 (MeOH/$CH_2Cl_2$; 5:95).

2.7: Ethyl Z-(S)-2-(3-benzyloxycarbonylamino-2-oxopyrrolidin-1-yl)-3-[7-methoxy-1-((triphenylmethyl)amino)isoquinolin-6-yl]acrylate 12.6 g (38 mmol) of ethyl (S)-2-(3-benzyloxycarbonylamino-2-oxopyrrolidin-1-yl)acrylate, obtained in 2.6, are reacted with 19 g (38 mmol) of (6-bromo-7-methoxyisoquinolin-1-yl)tritylamine, obtained in 2.5, according to a procedure identical to that described in 1.9. After chromatographing on silica gel (400 g, eluent: toluene/AcOEt; 90:10), 18 g of a yellow solid are obtained. Rf=0.39 (AcOEt/dichloromethane; 20:80).

2.8: Ethyl (2R)-2-((3S)-3-benzyloxycarbonylamino-2-oxopyrrolidin-1-yl)-3-[7-methoxy-1-((triphenylmethyl)amino)isoquinolin-6-yl]propanoate The compound obtained in 2.7 (18 g, 24 mmol) is suspended in 80 ml of ethyl acetate and 80 ml of ethanol in a 500 ml Parr bottle. The medium is degassed by sparging with nitrogen (30 min) and 800 mg (1.2 mmol) of (R,R)-(DuPhos)Rh(COD) triflate (Strem Chemicals Inc.) are added. The medium is placed under 50 psi of $H_2$ and stirred at 20° C. for 48 h. The medium is filtered and then concentrated, and the product is purified by chromatography on silica gel (400 g, gradient: toluene/AcOEt; 90:10 to 80:20).

14 g of the desired product are obtained. Rf=0.39 (AcOEt/dichloromethane; 20:80).

2.9: Ethyl (2R)-2-((3S)-3-amino-2-oxopyrrolidin-1-yl)-3-[7-methoxy-1-((triphenylmethyl)amino)isoquinolin-6-yl]propanoate The product obtained above in 2.8 (2 g, 2.6 mmol) is dissolved in 15 ml of ethanol. 200 mg of 10% Pd/C are added under $N_2$. The medium is placed under 3 atm. of hydrogen in a Parr device and stirred at 20° C. for 3 h. It is filtered through celite and concentrated to dryness.

1.49 g of a foam are obtained. Rf=0.2 ($CH_2Cl_2$/MeOH; 95:5)

2.10: Ethyl (2R)-2-[(3S)-3-(2-(dimethylamino)thiazol-5-ylsulphonylamino)-2-oxopyrrolidin-1-yl]-3-(7-methoxy-1-(tritylamino)isoquinolin-6-yl)propanoate Ethyl (2R)-2-((3S)-3-amino-2-oxopyrrolidin-1-yl)-3-[7-methoxy-1-((triphenylmethyl)amino)-isoquinolin-6-yl]propanoate (0.7 g, 1.14 mmol) is dissolved in 5 ml of dichloromethane in a 25 ml round-bottomed flask. The medium is cooled to 0° C. and 0.3 ml of diisopropylethylamine (1.7 mmol) and then a solution of 2-(dimethylamino)thiazole-5-sulphonyl chloride (0.26 g, 1.14 mmol in 3 ml of dichloromethane are added. The medium is stirred at 20° C. for 18 h. It is diluted with 50 ml of ethyl acetate, then washed with 20 ml of water and dried over magnesium sulphate. The slurry is filtered and the filtrate concentrated. The residue is purified on a column of silica (40 g, gradient $CH_2Cl_2$/AcOEt; 90:10 to 80:20).

0.5 g of a solid is obtained. Rf=0.59 ($CH_2Cl_2$/MeOH; 90:10)

2.11: (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid ethyl ester hydrochloride The ethyl (2R)-2-[(3S)-3-(2-(dimethylamino)thiazol-5-ylsulphonylamino)-2-oxopyrrolidin-1-yl]-3-(7-methoxy-1-(tritylamino)isoquinolin-6-yl)propanoate obtained above (0.35 g, 0.44 mmol) is dissolved in 5 ml of dichloromethane. The medium is cooled to 0° C. and 0.5 ml of a 4N solution of hydrochloric acid in dioxane is added. The medium is stirred at 20° C. for 18 h. It is concentrated to dryness and the residue is triturated from ether and filtered off. It is purified on a column of silica (40 g, gradient $CH_2Cl_2$/MeOH/$NH_4OH$; 100:0 to 90:10:0.5). The product thus obtained is dissolved in 5 ml of dichloromethane and salified with 0.5 ml of a 4N solution of hydrochloric acid in dioxane. The medium is concentrated and the residue is triturated from ether and dried over $P_2O_5$. 230 mg of a solid are obtained.

Rf=0.23 ($CH_2Cl_2$/MeOH; 95:5)

M.p.=175° C.

$[\alpha]_D^{20}$=+43° (c=0.1; MeOH).

$MH^+$=563.

$^1H$ NMR (($d_6$-DMSO, 200 MHz, δ ppm): 8.9 (b, 2H); 8.1 (m, 2H); 7.8 (s, 1H); 7.55 (m, 2H); 7.1 (d, 8.3 Hz, 1H); 5.1 (dd, 10 and 4.2 Hz, 1H); 4.1 (q, 7.9 Hz, 2H); 3.9 (s, 3H); 3.8 (m, 1H); 3.7-3.4 (m, 3H); 3.1 (m, 1H); 3.0 (s, 6H); 2.1 (m, 1H); 1.4 (m, 1H); 1.1 (t, 7.9 Hz, 3H).

Example 3

(R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid propyl ester hydrochloride (Compound N° 98)

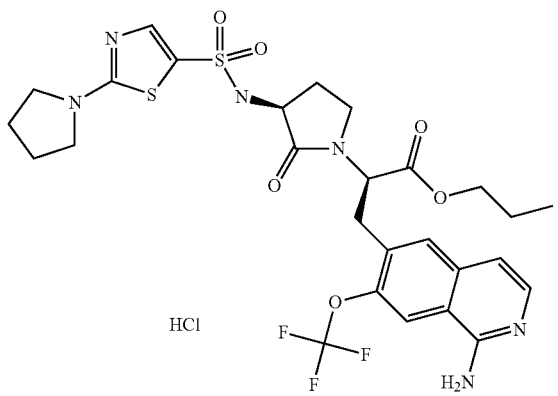 [SMILES: CCCOC(=O)[C@@H](Cc1cc2ccnc(N)c2cc1OC(F)(F)F)N1CC[C@H](NS(=O)(=O)c2cnc(N3CCCC3)s2)C1=O ; Cl]

3.1: 3-Bromo-4-trifluoromethoxy-benzaldehyde

To 68 g (0.36 mol) of 4-Trifluoromethoxybenzaldehyde dissolved in a mixture of 100 ml $CH_2Cl_2$, 100 ml TFA and 50 ml conc. $H_2SO_4$ are added within 7 h 130 g (0.72 mol) N-bromo-succinimide in small portions under stirring at room temperature (r.t.). The reaction mixture is stirred for 2 days at r.t.

The reaction mixture is poured on 1.2 l of an ice/water mixture. The resulting suspension is extracted three times with 500 ml $CH_2Cl_2$ and the combined organic phases are neutralized with 500 ml aqueous sat. $NaHCO_3$ solution. The organic phase is then dried with $Na_2SO_4$. After filtration of the drying agent the organic solvent is removed at a rotary evaporator under reduced pressure. After addition of 500 ml of a 1:1 mixture of n-pentane/ether, the precipitated succinimide is removed by filtration. The organic solvent is removed under reduced pressure and the remaining residue is purified by chromatography on silica gel (250 g, 0.04-0.063 mm, Merck) using ethylacetate/n-heptane=1/4 as mobile phase.

14 g of a solid are obtained.

$^1$H-NMR ($d_6$-DMSO, 600 MHz, δ ppm): 7.77 (d, J=8.1 Hz, 1 H), 8.05 (dd, J=8.1 Hz, 1.7 Hz, 1 H), 8.34 (d, J=1.7 Hz, 1 H), 10.01 (br s, 1 H)

3.2: (E)-3-(3-Bromo-4-trifluoromethoxy-phenyl)-acrylic acid

To a solution of 14 g (52 mmol) of the aldehyde prepared above in 50 ml abs. pyridine 7.0 g (67.6 mmol) malonic acid and 2.6 ml piperidine are added at r.t. subsequently under stirring. The reaction mixture is stirred for 2 h at 100° C.

After removal of the solvent under reduced pressure 100 ml water are added and the solution is acidified by addition of 2 N aq. HCl. The reaction product is isolated by filtration and dried in a drying cabinet under reduced pressure at 50° C.

14.6 g of a solid are obtained.

$^1$H-NMR (d6-DMSO, 500 MHz, δ ppm): =6.66 (d, J=16.1 Hz, 1 H), 7.56 (d, 1 H, J=8.6 Hz), 7.59 (d, 1 H, 16.1 Hz), 7.85 (dd, 1 H, J=8.6 Hz, 2.2 Hz), 8.22 (d, 1 H, J=2.2 Hz), 12.5 (br s, 1 H)

3.3: 6-Bromo-7-trifluoromethoxy-2H-isoquinolin-1-one

To 14 g (47 mmol) of (E)-3-(3-Bromo-4-trifluoromethoxy-phenyl)-acrylic acid, dissolved in 125 ml abs. Acetone, 7.8 ml (1.2 eq) $N(Et)_3$ in 8 ml acetone and 5.9 ml (1.3 eq) Chloroethylformiate in 6 ml acetone are subsequently added at 0° C. under mechanical stirring.

After stirring of the medium for 1 h at 0° C., 4.6 g (1.5 eq) $NaN_3$ dissolved in 20 ml water are added at this temperature. After stirring for an additional hour, the suspension is poured on 200 ml ice-cold water and extracted three times with 150 ml diethylether. After drying of the combined organic phases with $Na_2SO_4$, 80 ml of toluene are added and the diethylether is carefully removed at a rotary evaporator under reduced pressure.

The resulting solution is then added dropwise under Argon atmosphere to a solution of 11.2 ml (47 mmol) tri-n-butylamine in 100 ml diphenylether, heated to 250° C., while the toluene is continuously distilled off. After completion of the addition the reaction mixture was stirred for an additional hour at this temperature.

After completion of the reaction the solvent is removed by distillation under reduced pressure and the remaining residue poured into 200 ml of diethylether. This solution is extracted twice with 100 ml water. The organic phase is dried over $Na_2SO_4$ and after filtration of the slurry purified by chromatography on silica gel (40-63μ) using ethylacetate/heptane=2/1 as mobile phase resulting in 3.5 g of 6-Bromo-7-trifluoromethoxy-2H-isoquinolin-1-one.

$^1$H-NMR (d6-DMSO, 500 Mhz, δ ppm): 6.60 (d, 1 H, J=7.40 Hz), 7.31 (br d, 1 H, J=7.40 Hz), 8.10 (s, 1 H), 8.26 (s, 1 H), 11.62 (br s, 1 H)

3.4: 6-Bromo-1-chloro-7-trifluoromethoxy-2H-isoquinoline

To 3.5 g (11.4 mmol) of 6-Bromo-7-trifluoromethoxy-2H-isoquinolin-1-one in 50 ml abs. toluene 3.2 ml (34.2 mmol, 3 eq) $POCl_3$ are added under stirring at r.t.

The mixture is heated for 1 h under reflux. The reaction mixture is evaporated under reduced pressure and the remaining residue poured on ice-cold water (300 ml).

After neutralization with saturated aq. $NaHCO_3$ solution, the aqueous phase is extracted three times with 100 ml $CH_2Cl_2$. The combined organic phases are dried ($Na_2SO_4$). After filtration of the drying agent, the organic phase is evaporated under reduced pressure. 4 g of the expected compound are obtained.

$MH^+$: 327, 329

3.5: 6-Bromo-7-trifluoromethoxy-isoquinolin-1-yl-amine 4 g (12 mmol) of 6-Bromo-1-chloro-7-trifluoromethoxy-2H-isoquinoline are intermixed with 14 g acetamide (14 eq.) and 5 g (3 eq.) $K_2CO_3$. This mixture is heated for 1 h at 180° C. under stirring. The reaction mixture is stirred in ethylacetate (100 ml) and water (100 ml). The organic phase is separated, dried with Na$_2$SO$_4$ and the solvent removed under reduced pressure after filtration of the drying agent. For purification, a chromatography on silical gel (40-63µ, Merck) is performed with ethylacetate as mobile phase. 890 mg of a solid are obtained.

MH$^+$: 238, 240

3.6: (6-Bromo-7-trifluoromethoxy-isoquinolin-1-yl)-tritylamine

To 890 mg (2.9 mmol) 6-Bromo-7-trifluormethoxy-isoquinolin-1-yl-amine, dissolved in 15 ml abs. DMF 1.21 g (1.5 eq) tritylchloride and 803 µl (2 eq) triethylamine are added subsequently under stirring.

The reaction mixture is heated to 50° C. for 15 h. After removal of the solvent (oil pump vacuum) at a rotary evaporator, the remaining residue is dissolved with 50 ml CH$_2$Cl$_2$ and the organic phase extracted twice with 20 ml of water. After drying with Na$_2$SO$_4$, filtration of the drying agent and removal of the solvent under reduced pressure the raw material is purified by chromatography on silicagel (40-63µ) and n-heptane/ethylacetate=10/1 as mobile phase. 1.42 g of the expected compound are obtained.

MH$^+$: 549, 551

3.7: (E)-2-((S)-3-tert-Butoxycarbonylamino-2-oxo-pyrrolidin-1-yl)-3-[7-trifluoromethoxy-1-(trityl-amino)-isoquinolin-6-yl]-acrylic acid methyl ester 1.42 g (2.6 mmol) of 6-Bromo-7-trifluoromethoxy-isoquinolin-1-yl)-tritylamine are dissolved in 30 ml abs. DMF. Under stirring, 431 mg (2.6 mmol) tetraethyl-ammonium chloride, 655 mg (3 eq) NaHCO$_3$, 30 mg (0.05 eq) Pd-(II)-acetate and 812 mg (1.1 eq) of the coupling agent 2-((S)-3-tert-Butoxycarbonylamino-2-oxo-pyrrolidin-1-yl)-acrylic acid methyl ester are added at r.t. The solution is heated under stirring to 95° C. for 2 h.

After removal of the solvent under reduced pressure, the remaining residue is dissolved with CH$_2$Cl$_2$. The organic phase is extracted twice with water, dried with Na$_2$SO$_4$, filtrated and the solvent removed under reduced pressure. The crude product is purified by chromatography on silica gel (40-63µ), n-heptane/ethylacetate=1/1 as mobile phase. 1.35 g of the title compound are obtained (oil).

MH$^+$: 753.2

3.8: (R)-2-((S)-3-tert-Butoxycarbonylamino-2-oxo-pyrrolidin-1-yl)-3-[7-trifluoromethoxy-1-(trityl-amino)-isoquinolin-6-yl]-propionic acid methyl ester 1.35 g (1.8 mmol) of (E)-2-((S)-3-tert-Butoxycarbonylamino-2-oxo-pyrrolidin-1-yl)-3-[7-trifluoromethoxy-1-(trityl-amino)-isoquinolin-6-yl]acrylic acid methyl ester are dissolved in 50 ml abs. Methanol.

Under Argon atmosphere, 120 mg of R,R-Methyl-Duphos {(−)-1,2-Bis(2R,5R)-2,5-dimethylphospholano)benzene (cyclooctadiene) Rhodium (I)} catalyst are added. The reaction mixture is kept in an autoclave at 5 bar H$_2$ for 15 h at r.t.

The solvent is removed under reduced pressure and the reaction product purified by chromatography on silicagel (40-63µ) using n-heptane/ethylacetate=1/1 as mobile phase.

1.09 g of the product is isolated as a solid.

MH$^+$: 755.1

3.9: (R)-3-(1-Amino-7-trifluoromethoxy-isoquinolin-6-yl)-2-((S)-3-amino-2-oxo-pyrrolidin-1-yl)-propionic acid methyl ester bishydrochloride To 1.09 g (1.45 mmol) of (R)-2-((S)-3-tert-Butoxycarbonylamino-2-oxo-pyrrolidin-1-yl)-3-[7-trifluoromethoxy-1-(trityl-amino)-isoquinolin-6-yl]-propionic acid methyl ester, dissolved in 6 ml abs. CH$_2$Cl$_2$, 1.7 ml (6 eq) etheric HCl-solution are added at 0° C. The reaction mixture is stirred for 3 h at this temperature. After warming up to r.t., the solid product is isolated by filtration: 588 mg are obtained.

MH$^+$: 413.1

3.10: (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid methyl ester To a suspension of 485 mg (1 mmol) of (R)-3-(1-Amino-7-trifluoromethoxy-isoquinolin-6-yl)-2-((S)-3-amino-2-oxo-pyrrolidin-1-yl)-propionic acid methyl ester bishydrochloride in 6 ml CH$_2$Cl$_2$, 873 µl (5 mmol) diisopropylethylamine and 379 mg (1.5 mmol) 2-Pyrrolidin-1-yl-thiazole-5-sulfonyl chloride, dissolved in 5 ml CH$_2$Cl$_2$, are added subsequently at 0° C. under stirring.

The reaction mixture is stirred 12 h at r.t. For workup, the reaction mixture is diluted with 100 ml CH$_2$Cl$_2$ and the organic phase extracted three times with water.

After drying the organic phase with Na$_2$SO$_4$, filtration of the drying agent and removal of the solvent under reduced pressure, the raw material is purified by chromatography on silicagel (40-63µ) and CH$_2$Cl$_2$/Methanol=20/1 as mobile phase.

The resulting oil was crystallized from 20 ml pentane/diethylether (1:1): 330 mg are obtained.

MH$^+$: 603.3

3.11: (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid propyl ester To 57 mg (91 µmol) (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid methyl ester in 2 ml 1-propanol, 64.4 mg (227 µmol, 2.5 eq) titanium (IV)-isopropoxide are added.

The reaction mixture is heated for 2 h under reflux. The reaction mixture is then evaporated under reduced pressure and the resulting residue purified by chromatography on silicagel (40-63µ) using ethylacetate/methanol=20/1 as mobile phase: 55.8 mg are obtained.

3.12: (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid propyl ester hydrochloride

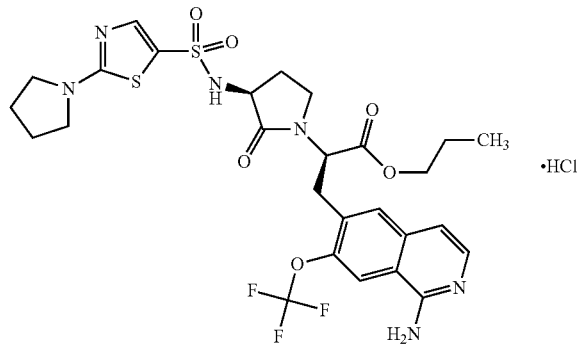 [SMILES: CCCOC(=O)[C@@H](Cc1cc2ccnc(N)c2cc1OC(F)(F)F)N1CC[C@H](NS(=O)(=O)c2cnc(N3CCCC3)s2)C1=O ; Cl]

After addition of 84 µl of a 1N aq. HCl solution (1 equivalent) to 55 mg (84 µmol) of the compound of 3.11 suspended in a 1:1 mixture of 3 ml acetonitrile/water, this suspension is lyophilized resulting in 49 mg of the hydrochloride as colorless foam.

MH$^+$: 657.2

$^1$H-NMR (d6-DMSO, 500 MHz, δ ppm): 0.83 (t, J=7.4 Hz, 3H), 1.56 (m, 2H), 1.58 (m, 1H), 1.99 (m, 4H), 2.21 (m, 1H), 3.20 (m, 1H), 3.28 (m, 1H), 3.39 (m, 4H), 3.46 (m, 1H), 3.49 (m, 1H), 4.04 (m, 2H), 4.98 (m, 1H), 7.20 (d, J=7.3 Hz, 1H), 7.56 (s, 1H), 7.74 (d, J=7.3 Hz, 1H), 8.00 (s, 1H), 8.02 (s, 1H), 8.62 (s, 1H), 9.28 (brs, 2H), 13.51 (brs, 1H)

Example 4

(R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid hydrochloride (Compound N° 96)

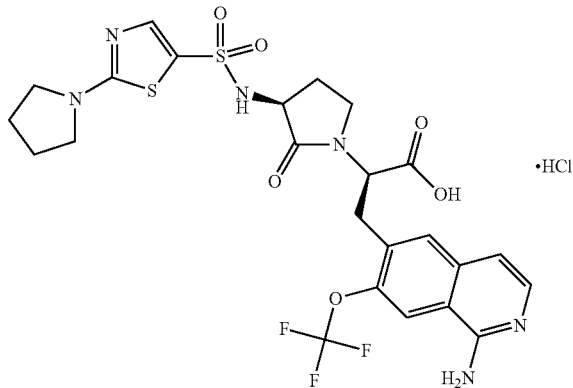 [SMILES: Nc1nccc2cc(C[C@H](C(=O)O)N3CC[C@H](NS(=O)(=O)c4cnc(N5CCCC5)s4)C3=O)c(OC(F)(F)F)cc12 ; Cl]

A solution of 600 mg (0.82 m.mole) of (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid propyl ester hydrochloride (compound of example 3) in 20 ml of 1N hydrochloric acid is heated at 80° C. for 4 h. The reaction mixture is evaporated to dryness. The crude material is taken up in acetone, and the precipitate formed is filtered, washed with acetone and dried under vacuum. 510 mg of a white powder containing 1.7 moles of HCl and 2 moles of $H_2O$ are collected (90% yield)

M.p.=256° C.

$^1$H-NMR (d6-DMSO, 400 MHz, δ ppm): 1.52 (m, 1H), 2.00 (m, 4H), 2.21 (m, 1H), 3.20-3.30 (brm, 2H), 3.40 (m, 4H), 3.45 (m, 2H), 3.8 (m, 1H), 4.90 (m, 1H), 7.20 (d, J=7.5 Hz, 1H), 7.59 (s, 1H), 7.78 (d, J=7.5 Hz, 1H), 8.00 (s, 1H), 8.02 (d, J=7.9 Hz, 1H), 8.62 (s, 1H), 9.30 (brs, 2H), 13.55 (brs, 1H)

Example 5

2-methoxyethyl (2R)-3-[1-amino-7-(trifluoromethoxy)isoquinolin-6-yl]-2-[(3S)-2-oxo-3-({[2-(pyrrolidin-1-yl)-1,3-thiazol-5-yl]sulfonyl}amino)pyrrolidin-1-yl]propanoate hydrochloride (Compound N° 106)

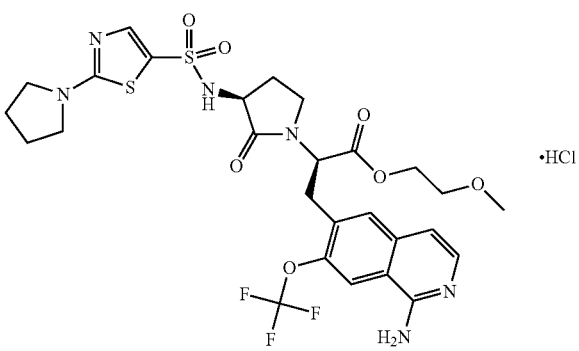 [SMILES: COCCOC(=O)[C@@H](Cc1cc2ccnc(N)c2cc1OC(F)(F)F)N1CC[C@H](NS(=O)(=O)c2cnc(N3CCCC3)s2)C1=O ; Cl]

To 100 mg (0.15 mmole) of [(2R)-3-[1-amino-7-(trifluoromethoxy)isoquinolin-6-yl]-2-[(3S)-2-oxo-3-({[2-(pyrrolidin-1-yl)-1,3-thiazol-5-yl]sulfonyl}amino)pyrrolidin-1-yl] propanoic acid] (compound of example 4) dissolved in 3 ml of 2-methoxyethanol, is added 32 µl (0.45 mmoles) of thionyl chloride at room temperature.

The reaction mixture is stirred at ambient temperature for 3 h, heated at 60° C. for 1 h and evaporated to dryness. The crude material is taken up in a saturated solution of sodium bicarbonate and extracted with Ethyl acetate. The organic phase is allowed to settle, washed with water, dried over sodium sulfate and evaporated to dryness. The white foam obtained is taken up in Ethyl Acetate and the resulting solution is treated with 2 equivalents of 1N hydrochloric acid in ether. Ether is again added and the precipitate formed is filtered, washed with ether and dried under vacuum. 75 mg (69% yield) of a white powder containing 2 moles of HCl and 1 mole of water are collected.

M.p.=154° C.

$^1$H-NMR (d6-DMSO, 400 MHz, δ ppm): 1.60 (m, 1H), 2.00 (m, 4H), 2.21 (m, 1H), 3.15-3.30 (brm, 2H), 3.20 (s, 3H), 3.40 (m, 4H), 3.42-3.55 (m, 4H), 3.80 (m, 1H), 4.2 (m, 2H), 5.00 (m, 1H), 7.20 (d, J=7.5 Hz, 1H), 7.59 (s, 1H), 7.72 (d, J=7.5 Hz, 1H), 8.00 (s, 1H), 8.05 (d, J=7.9 Hz, 1H), 8.62 (s, 1H), 9.30 (brs, 2H), 13.55 (brs, 1H)

Example 6

(R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 2,2-dimethyl-propionyloxymethyl ester (Compound N° 107)

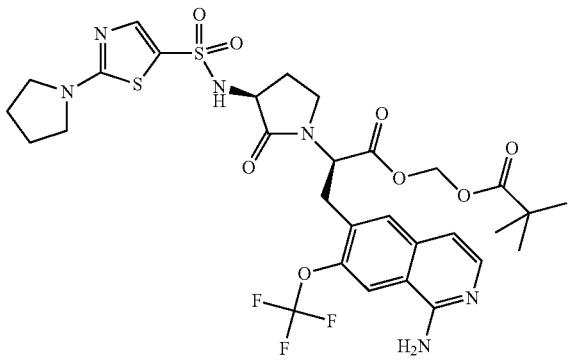 [SMILES: CC(C)(C)C(=O)OCOC(=O)[C@@H](Cc1cc2ccnc(N)c2cc1OC(F)(F)F)N1CC[C@H](NS(=O)(=O)c2cnc(N3CCCC3)s2)C1=O]

0.2 g of 4 Angstroms Molecular Sieves are activated for 1 h at 180° C. under reduced pressure. After cooling, 0.5 ml of an acetonitrile solution of 103 mg (0.15 mmol) of (2R)-3-[1-amino-7-(trifluoromethoxy) isoquinolin-6-yl]-2-[(3S)-2-oxo-3-({[2-(pyrrolidin-1-yl)-1,3-thiazol-5-yl]sulfonyl}amino)pyrrolidin-1-yl]propanoic acid hydrochloride (compound of example 4) and 58 mg (0.45 mmol) of diisopropylethylamine are added.

The solution is stirred for 1 h and room temperature and cooled down to 0° C. 37 mg (0.17 mmol) of chloromethyl 2,2-dimethylpropanoate are added and the reaction mixture is stirred at 45° C. for 7 h.

After dilution with 25 ml of Ethyl Acetate, the organic phase is washed with water, with saline, dried over sodium sulfate and evaporated to dryness. The crude solid is purified by column chromatography on silica gel using acetone as eluent. The resulting powder obtained after evaporation of collection fractions is taken up in a minimum amount of acetone (1 ml) and precipitated by addition of diisopropylether (10 ml). The precipitate is filtered, dried under vacuum. 40 mg of a white powder are obtained.

¹H-NMR (d6-DMSO, 400 MHz, δ ppm): 1.11 (9H, s); 1.55 (1H, m); 1.99 (4H, m); 2.17 (1H, m); 3.06-3.49 (8H, m); 3.79 (1H, m); 5.02 (1H, m); 5.73 (1H, d); 5.77 (1H, d); 6.88 (1H, d); 6.96 (2H, br); 7.56 (1H, s); 7.71 (1H, s); 7.83 (1H, d); 8.08 (1H, d); 8.20 (1H, br)

Example 7

(R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 1-cyclohexyloxy carbonyloxy-ethyl ester (Compound N° 108)

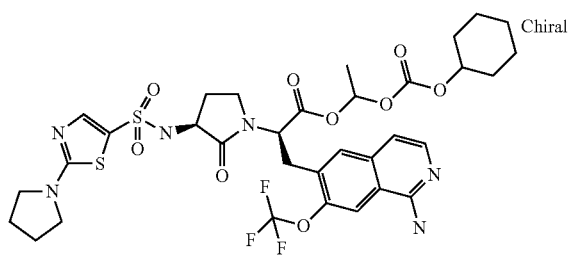 [SMILES: CC(OC(=O)OC1CCCCC1)OC(=O)[C@@H](Cc1cc2ccnc(N)c2cc1OC(F)(F)F)N1CC[C@H](NS(=O)(=O)c2cnc(N3CCCC3)s2)C1=O]

To a solution of (2R)-3-[1-amino-7-(trifluoromethoxy)isoquinolin-6-yl]-2-[(3S)-2-oxo-3-({[2-(pyrrolidin-1-yl)-1,3-thiazol-5-yl]sulfonyl}amino)pyrrolidin-1-yl]propanoic acid hydrochloride (compound of example 4) (0.13 g, 0.19 mmol) in anhydrous dimethylformamide (1 ml) were added diisopropyl ethyl amine (0.11 ml, 0.61 mmol) and carbonic acid 1-chloro-ethyl ester cyclohexyl ester (0.04 ml, 0.21 mmol). The reaction mixture was stirred at room temperature under nitrogen for 18 days, it was then concentrated under reduced pressure. The crude product was purified using a silica gel column chromatography (acetone/methylene chloride) to afford the title compound (0.021 g, 14%) as a white solid.

M.p.: 147° C.

¹H-NMR (d6-DMSO, 400 MHz, δ ppm): 1.1-1.7 (13 H, m), 1.75-1.89 (2 H, m), 1.92-2.05 (4 H, m), 2.1-2.25 (1 H, m), 3.05-3.25 (2 H, m), 3.4 (4 H, s), 3.42-3.55 (1 H, m), 3.7-3.9 (1 H, m), 4.55 (1 H, m), 4.9-5.1 (1 H, m), 6.63 (1 H, m), 6.87 (1 H, d, J=5.6 Hz), 6.94 (2 H, s), 7.56 (1 H, d, J=8 Hz), 7.7 (1 H, s), 7.83 (1 H, d, J=6 Hz), 8.1 (1 H, s), 8.2 (1 H, s).

Example 8

{[(cyclohexyloxy)carbonyl]oxy}methyl (2R)-3-[1-amino-7-(trifluoromethoxy)isoquinolin-6-yl]-2-[(3S)-2-oxo-3-({[2-(pyrrolidin-1-yl)-1,3-thiazol-5-yl]sulfonyl}amino)pyrrolidin-1-yl]propanoate (Compound No. 109)

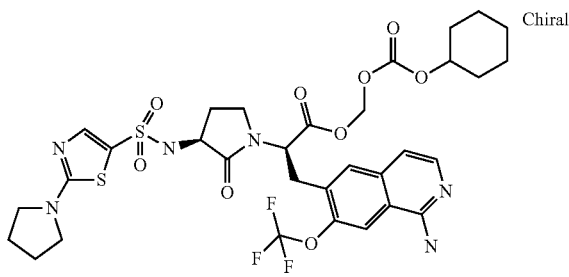 [SMILES: Nc1nccc2cc(C[C@H](C(=O)OCOC(=O)OC3CCCCC3)N3CC[C@H](NS(=O)(=O)c4cnc(N5CCCC5)s4)C3=O)c(OC(F)(F)F)cc12]

8.1 Chloromethyl Cyclohexyl Carbonate

At −78° C. under nitrogen, to a solution of cyclohexaiol (1 g, 10 mmol) in dichloromethane (20 ml), was added pyridine (0.82 ml, 10 mmol) and chloromethyl chloroformate (1.3 g, 10 mmol). The reaction mixture was stirred for 7 hours at 0° C. and at room temperature overnight and then poured on dichloromethane and washed with saturated aqueous ammonium chloride solution, the organic layer was dried over Na₂SO₄, filtered and concentrated under reduce pressure to give (1.6 g, 83%) of the title compound as a colorless oil, used without further purification, in the next step.

¹H-NMR (d6-DMSO, 300 MHz, δ ppm): 5.75 (2H, s); 4.75 (1H, m); 1.95 (2H, m); 1.80 (2H, m); 1.63-1.28 (6H, m).

8.2. {[(cyclohexyloxy)carbonyl]oxy}methyl (2R)-3-[1-amino-7-(trifluoromethoxy)isoquinolin-6-yl]-2-[(3S)-2-oxo-3-({[2-(pyrrolidin-1-yl)-1,3-thiazol-5-yl]sulfonyl}amino)pyrrolidin-1-yl]propanoate

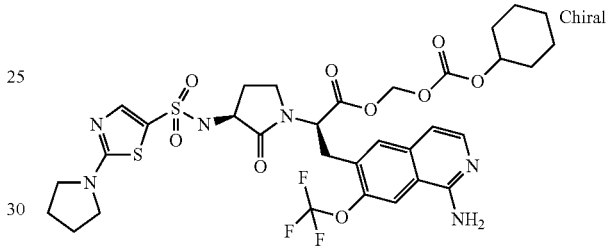

To a solution of (2R)-3-[1-amino-7-(trifluoromethoxy)isoquinolin-6-yl]-2-[(3S)-2-oxo-3-({[2-(pyrrolidin-1-yl)-1,3-thiazol-5-yl]sulfonyl}amino)pyrrolidin-1-yl]propanoic acid hydrochloride (compound of example 4) (0.5 g, 0.73 mmol) in anhydrous DMF (3 ml) were added potassium carbonate (0.3 g, 2.2 mmol) and chloromethyl cyclohexyl carbonate (0.21 g, 1.1 mmol), followed by potassium iodide (12 mg, 0.07 mmol). The reaction mixture was stirred at room temperature under nitrogen for 12 hours, and then was poured onto cold water, the resulting precipitate was filtered of, washed with water and dried under P₂O₅.

The crude product was purified using a silica gel column chromatography (acetone/methylene chloride) to afford the title compound (0.277 g, 49%) as a white solid.

MH+: 771

¹H-NMR (d6-DMSO, 400 MHz, δ ppm): 8.19 (1H, s); 8.08 (1H, d, 6.7 Hz); 7.83 (1H, d, 5.6 Hz); 7.71 (1H, s); 7.56 (1H, s); 6.94 (2H, s); 6.87 (1H, d, 5.8 Hz); 5.72 (2H, m); 5.03 (1H, m); 4.57 (1H, m); 3.88 (1H, m); 3.49-3.28 (6H, m); 3.22 (1H, m); 3.07 (1H, m); 2.16 (1H, m); 1.99 (4H, m); 1.82 (2H, m); 1.64 (2H, m); 1.59-1.17 (7H, m).

The chemical structures and the physical properties of a few examples of compounds according to the invention corresponding to the formula (I), in which the stereochemistry of the carbon identified by *1 is (R) and that of the carbon identified by *2 is (S), are illustrated in the following table.

In this table, "Me", "Et", "n-Pr", "i-Pr", "n-Bu", "i-Bu", "c-C₃H₅", "c-C₄H₇" and "c-C₅H₉" respectively represent methyl, ethyl, n-propyl, isopropyl, n-butyl, iso-butyl, cyclopropyl, cyclobutyl and cyclopentyl groups and, in the "Salt" column, HCl represents a compound in the hydrochloride form and CF₃CO₂H represents a compound in the trifluoroacetate form.

TABLE
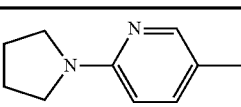
(Ia)
| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 1 |  | HCl | COOH | 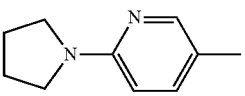 | 224 | B; 4.1<br>543 | −81<br>(0.35,<br>MeOH) |
| 2 | 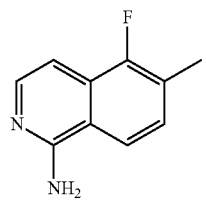 | HCl | COOMe | 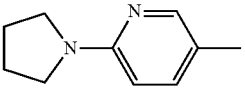 | 115 | B; 6.46<br>557 | −20<br>(0.125,<br>MeOH) |
| 3 | 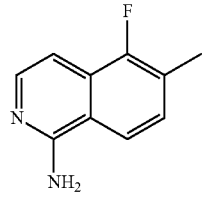 | HCl | COOEt | 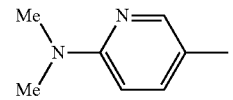 | 134 | A; 5.6<br>571 | +4<br>(0.1,<br>MeOH) |
| 4 | 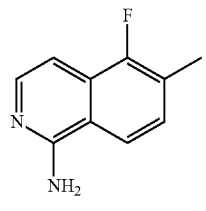 | HCl | COOH | 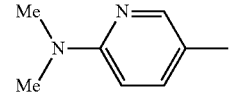 | >250 | B; 3.7<br>517 | −42<br>(0.165,<br>MeOH) |
| 5 | 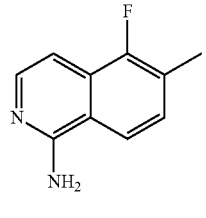 | HCl | COOMe | 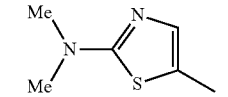 | 217 | B; 6.04<br>531 | −7.6<br>(0.145,<br>MeOH) |
| 6 | 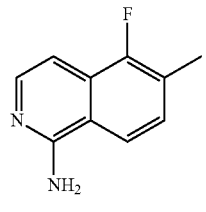 | HCl | COOH |  | 260 | A; 4.9<br>523 | +12<br>(0.28,<br>MeOH) |

TABLE-continued
(Ia)
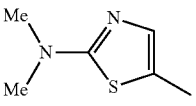
| N° | R₃ | Sel | COOR₁ | Q | Melting point (°C.) | LC/MS method; ret. Time (min.) Obs. MH⁺ | $[\alpha]_D^{20}$ (°) (c, solvent) |
|---|---|---|---|---|---|---|---|
| 7 | 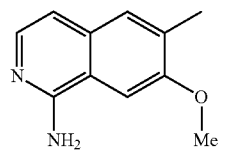 | HCl | COOH | 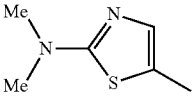 | 253 | A; 5.1 535 | +35 (0.1, MeOH) |
| 8 | 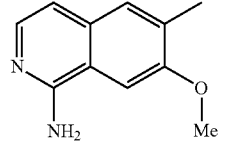 | HCl | COOi-Bu | 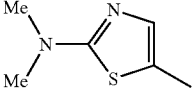 | 212 | A; 7.0 591 | +25 (0.1, MeOH |
| 9 | 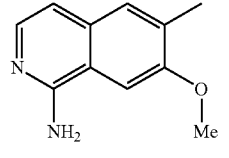 | HCl | COOCH₂—cC₃H₅ | 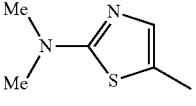 | 214 | B; 7.1 589 | +59 (0.1, MeOH) |
| 10 | 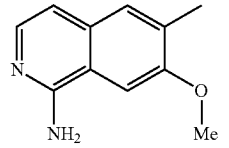 | HCl | COOCH₂—cC₄H₇ | 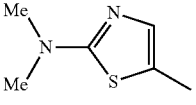 | 106 | A; 5.4 603 | +38 (0.1, MeOH) |
| 11 | 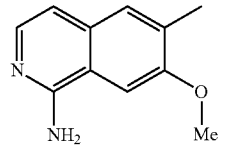 | HCl | COOi-Pr | 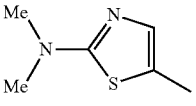 | 205 (dec.) | B; 7.2 577 | +34 (0.1, MeOH) |
| 12 | 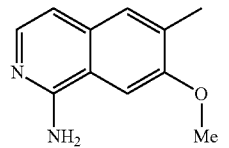 | HCl | COOc—C₅H₉ | 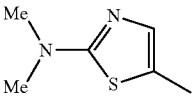 | 120 | A; 5.9 603 | +8 (0.1, MeOH) |
| 13 | 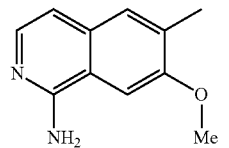 | HCl | COOEt | | 175 | B; 6.2 563 | +43 (0.1, MeOH) |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 14 | pyrrolidinyl-(5-methylthiazol-2-yl) | HCl | COOH | 1-amino-6-methyl-7-methoxy-isoquinolinyl | 278 | A; 5.4 561 | +18 (0.1, MeOH) |
| 15 | pyrrolidinyl-(5-methylthiazol-2-yl) | HCl | COOCH₂—cC₃H₅ | 1-amino-6-methyl-7-methoxy-isoquinolinyl | 186 | A; 6.7 615 | +51 (0.1, MeOH) |
| 16 | pyrrolidinyl-(5-methylthiazol-2-yl) | HCl | COOEt | 1-amino-6-methyl-7-methoxy-isoquinolinyl | 170 | A; 6.3 589 | +19 (0.1, MeOH) |
| 17 | 3,3-difluoropyrrolidinyl-(5-methylthiazol-2-yl) | HCl | COOH | 1-amino-6-methyl-7-methoxy-isoquinolinyl | 218 | A; 5.7 597 | +27 (0.1, MeOH) |
| 18 | 3,3-difluoropyrrolidinyl-(5-methylthiazol-2-yl) | HCl | COOEt | 1-amino-6-methyl-7-methoxy-isoquinolinyl | 215 | B; 7.4 625 | +40 (0.1, MeOH) |
| 19 | 3,3-difluoropyrrolidinyl-(5-methylthiazol-2-yl) | HCl | COOCH₂—cC₃H₅ | 1-amino-6-methyl-7-methoxy-isoquinolinyl | 190 | B; 8.0 651 | +40 (0.2, MeOH) |
| 20 | 3,3-difluoropyrrolidinyl-(5-methylthiazol-2-yl) | HCl | COOi-Pr | 1-amino-6-methyl-7-methoxy-isoquinolinyl | 185 (dec) | B; 8.0 639 | +36 (0.1, MeOH) |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvent) |
|---|---|---|---|---|---|---|---|
| 21 | (3S)-3-fluoropyrrolidin-1-yl 5-methylthiazol-2-yl | HCl | COOH | 1-amino-7-methoxy-6-methylisoquinolin-3-yl | 250 | A; 5.3 579 | +24 (0.1, MeOH) |
| 22 | N,N,3,5-tetramethylpyridin-2-amine | HCl | COOH | 1-amino-7-methoxy-6-methylisoquinolin-3-yl | 195 (dec) | A; 8.5 543 | −8 (0.1, MeOH) |
| 23 | N,N,3,5-tetramethylpyridin-2-amine | HCl | COOEt | 1-amino-7-methoxy-6-methylisoquinolin-3-yl | 123 (dec) | C; 0.98 571 | −13 (0.1, MeOH) |
| 24 | N,N,5-trimethylpyridin-2-amine | HCl | COOH | 1-amino-7-methoxy-6-methylisoquinolin-3-yl | 245 (dec) | B; 4.3 529 | −20 (0.1, MeOH) |
| 25 | N,N,5-trimethylpyridin-2-amine | HCl | COOEt | 1-amino-7-methoxy-6-methylisoquinolin-3-yl | 118 (dec) | A; 6.3 557 | −4 (0.1, MeOH) |
| 26 | 3-chloro-N,N,5-trimethylpyridin-2-amine | HCl | COOH | 1-amino-7-methoxy-6-methylisoquinolin-3-yl | 245 (dec) | A; 5 563 | −20 (0.1, MeOH) |
| 27 | 3-chloro-N,N,5-trimethylpyridin-2-amine | HCl | COOEt | 1-amino-7-methoxy-6-methylisoquinolin-3-yl | 225 (dec) | B; — 591 | −11 (0.1, MeOH) |
| 28 | N,N-dimethyl-5-methylthiazol-2-amine | HCl | COOH | 1-amino-6,7-dimethylisoquinolin-3-yl | 195 | B; 3.7 519 | +38 (0.1, MeOH) |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 29 | pyrrolidin-1-yl-(5-methylthiazol-2-yl) | HCl | COOH | 1-amino-6,7-dimethylisoquinolin-... | 179 | A; 5.2 545 | +28 (0.1, MeOH) |
| 30 | N,N-dimethyl-(5-methylthiazol-2-yl)amine | HCl | COOH | 1-amino-6-methyl-7-ethylisoquinolin-... | 178 | A; 4.9 533 | +29 (0.1, MeOH) |
| 31 | N,N-dimethyl-(5-methylthiazol-2-yl)amine | HCl | COOEt | 1-amino-6-methyl-7-ethylisoquinolin-... | 187 | A; 6.2 561 | +30 (0.1, MeOH) |
| 32 | pyrrolidin-1-yl-(5-methylthiazol-2-yl) | HCl | COOH | 1-amino-6-methyl-7-ethylisoquinolin-... | 254 (dec) | A; 4.9 559 | +17 (0.1, MeOH) |
| 33 | pyrrolidin-1-yl-(5-methylthiazol-2-yl) | HCl | COOEt | 1-amino-6-methyl-7-ethylisoquinolin-... | 183 | A; 6.5 587 | +17 (0.1, MeOH) |
| 34 | N,N-dimethyl-(5-methylpyridin-2-yl)amine | HCl | COOH | 1-amino-6-methyl-7-ethylisoquinolin-... | 195 | A; 4.6 527 | +36 (0.1, MeOH) |
| 35 | N,N-dimethyl-(5-methylpyridin-2-yl)amine | HCl | COOEt | 1-amino-6-methyl-7-ethylisoquinolin-... | 187 | A; 5.6 555 | +8 (0.1, MeOH) |

TABLE-continued
(Ia)
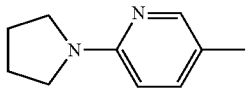
| N° | R₃ | Sel | COOR₁ | Q | Melting point (°C.) | LC/MS method; ret. Time (min.) Obs. MH⁺ | $[\alpha]_D^{20}$ (°) (c, solvent) |
|---|---|---|---|---|---|---|---|
| 36 | 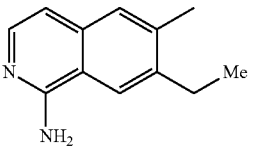 | HCl | COOH | 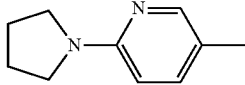 | 165 (dec) | A; 4.7 553 | +42 (0.1, MeOH) |
| 37 | 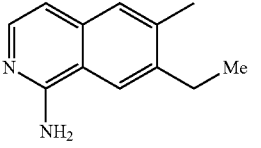 | HCl | COOEt | 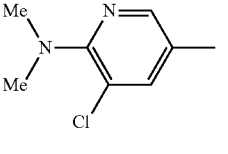 | 217 | A; 5.6 581 | +43 (0.1, MeOH) |
| 38 | 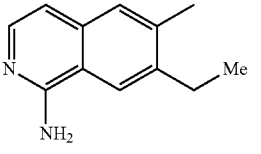 | HCl | COOH | 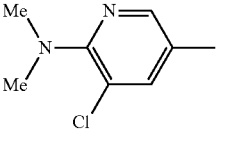 | 223 | A; 5.3 561 | — (0.1, MeOH) |
| 39 | 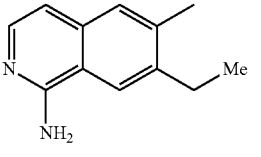 | HCl | COOEt | 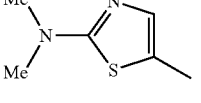 | 155 | B; — 589 | — (0.1, MeOH) |
| 40 | 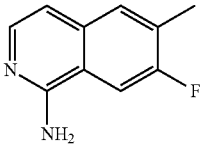 | HCl | COOH | 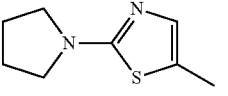 | 270 | A; 4.8 523 | +38 (0.1, MeOH) |
| 41 | 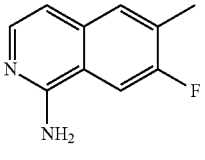 | HCl | COOH | 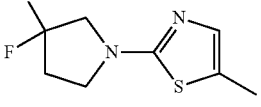 | 268 | A; 5.1 549 | +14 (0.1, MeOH) |
| 42 | 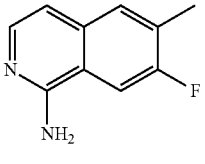 | HCl | COOH | 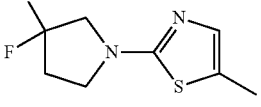 | 190 | B; 4.2 585 | +15 (0.1, MeOH) |

TABLE-continued
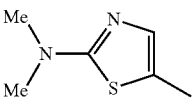
(Ia)
| N° | R₃ | Sel | COOR₁ | Q | Melting point (°C.) | LC/MS method; ret. Time (min.) Obs. MH⁺ | $[\alpha]_D^{20}$ (°) (c, solvent) |
|---|---|---|---|---|---|---|---|
| 43 | 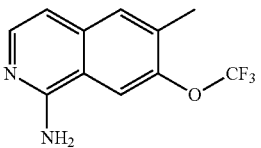 | HCl | COOMe | 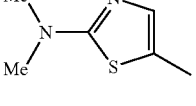 | 140 | A; 4.7<br>603 | +42<br>(0.1, MeOH) |
| 44 | 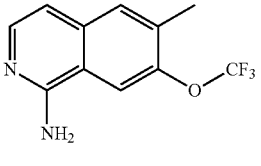 | HCl | COOH | 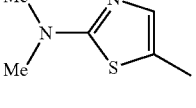 | 262 | B; 4.8<br>589 | +17<br>(0.1, MeOH) |
| 45 | 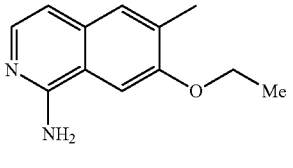 | HCl | COOH | 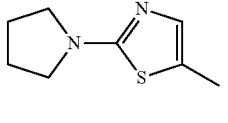 | 240 | A; 4.0<br>549 | +19<br>(0.1, MeOH) |
| 46 | 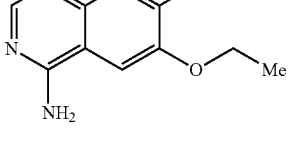 | HCl | COOH | 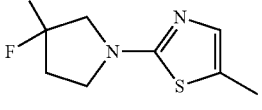 | 261 | B; 4.4<br>575 | +40<br>(0.1, MeOH) |
| 47 | 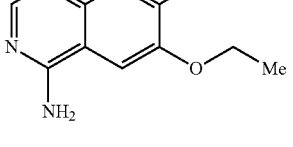 | HCl | COOH | 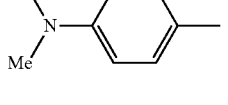 | 267 | A; 4.6<br>611 | +45<br>(0.1, MeOH) |
| 48 | 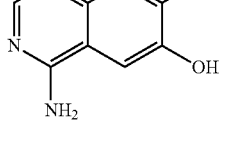 | HCl | COOH | 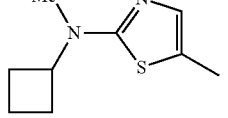 | 212 | B; 4.9<br>515 | −57<br>(0.28, MeOH) |
| 49 | 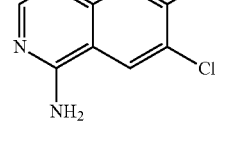 | HCl | COOH | 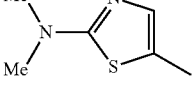 | Amorphous | D; 1.17<br>579 | — |
| 50 | 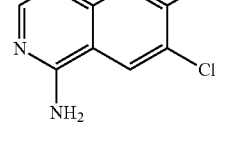 | HCl | COOH | | 250 (dec.) | E; 1.19<br>599 | |

TABLE-continued
(Ia)
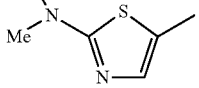
| N° | R₃ | Sel | COOR₁ | Q | Melting point (°C.) | LC/MS method; ret. Time (min.) Obs. MH⁺ | $[\alpha]_D^{20}$ (°) (c, solvent) |
|---|---|---|---|---|---|---|---|
| 51 | 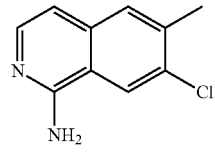 | HCl | COOMe | 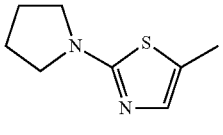 | Amorphous | D; 1.15 553 | — |
| 52 | 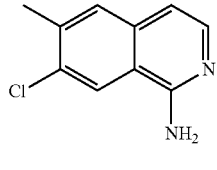 | HCl | COOMe | 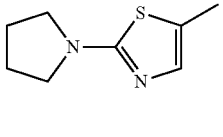 | Amorphous | D; 1.19 579 | — |
| 53 | 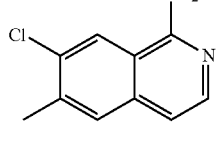 | HCl | COOH | 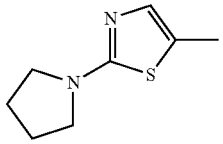 | Amorphous | D; 1.01 565 | — |
| 54 | 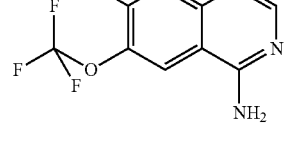 | HCl | COOMe | 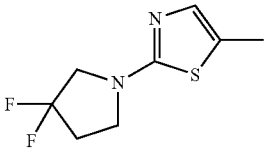 | Amorphous | D; 1.25 629 | — |
| 55 | 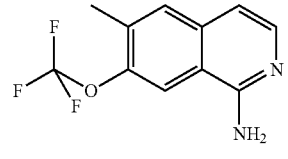 | HCl | COOMe | 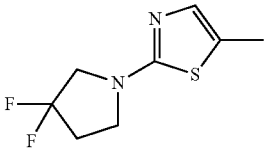 | Amorphous | E; 1.33 665 | — |
| 56 | 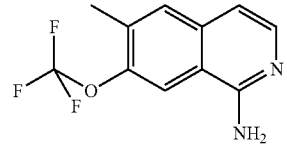 | HCl | COOH | 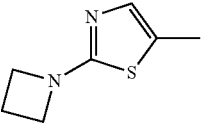 | Amorphous | E; 1.25 651 | — |
| 57 | 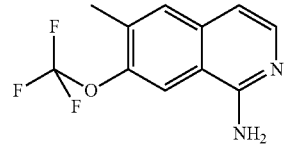 | HCl | COOMe | | Amorphous | E; 1.23 615 | — |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 58 | 2-(azetidin-1-yl)-5-methylthiazol-4-yl | HCl | COOH | 1-amino-6-methyl-7-(trifluoromethoxy)isoquinolin-3-yl | Amorphous | E; 1.09 601 | — |
| 59 | 6-(dimethylamino)-3-methylpyridin-2-yl | HCl | COOMe | 1-amino-6-methyl-7-(trifluoromethoxy)isoquinolin-3-yl | Amorphous | E; 1.09 597 | — |
| 60 | 6-(dimethylamino)-3-methylpyridin-2-yl | HCl | COOH | 1-amino-6-methyl-7-(trifluoromethoxy)isoquinolin-3-yl | Amorphous | E; 1.0 583 | — |
| 61 | 6-(dimethylamino)-3-methylpyridin-2-yl | HCl | COOMe | 1-amino-7-chloro-6-methylisoquinolin-3-yl | Amorphous | E; 1.01 547 | — |
| 62 | 6-(dimethylamino)-3-methylpyridin-2-yl | HCl | COOH | 1-amino-7-chloro-6-methylisoquinolin-3-yl | Amorphous | E; 0.86 533 | — |
| 63 | 6-(dimethylamino)-3-methylpyridin-2-yl | HCl | COOH | 1-amino-7-fluoro-6-methylisoquinolin-3-yl | ND | E; 0.79 517 | — |
| 64 | 6-(dimethylamino)-3-methylpyridin-2-yl | HCl | COOMe | 1-amino-7-fluoro-6-methylisoquinolin-3-yl | ND | D; 0.97 531 | — |

TABLE-continued

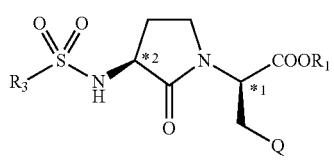
(Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 65 | 3,3-difluoropyrrolidinyl-5-methylthiazole | HCl | COOMe | 7-chloro-6-methyl-1-aminoisoquinoline | ND | E; 1.23 615 | — |
| 66 | 3,3-difluoropyrrolidinyl-5-methylthiazole | HCl | COOH | 7-chloro-6-methyl-1-aminoisoquinoline | 250 (dec.) | D; 1.17 601 | — |
| 67 | 2-(dimethylamino)-3-chloro-5-methylpyridine | HCl | COOMe | 7-fluoro-6-methyl-1-aminoisoquinoline | ND | D; 1.39 565 | — |
| 68 | 2-(dimethylamino)-3-chloro-5-methylpyridine | HCl | COOH | 7-fluoro-6-methyl-1-aminoisoquinoline | ND | D; 1.18 551 | — |
| 69 | 2-(dimethylamino)-3-chloro-5-methylpyridine | HCl | COOMe | 7-chloro-6-methyl-1-aminoisoquinoline | Amorphous | E; 1.29 581 | — |
| 70 | 2-(dimethylamino)-3-chloro-5-methylpyridine | HCl | COOH | 7-chloro-6-methyl-1-aminoisoquinoline | 250 (dec.) | E; 1.16 567 | — |
| 71 | 2-(dimethylamino)-3,5-dimethylpyridine | HCl | COOMe | 7-fluoro-6-methyl-1-aminoisoquinoline | ND | E; 1.05 545 | — |

TABLE-continued
(Ia)
| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 72 | 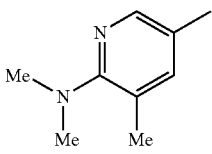 | HCl | COOMe | 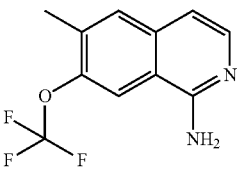 | Amorphous | E; 1.12 611 | — |
| 73 | 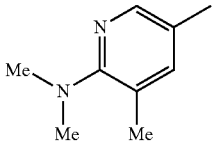 | HCl | COOH | 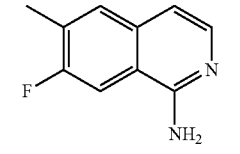 | ND | E; 0.82 531 | — |
| 74 | 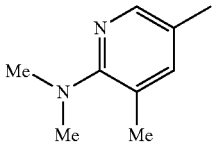 | HCl | COOH | 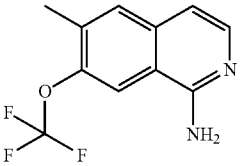 | 230 (dec.) | E; 0.99 597 | — |
| 75 | 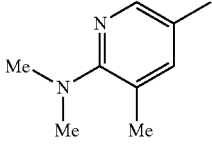 | HCl | COOMe | 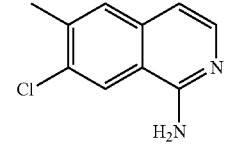 | ND | E; 1.12 561 | — |
| 76 | 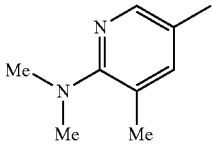 | HCl | COOH | 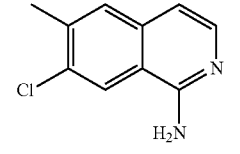 | ND | D; 2.1 547 | — |
| 77 | 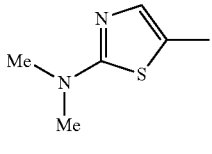 | HCl | COOMe | 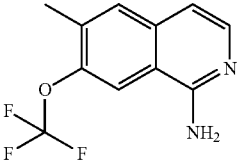 | 200 (dec.) | D; 1.18 603 | — |
| 78 | 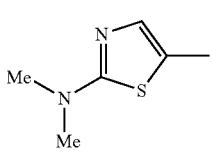 | HCl | COOMe | 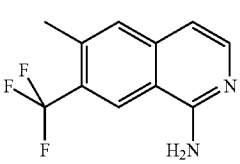 | ND | E; 1.16 587 | — |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 79 | Me-N(Me)-thiazole-Me | HCl | COOH | 6-Me,7-CF₃ isoquinolin-1-amine | ND | E; 1.01 573 | — |
| 80 | pyrrolidinyl-thiazole-Me | HCl | COOMe | 6-Me,7-CF₃ isoquinolin-1-amine | ND | F; 2.44 613 | — |
| 81 | pyrrolidinyl-thiazole-Me | HCl | COOH | 6-Me,7-CF₃ isoquinolin-1-amine | ND | G; 2.35 599 | — |
| 82 | Me-N(Me)-pyridine-Me | HCl | COOMe | 6-Me,7-CF₃ isoquinolin-1-amine | ND | F; 2.19 581 | — |
| 83 | Me-N(Me)-pyridine-Me | HCl | COOH | 6-Me,7-CF₃ isoquinolin-1-amine | ND | F; 1.96 567 | — |
| 84 | pyrrolidinyl-thiazole-Me | HCl | COOEt | 6-Me,7-Cl isoquinolin-1-amine | ND | F; 2.45 593 | — |
| 85 | azetidinyl-thiazole-Me | HCl | COOMe | 6-Me,7-Cl isoquinolin-1-amine | ND | F; 2.26 565 | — |
| 86 | Cl, Me-N(Me)-pyridine-Me | HCl | COOMe | 6-Me,7-OCF₃ isoquinolin-1-amine | ND | G; 2.84 631 | — |

TABLE-continued
(Ia)
| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 87 | 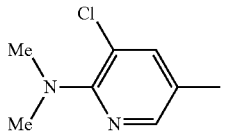 | HCl | COOH | 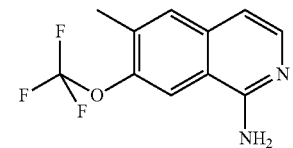 | ND | G; 2.67 617 | — |
| 88 | 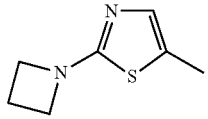 | HCl | COOMe | 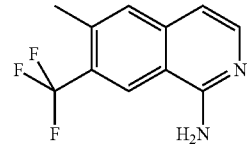 | ND | G; 2.6 599 | — |
| 89 | 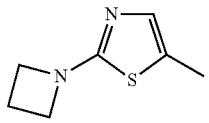 | HCl | COOH | 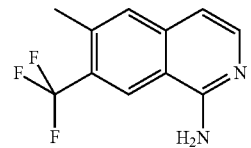 | ND | F; 2.09 585 | — |
| 90 | 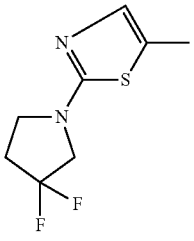 | HCl | COOMe | 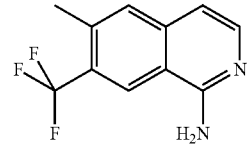 | ND | F; 2.6 649 | — |
| 91 | 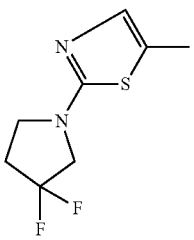 | HCl | COOH | 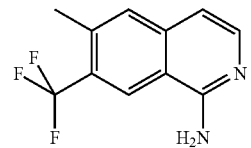 | ND | G; 2.5 634 | — |
| 92 | 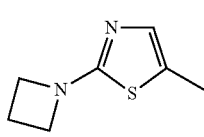 | HCl | COOH | 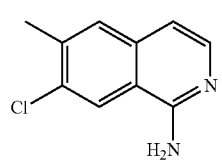 | ND | G; 2.2 551 | — |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 93 | 2-pyrrolidinyl-5-methylthiazole | HCl | COOn-Bu | 7-chloro-6-methyl-1-aminoisoquinoline | ND | F; 3.17 621 | — |
| 94 | 2-pyrrolidinyl-5-methylthiazole | HCl | COOMe | 7-cyano-6-methyl-1-aminoisoquinoline | ND | F; 2.34 570 | — |
| 95 | 2-pyrrolidinyl-5-methylthiazole | HCl | COOH | 7-cyano-6-methyl-1-aminoisoquinoline | ND | F; 2.15 556 | — |
| 96 | 2-pyrrolidinyl-5-methylthiazole | HCl | COOH | 7-trifluoromethoxy-6-methyl-1-aminoisoquinoline | 256 | D; 1.11 615 | — |
| 97 | 2-pyrrolidinyl-5-methylthiazole | HCl | COOEt | 7-trifluoromethoxy-6-methyl-1-aminoisoquinoline | ND | F; 2.65 643 | — |
| 98 | 2-pyrrolidinyl-5-methylthiazole | HCl | COOn-Pr | 7-trifluoromethoxy-6-methyl-1-aminoisoquinoline | ND | F; 2.93 657 | — |
| 99 | 2-pyrrolidinyl-5-methylthiazole | HCl | COO-CH₂-cyclopropyl | 7-trifluoromethoxy-6-methyl-1-aminoisoquinoline | ND | F; 2.97 669 | — |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvent) |
|---|---|---|---|---|---|---|---|
| 100 | pyrrolidine-thiazole-Me | HCl | COOn-Bu | 6-Me,7-OCF₃ isoquinolin-1-amine | ND | F; 2.67 / 671 | |
| 101 | pyrrolidine-thiazole-Me | HCl | COOi-Pr | 6-Me,7-OCF₃ isoquinolin-1-amine | ND | F; 1.97 / 657 | |
| 102 | Me₂N-thiazole-Me | HCl | COOEt | 6-Me,7-O(CH₂)₂OMe isoquinolin-1-amine | 108 | A; 5.4 / 657 | +6 (0.13, MeOH) |
| 103 | Me₂N-thiazole-Me | HCl | COOH | 6-Me,7-O(CH₂)₂OMe isoquinolin-1-amine | 180 | A; 4.7 / 579 | +3 (0.1, MeOH) |
| 104 | pyrrolidine-pyridine-Me | HCl | COOH | 3,6-diMe,5-F isoquinolin-1-amine | 217 | B; 4.4 / 557 | −50 (0.3, MeOH) |
| 105 | pyrrolidine-pyridine-Me | HCl | COOMe | 3,6-diMe,5-F isoquinolin-1-amine | 205 | B; 6.5 / 571 | −68 (0.35, MeOH) |
| 106 | pyrrolidine-thiazole-Me | | COO(CH₂)₂OMe | 6-Me,7-OCF₃ isoquinolin-1-amine | 154 | B; 5.78 / 673 | — |

TABLE-continued (Ia)

| N° | R₃ | Sel | COOR₁ | Q | Melting point (°C.) | LC/MS method; ret. Time (min.) Obs. MH⁺ | $[\alpha]_D^{20}$ (°) (c, solvant) |
|---|---|---|---|---|---|---|---|
| 107 | 4-methylthiazol-2-yl-pyrrolidine | | pivaloyloxymethyl ester | 1-amino-6-methyl-7-(trifluoromethoxy)isoquinoline | | B; 6.7 729 | |
| 108 | 4-methylthiazol-2-yl-pyrrolidine | | (1-(cyclohexylacetoxy)ethyl) ester | 1-amino-6-methyl-7-(trifluoromethoxy)isoquinoline | 147 | B; 7.2 785 | |
| 109 | 4-methylthiazol-2-yl-pyrrolidine | | (cyclohexyloxycarbonyloxy)methyl ester | 1-amino-6-methyl-7-(trifluoromethoxy)isoquinoline | | B; 7.03 571 | |
| 110 | 4-methylthiazol-2-yl-pyrrolidine | | (methoxymethoxy)carbonyl ester | 1-amino-6-methyl-7-(trifluoromethoxy)isoquinoline | | H; 13.48 659 | |

The compounds according to the invention have formed the object of pharmacological assays which make it possible to determine their anticoagulant and antithrombotic activities.

Determination of the IC$_{50}$ with Regard to Factor IXa (In Vitro)

The compounds according to the invention are tested in a range of concentrations (4.9 nM to 5 μM final) and deposited in a proportion of 25 μl per well. After the deposition of 50 μl of Spectrozyme 229 substrate (American Diagnostica), at the final concentration of 625 μM, the reaction is triggered by the addition of 25 μl of FIXa (human factor IXa supplied by Enzyme Research Laboratories (ERL)), at the final concentration of 2.5 U/ml. Reading is carried out at 405 nm for 15 min at 37° C. The percentage of inhibition of enzymatic activity (expressed as maximum rate of cleavage of the substrate) is calculated with respect to the enzymatic activity in the absence of inhibitor. The curve of inhibition as a function of the concentrations makes it possible to determine the IC$_{50}$ of each compound (that is to say, the concentration necessary in order to obtain 50% inhibition of the enzymatic activity) or the percentage inhibition at the maximum concentration tested (5 μM).

Determination of the IC$_{50}$ with Regard to Factor Xa (In Vitro)

The compounds according to the invention are tested in a range of concentrations (10 pM to 10 μM final) in assay buffer (50 mM TRIS, 100 mM NaCl, 0.1% BSA, pH 7.5) with 0.1% maximal final DMSO concentration and deposited in a proportion of 25 μl per well, on 25 μL enzyme (human coagulation factor Xa: Enzyme Research Laboratories HFXa, final concentration 0.003 UI/ml). The reactive were mixed, centrifuged and incubated 10 minutes at 37° C. in a 96 well microtiter plate. The enzyme reaction was started with 50 μL substrate (S-2765, Biogenic ref 821413 in a final concentration of 62.5 μM final). The time course of the reaction was monitored at 405 nm in a microtiter plate reader (Tecan M200) for 20 minutes at 37° C. The percentage of inhibition of enzymatic activity (expressed as maximum rate of cleavage of the substrate) is calculated with respect to the enzymatic activity in the absence of inhibitor. The curve of inhibition as a function of the concentrations makes it possible to determine the IC$_{50}$ of each compound (that is to say, the concentration necessary in order to obtain 50% inhibition of the enzymatic activity) or the percentage inhibition at the maximum concentration tested (10 μM).

The compounds of formula (I) according to the present invention inhibit factor IXa and/or factor Xa, with $IC_{50}$ values of between 1 nM and 10 µM, preferably of less than 1 µM. Examples of $IC_{50}$ are given in the table I.

Determination of the Inhibition of the Kinetics of Thrombin Generation

A platelet-poor plasma (PPP) and platelet-rich plasma (PRP) thrombin generation test (TGT) is carried out, the said plasmas comprising all the factors of the coagulation cascade. The blood is withdrawn from the rat abdominal aorta over sodium citrate (3.8%, pH 7.4). PRP is obtained after centrifuging the blood (150×g, 10 min) and PPP by additional centrifuging of the pellet (1100×g, 15 min). PRP is diluted with PPP in order to adjust the number of platelets (300,000 platelets/mm³). The PPP and PRP thrombin generation test is carried out according to the method described as "Calibrated Automated Measurement of Thrombin Generation (CAT)" by H. C. Hemker et al. (*Pathophysiol Haemost Thromb* 33 (2003), pp. 4-15). According to this method, Thrombin generation was measured in a Fluoroscan Ascent® fluorometer (Thermolab systems OY, Helsinki, Finland) equipped with a dispenser. Fluorescence intensity was detected at wavelengths of 390 nm (excitation filter) and 460 nm (emission filter). Briefly, 80 µL of PPP was dispensed into the wells of round-bottom 96 well-microtitre plates. 20 µL of a mixture containing tissue factor and phospholipids was added to the plasma sample. The starting reagent contains fluorogenic substrate and CaCl2 and automatically dispensed (20 µL per well). A dedicated software program, Thrombinoscope® (Thrombinoscope by, Maastricht, The Netherlands) enables the calculation of thrombin activity against the calibrator (Biodis) and displays thrombin activity against time.

Recombinant human tissue factor (TF) Innovin® was obtained from Dade Behring (B4212-50) and used at a final dilution of 1/200 or 1/1000 respectively for TGT evaluation in rat PPP or rat PRP.

The phospholipid vesicles used (in PPP thrombin generation test) at a final concentration of 1 µM were home-made and consisted of 22 mol % phosphatidylserine (PS), and 78 mol % phosphatidylcholine (PC). Hepes-buffered saline contained 20 mM Hepes (Sigma Aldrich, Poole, UK), 150 mM NaCl and 5 mg/mL bovine serum albumin (BSA) (Sigma Aldrich, Poole, UK), pH 7.35. This buffer was stored at −20° C. until use. A fresh mixture of fluorogenic substrate and CaCl2 was prepared before starting each experiment. Fluorogenic substrate, Z-Gly-Gly-Arg-AMC, was obtained from Bachem (Bubendorf, Switzerland). The mixture of 2.5 mM fluorogenic substrate and 0.1 M CaCl2 was prepared using buffer containing 20 mM HEPES and 60 mg/mL BSA, pH 7.35. The Calibrator with the activity of 600 nM human thrombin was obtained from Biodis. Polypropylene round bottom Greiner microtitre plates available in all centres were used. Endogenous thrombin potential (ETP) results were used to calculate inhibitory effect of the compounds because of the clinical relevance of this parameter reported in the literature.

In this test, the compounds of formula (I) according to the present invention inhibit or slow down the generation of thrombin, at concentrations generally between 1 nM and 10 µM. Examples of inhibition of thrombin generation are given in the table below:

| Compound number | 10 µM | 1 µM | 0.1 µM | 10 µM | 1 µM | 0.1 µM |
|---|---|---|---|---|---|---|
| | Rat PRP (% inh) | | | Rat PPP (% inh) | | |
| 1 | 23.2 | 14.2 | 4.8 | 6.3 | 6.4 | 1.8 |
| 2 | 23.7 | 12.2 | 4.0 | 5.3 | 5.6 | 1.3 |
| 6 | 40.4 | 18.4 | 2.1 | 26.6 | 7.9 | −0.1 |
| 7 | 98.2 | 92.6 | 58.7 | 94.2 | 84.3 | 58.8 |
| 14 | 92.9 | 78.2 | 16.9 | 85.4 | 69.3 | 25.3 |
| 15 | 95.6 | 74.6 | −5.9 | 86.0 | 60.0 | 18.7 |
| 16 | 95.8 | 77.0 | 16.6 | 82.2 | 59.8 | 16.2 |
| 17 | 89.3 | 64.0 | 18.4 | 67.2 | 36.8 | 6.0 |
| 18 | 90.5 | 63.5 | 9.2 | 72.5 | 29.9 | 2.3 |
| 19 | 93.0 | 49.4 | 6.6 | 62.6 | 23.5 | 1.3 |
| 21 | 83.8 | 67.2 | 30.0 | 77.0 | 55.1 | 19.5 |
| 22 | 65.1 | 24.9 | 6.1 | 49.0 | 15.8 | 3.8 |
| 24 | 97.1 | 81.3 | 34.1 | 90.0 | 70.7 | 27.0 |
| 26 | 52.7 | 10.8 | 1.0 | 37.6 | 13.1 | 0 |
| 28 | 81.6 | 58 | 8.4 | 70.4 | 46.2 | 7.2 |
| 29 | 71.2 | 36.1 | 17.2 | 44.5 | 16.3 | 5.0 |
| 30 | 92.0 | 66.8 | 12.0 | 79.7 | 55.1 | 20.5 |
| 32 | 69.3 | 28.5 | 3.5 | 42.6 | 24 | 0 |
| 34 | 79.0 | 29.2 | 8.6 | 65.5 | 34.2 | 8.9 |
| 36 | 40.9 | 16.4 | 12.2 | 14.0 | 6.1 | 3.7 |
| 38 | 8.2 | 15.5 | 11.0 | 8.7 | 2.3 | 0.0 |
| 40 | 71.2 | 32.6 | 8.6 | 52.0 | 33.6 | 45.0 |
| 41 | 62.6 | 23.5 | 9.7 | 33.8 | 14.5 | −10.0 |
| 42 | 39.3 | 20.8 | 8.3 | 20.1 | 11.1 | 10.1 |
| 43 | 77.6 | 21.9 | 5.8 | 67.2 | 34.6 | 6.8 |
| 44 | 67.6 | 21.6 | 1.8 | 77.0 | 57.6 | 12.1 |
| 45 | 84.4 | 55.7 | 17.7 | 77.0 | 57.6 | 12.1 |
| 46 | 63.5 | 23.4 | 0.9 | 77.0 | 57.6 | 12.1 |
| 47 | 69.5 | 37.5 | 9.1 | 35.9 | 12.2 | −0.6 |
| 48 | 29.6 | 13.9 | 4.9 | 17.7 | 1.3 | 2.6 |
| 49 | 54.2 | 21.9 | 8.8 | 22.3 | 9.7 | 0 |
| 50 | 87.5 | 61.4 | 16.7 | 72.1 | 47.9 | 11.6 |
| 51 | 96 | 58 | 14 | 77 | 46 | 3.5 |
| 52 | 60.1 | 15.2 | 0 | 35.3 | 6.6 | 0 |
| 53 | 73.5 | 26.2 | 3.1 | 54.7 | 19.6 | 0.1 |
| 54 | 27.7 | 2.1 | 0.0 | 17.6 | 0.0 | 0.0 |
| 55 | 29.3 | 14.6 | 5.8 | 6.3 | 3.7 | 3.2 |
| 56 | 27.7 | 13.8 | 5.2 | 13.5 | 4.9 | 3.7 |
| 57 | 36.6 | 16.0 | 1.7 | 29.3 | 9.6 | 0.0 |
| 58 | 41.1 | 17.2 | 2.5 | 47.0 | 13.6 | 0.8 |
| 59 | 42.1 | 20.2 | 4.1 | 41.6 | 14.0 | 3.1 |
| 60 | 49.2 | 16.9 | 6.1 | 46.6 | 13.4 | 3.7 |
| 61 | 76.6 | 30.3 | 9.1 | 58.8 | 25.1 | 3.0 |
| 62 | 81.4 | 35.9 | 15.7 | 65.7 | 31.3 | 6.7 |
| 63 | 46.4 | 23.5 | 9.6 | 38.3 | 15.1 | 3.8 |
| 64 | 47.3 | 19.4 | 7.2 | 38.0 | 14.2 | 1.5 |
| 65 | 38.2 | 24.6 | 4.2 | 19.3 | 8.7 | 0.1 |
| 66 | 49.9 | 26.0 | 12.3 | 24.4 | 15.6 | 0.8 |
| 67 | 25.0 | 8.1 | 1.1 | 10.8 | 6.6 | 1.9 |
| 68 | 19.3 | 11.1 | 2.7 | 7.4 | 5.5 | 1.3 |
| 69 | 18.9 | 5.6 | 0.1 | 5.2 | 3.1 | 0.0 |
| 70 | 21.5 | 9.8 | 3.1 | 6.0 | 4.1 | 0.3 |
| 71 | 29.5 | 4.7 | 4.2 | 14.5 | 4.6 | 1.2 |
| 72 | 18.5 | 5.3 | 0.0 | 7.3 | 0.8 | 0.0 |
| 73 | 15.3 | 8.6 | 1.8 | 8.5 | 12.2 | 1.8 |
| 74 | 11.5 | 3.1 | 0.7 | 3.0 | 0.3 | 0.0 |
| 75 | 23.0 | 10.2 | 1.9 | 9.3 | 3.1 | 0.2 |
| 76 | 21.9 | 7.8 | 0.9 | 6.0 | 4.2 | 0.9 |
| 77 | 69.8 | 17.0 | 3.6 | 57.9 | 21.2 | 5.0 |
| 78 | 31.7 | 11.9 | 0.0 | 21.2 | 9.2 | 0.8 |
| 79 | 47.1 | 14.0 | 4.4 | 32.4 | 13.0 | 3.0 |
| 80 | 17.2 | 4.4 | 0.9 | 2.2 | 2.7 | 0.5 |
| 81 | 28.9 | 11.9 | 1.9 | 3.8 | 3.6 | 0.8 |
| 82 | 31.4 | 15.1 | 3.5 | 7.0 | 0.2 | 0.0 |
| 83 | 33.9 | 22.1 | 7.6 | 16.3 | 4.3 | 1.1 |
| 84 | 60.3 | 20.2 | 0.3 | 29.0 | 4.3 | 0.0 |
| 85 | 64.8 | 24.7 | 5.5 | 56.2 | 17.4 | 0.0 |
| 86 | 21.1 | 6.1 | 0.0 | 9.6 | 5.1 | 3.4 |
| 87 | 16.1 | 7.6 | 5.7 | 4.4 | 2.9 | 2.9 |
| 88 | 17.8 | 8.5 | 5.2 | 4.1 | 2.9 | 1.9 |
| 89 | 22.1 | 8.1 | 4.9 | 5.5 | 1.3 | 0.7 |
| 90 | 21.3 | 10.1 | 1.9 | 1.6 | 4.2 | 1.5 |
| 91 | 25.4 | 8.0 | 3.6 | 4.0 | 5.4 | 0.0 |
| 92 | 83.8 | 37.3 | 11.1 | 75.3 | 38.8 | 6.0 |
| 93 | 75.3 | 24.3 | 3.6 | 46.6 | 12.6 | 0.0 |
| 94 | 46.0 | 17.1 | 6.5 | 25.4 | 6.9 | 1.4 |

-continued

| Compound number | 10 µM | 1 µM | 0.1 µM | 10 µM | 1 µM | 0.1 µM |
|---|---|---|---|---|---|---|
| 95 | 59.9 | 17.5 | 6.3 | 35.0 | 7.7 | 0.0 |
| 96 | 35.9 | 4.8 | 0.0 | 44.8 | 6.1 | 0.0 |
| 103 | 89.4 | 57.6 | 7.5 | 86.3 | 65.6 | 22.8 |
| | Human PRP (% inh) | | | Human PPP (% inh) | | |
| 1 | 2.4 | 0.0 | 0.0 | 8.2 | 7.7 | 3.0 |
| 17 | 81.9 | 38.6 | 4.4 | 80.5 | 55.1 | 15.4 |
| 18 | 49.1 | 2.9 | 0.0 | 69.4 | 31.0 | 4.7 |
| 19 | 29.3 | 0.0 | 0.0 | 47.2 | 5.5 | 0.8 |
| 47 | 69.6 | 22.2 | 15.8 | 58.1 | 25.4 | 8.1 |
| 51 | 35.0 | 3.0 | 0.0 | 51.0 | 18.0 | 7.0 |
| 52 | 3.5 | 0.0 | 0.0 | 25.2 | 8.8 | 4.5 |
| 53 | 35.6 | 7.5 | 0.0 | 54.9 | 25.9 | 7.5 |
| 54 | 0.0 | 0.0 | 0.0 | 33.5 | 11.3 | 4.0 |
| 63 | 41.7 | 16.3 | 3.1 | 48.2 | 20.4 | 2.7 |
| 65 | 0.0 | 5.7 | 0.0 | 16.2 | 7.0 | 4.2 |
| 66 | 25.9 | 11.8 | 15.9 | 29.7 | 14.3 | 8.6 |
| 78 | 1.1 | 7.4 | 9.2 | 10.0 | 0.1 | 0.1 |
| 79 | 49.9 | 9.1 | 3.3 | 54.5 | 24.5 | 3.8 |
| 82 | 14.6 | 0.0 | 10.6 | 1.1 | 2.3 | 0.0 |
| 83 | 16.9 | 6.3 | 0.0 | 26.4 | 6.1 | 0.0 |
| 84 | 8.7 | 0.0 | 0.0 | 0.4 | 3.3 | 0.7 |
| 85 | 1.0 | 0.0 | 0.0 | 19.8 | 15.7 | 13.7 |
| 88 | 0.0 | 5.4 | 0.0 | 0.0 | 0.0 | 0.0 |
| 92 | 39.3 | 13.6 | 2.4 | 54.6 | 23.5 | 4.6 |
| 93 | 40.7 | 0.0 | 2.8 | 46.0 | 13.4 | 0.8 |
| 94 | 4.3 | 2.2 | 0.0 | 9.4 | 0.0 | 0.0 |
| 95 | 41.2 | 9.0 | 0.0 | 59.7 | 29.2 | 9.0 |
| 96 | 53.7 | 20.1 | 0.0 | 39.9 | 15.7 | 1.7 |

Some discrepancies can be observed between in vitro activity on isolated enzymes and activity in both rat and human plasma. For example, the compounds 51, 52, 54, 61, 65, 78, 85, 88 according to the invention present a weak activity on both isolated enzymes and TGT in human PRP but with a strong activity in rat PRP. These results are linked to the fact that compounds 51, 52, 54, 61, 65, 78, 85, 88 according to the invention are prodrugs, i.e. inactive by themselves on isolated enzymes or plasma when they are not converted to active drug. In human plasma, all these prodrugs present a high plasmatic stability, while in rat plasma they are rapidly converted to the corresponding active drugs, this is the reason for which they are active in rat plasma TGT model.

The compounds according to the invention are thus inhibitors of factor IXa. Consequently, they can be used in the preparation of medicaments; in particular of medicaments which are inhibitors of coagulation factor IXa and factor Xa. With a high inhibitory effect on factor IXa and a weak inhibition of factor Xa, the compounds described in this patent are expected to present high anti-thrombotic properties with a moderate bleeding side effect. For some of those compounds, in vivo evaluation of their ability to inhibit thrombus generation was performed in a model of rat venous thrombosis (wessler model adapted to rats).

Wessler Model of Thrombosis Adapted to Rats

The Wessler-like model (i.e. venous thrombosis model) was performed in anesthetized rats. The abdominal vena cava was exposed and two loosed silk ligatures separated from ~0.7 cm were placed around the vessel. Thrombus formation was induced by a 1 ng/kg dose of recombinant human thromboplastin into the penile vein and 10 sec after the freed segment of vessel was promptly occluded by tightening both ligatures during 20 min. The segment was then harvested, the vein was longitudinally dissected out and the thrombus blotted and weighted. The compounds and corresponding vehicles were administered by oral or intravenous routes 5, 60 or 120 minutes prior injection of thromboplastin. The thrombus weight was measured 20 min after the thromboplastin injection.

In this test, the compounds of formula (I) according to the present invention inhibit or slow down the thrombus generation (thrombus weight), at 3 mg/kg after iv injection or 30 mg/kg after oral administration. Examples of inhibition of thrombus generation are given in the table below:

| | Rat Wessler iv @3 mg/kg (% inh of thrombus weigth) | | | Rat Wessler po @30 mg/kg (% inh of thrombus weigth) |
|---|---|---|---|---|
| Compound number | 5 min | 2 h | Compound number | 1 h |
| 53 | 43% | 13% | 65 | 7% |
| 66 | 41% | 51% | 97 | 37% |
| 79 | 61% | 30% | 98 | 58% |
| 81 | 20% | ND | 99 | 51% |
| 83 | 57% | 20% | 100 | 36% |
| 95 | 43% | 0% | 24 | 43% |
| 47 | 41% | 5% | 23 | 45% |
| 22 | 0% | ND | 25 | 43% |
| 96 | 62% | 49% | 31 | 57% |

Thus, according to another of its aspects, a subject-matter of the invention is medicaments which comprise a compound of formula (I) or an addition salt of the latter with a pharmaceutically acceptable acid or base or also a hydrate or a solvate of the compound of formula (I).

The compounds of the invention are particularly advantageous in the manufacture of medicaments intended for the treatment and prevention of thrombosis of arterial and/or venous origin.

They can be used for the treatment and prevention of various pathologies resulting from a modification of the homeostasis of the coagulation system appearing in particular during disorders of the cardiovascular and cerebrovascular system, such as thromboembolic disorders associated with artherosclerosis and diabetes, for example unstable angina, apoplexy, post-angioplasty restenosis, endarterectomy or the insertion of endovascular prostheses; or thromboembolic disorders associated with rethrombosis after thrombolysis, with infarction, with dementia of ischaemic origin, with peripheral arterial diseases, with haemodialysis or with auricular fibrillations, or also during the use of vascular prostheses for aortocoronary bypasses. These compounds can furthermore be used for the treatment or prevention of thromboembolic pathologies of venous origin, such as pulmonary embolisms. They can also be used either to prevent or to treat thrombotic complications which appear during surgical operations or together with other pathologies, such as cancer and bacterial or viral infections. In the case of the insertion of prostheses, the compounds of the present invention can be used to cover these prostheses and to thus render them haemocompatible. In particular, they can be attached to intravascular prostheses (stents).

According to another of its aspects, the present invention relates to pharmaceutical compositions comprising, as active principle, a compound according to the invention. These pharmaceutical compositions comprise an effective dose of at least one compound according to the invention or a pharmaceutically acceptable salt, a hydrate or a solvate of the said compound and at least one pharmaceutically acceptable excipient.

The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its possible salt, solvate or hydrate can be administered in unit administration form, as a mixture with conventional pharmaceutical excipients, to animals and to human beings for the prophylaxis or treatment of the above disorders or diseases.

The appropriate unit administration forms comprise oral forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For the topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The present invention, according to another of its aspects, also relates to a method for the treatment of the pathologies indicated above which comprises the administration, to a patient, of an effective dose of a compound according to the invention or one of its pharmaceutically acceptable salts or its hydrates or its solvates.

What is claimed:

1. A compound of formula (I)

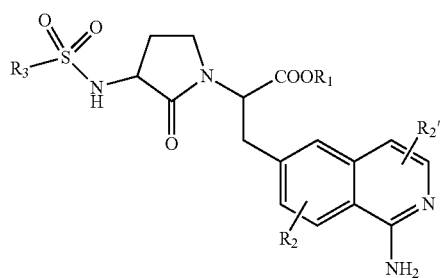

wherein $R_1$ is
hydrogen,
$(C_1-C_6)$alkyl,
$(C_3-C_7)$cycloalkyl,
$(C_3-C_7)$cycloalkyl-$(C_1-C_6)$alkyl-,
Rb—O—Ra— where Rb is $(C_1-C_6)$alkyl or $(C_3-C_7)$cycloalkyl and Ra is $(C_1-C_6)$alkyl,
Rd-O—C(O)—O-Rc- where Rd is $(C_1-C_6)$alkyl or $(C_3-C_7)$cycloalkyl, and Rc is $(C_1-C_6)$alkyl, or
Rf—C(O)—O—Re— where Re is $(C_1-C_6)$alkyl and Rf is $(C_1-C_6)$alkyl;

$R_2$ is
halogen,
—OH,
—CN,
$(C_1-C_6)$alkyl or —O—$(C_1-C_6)$alkyl in which each $(C_1-C_6)$alkyl is non-substituted or substituted by one or more halogen identical to or different from one another, or
Rg-O—Rh—O—, in which Rg is $(C_1-C_6)$alkyl and Rh is $(C_1-C_6)$alkyl;

$R_2'$ is hydrogen or $(C_1-C_6)$alkyl;

$R_3$ is

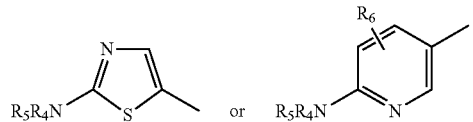

wherein $R_4$ and $R_5$ are, independently of one another, $(C_1-C_6)$ alkyl or $(C_3-C_7)$cycloalkyl, or $R_4$ and $R_5$, when taken together with the nitrogen atom to which they are attached, form a 3 to 7 membered heterocycloalkyl comprising from 1 to 2 heteroatoms chosen from nitrogen, oxygen and sulphur, said heterocycloalkyl being non-substituted or substituted by one or more groups independently selected from halogen, $(C_1-C_6)$alkyl, $(C_1-C_6)$alkoxy, —$CF_3$ and —$OCF_3$; and $R_6$ is halogen, hydrogen, $(C_1-C_6)$alkyl, $(C_1-C_6)$alkoxy or —CN;

or an enantiomer, diastereoisomer or mixture thereof, or pharmaceutically acceptable salt thereof.

2. The compound of formula (I) according to claim 1, wherein $R_3$ is

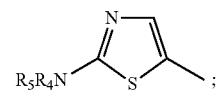

or an enantiomer, diastereoisomer or mixture thereof, or a pharmaceutically acceptable salt thereof.

3. The compound of formula (I) according to claim 1, wherein $R_3$ is

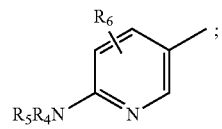

or an enantiomer, diastereoisomer or mixture thereof, or a pharmaceutically acceptable salt thereof.

4. The compound of formula (I) according to claim 1, wherein $R_2$ is —$OCF_3$, or an enantiomer, diastereoisomer or mixture thereof, or a pharmaceutically acceptable salt thereof.

5. The compound of formula (I) according to claim 1, wherein

R$_1$ is hydrogen, (C$_1$-C$_6$)alkyl, (C$_3$-C$_7$)cycloalkyl, (C$_3$-C$_7$)cycloalkyl-(C$_1$-C$_6$)alkyl, Rb—O—Ra— where Rb is (C$_1$-C$_6$)alkyl and Ra is (C$_1$-C$_6$)alkyl, Rd-O—C(O)—O-Rc- where Rd is (C$_1$-C$_6$)alkyl or (C$_3$-C$_7$)cycloalkyl, and Rc is (C$_1$-C$_6$)alkyl, or Rf—C(O)—O—Re— where Re is (C$_1$-C$_6$)alkyl and Rf is (C$_1$-C$_6$)alkyl;

or an enantiomer, diastereoisomer or mixture thereof, or a pharmaceutically acceptable salt thereof.

6. The compound of formula (I) according to claim 1, wherein

R$_2$ is halogen,

—OH,

—CN, (C$_1$-C$_6$)alkyl

—O—(C$_1$-C$_6$)alkyl in which each (C$_1$-C$_6$)alkyl is non-substituted or substituted by one or more halogen, identical to or different from one another, or Rg-O—Rh—O—, wherein Rg is (C$_1$-C$_6$)alkyl and Rh is (C$_1$-C$_6$)alkyl, or an enantiomer, diastereoisomer or mixture thereof, or a pharmaceutically acceptable salt thereof.

7. The compound of formula (I) according to claim 1, wherein R$_2$' is hydrogen or (C$_1$-C$_6$)alkyl, or an enantiomer, diastereoisomer or mixture thereof, or pharmaceutically acceptable salt thereof.

8. The compound of formula (I) according to claim 1, wherein

R$_4$ and R$_5$ are, independently of one another, (C$_1$-C$_6$)alkyl or (C$_3$-C$_7$)cycloalkyl, or R$_4$ and R$_5$, when taken together with the nitrogen atom to which they are attached, form a 3 to 7 membered N-heterocycloalkyl comprising from 1 to 2 heteroatoms chosen from nitrogen, oxygen and sulphur, said-heterocycloalkyl being non-substituted or substituted by one or more halogens, or an enantiomer, diastereoisomer or mixture thereof, or pharmaceutically acceptable salt thereof.

9. The compound of formula (I) according to claim 1, wherein R$_6$ is halogen, hydrogen or (C$_1$-C$_6$)alkyl, or an enantiomer, diastereoisomer or mixture thereof, or pharmaceutically acceptable salt thereof.

10. The compound of formula (I) according to claim 1, wherein

R$_1$ is hydrogen, methyl, ethyl, propyl, isopropyl, butyl, isobutyl, cyclopentyl, cyclopropylmethyl, cyclobutylmethyl, 2-methoxyethyl, cyclohexyloxycarbonyloxymethyl, 1-cyclohexyloxycarbonyl oxymethyl or 2,2-dimethylpropionyloxymethyl;

R$_2$ is chlorine, fluorine, —OH, —CN, methyl, ethyl, methoxy, ethoxy, —CF$_3$, —OCF$_3$ or 2-methoxyethoxy;

R$_2$' is hydrogen or methyl;

R$_3$ is

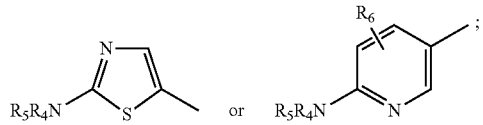

R$_4$ and R$_5$ are, independently of one another, methyl or cyclobutyl, or R$_4$ and R$_5$, when taken together with the nitrogen atom to which they are attached, form a heterocycloalkyl chosen from azetidin-1-yl or pyrrolidin-1-yl, wherein the heterocycloalkyl is non-substituted or substituted by one or two fluorine; and R$_6$ is hydrogen, chlorine or methyl;

or an enantiomer, diastereoisomer or mixture thereof, or pharmaceutically acceptable salt thereof.

11. The compound of formula (I) according to claim 1, wherein

R$_1$ is hydrogen or methyl;

R$_2$ is chlorine, —CF$_3$ or —OCF$_3$;

R$_2$' is hydrogen;

R$_3$ is

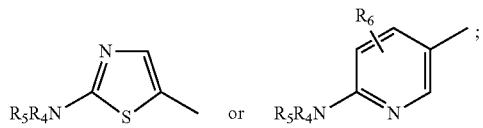

in which R$_4$ and R$_5$ are methyl, or R$_4$ and R$_5$, when taken together with the nitrogen atom to which they are attached, form a heterocycloalkyl chosen from azetidin-1-yl and pyrrolidin-1-yl, wherein the heterocycloalkyl is non-substituted or substituted by one or two fluorines; and R$_6$ is hydrogen;

or an enantiomer, diastereoisomer or mixture thereof, or a pharmaceutically acceptable salt thereof.

12. The compound of formula (I) according to claim 1, selected from:

(R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid methyl ester, (R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid, (R)-3-(1-Amino-5-fluoro-isoquinolin-6-yl)-2-[(S)-2-oxo-3-(6-pyrrolidin-1-yl-pyridine-3-sulfonylamino)-pyrrolidin-1-yl]-propionic acid ethyl ester, (R)-3-(1-Amino-5-fluoro-isoquinolin-6-yl)-2-[(S)-3-(6-dimethylamino-pyridine-3-sulfonylamino)-2-oxo-pyrrolidin-1-yl]-propionic acid, (R)-3-(1-Amino-5-fluoro-isoquinolin-6-yl)-2-[(S)-3-(6-dimethylamino-pyridine-3-sulfonylamino)-2-oxo-pyrrolidin-1-yl]-propionic acid methyl ester, (R)-3-(1-Amino-5-fluoro-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid isobutyl ester, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid cyclopropylmethyl ester, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid cyclobutylmethyl ester, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid isopropyl ester, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid cyclopentyl ester, (R)-3-(1-Amino-7-methoxy-isoquinolin-6-yl)-2-[(S)-3-(2-dimethylamino-thiazole-5-sulfonylamino)-2-oxo-pyrrolidin-1-yl]-propionic acid ethyl ester, (R)-3-(1-Amino-7-methoxy-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-methoxy-isoquinolin-6-yl)-2-[(S)-2-oxo-3-(2-pyrrolidin-1-yl-thiazole-5-sulfonylamino)-pyrrolidin-1-yl]-propionic acid cyclopropylmethyl ester, (R)-3-(1-Amino-7-methoxy-isoquinolin-6-yl)-2-[(S)-2-oxo-3-(2-pyrrolidin-1-yl-thiazole-5-sulfonylamino)-pyrrolidin-1-yl]-propionic acid ethyl ester, (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid, (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid ethyl ester, (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid cyclopropylmethyl ester, (R)-3-(1-Amino-7-methoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid isopropyl ester, (R)-3-(1-Amino-7-methoxy-isoquinolin-6-yl)-2-{(S)-3-[2-((R)-3-fluoro-pyrrolidin-1-yl)-thiazole-5-sulfonylamino]-2-oxo-pyrrolidin-1-yl}-propionic acid, (R)-3-(1-Amino-7-methoxy-isoquinolin-6-yl)-2-[(S)-3-(6-dimethylamino-5-methyl-pyridine-3-sulfonylamino)-2-oxo-pyrrolidin-1-yl]-propionic acid, (R)-3-(1-Amino-7-methoxy-isoquinolin-6-yl)-2-[(S)-3-(6-dimethylamino-5-methyl-pyridine-3-sulfonylamino)-2-oxo-pyrrolidin-1-yl]-propionic acid ethyl ester, (R)-3-(1-Amino-7-methoxy-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-methoxy-isoquinolin-6-yl)-2-[(S)-3-(6-dimethylamino-pyridine-3-sulfonylamino)-2-oxo-pyrrolidin-1-yl]-propionic acid ethyl ester, (R)-3-(1-Amino-7-methoxy-isoquinolin-6-yl)-2-[(S)-3-(5-chloro-6-dimethylamino-pyridine-3-sulfonylamino)-2-oxo-pyrrolidin-1-yl]-propionic acid, (R)-3-(1-Amino-7-methoxy-isoquinolin-6-yl)-2-[(S)-3-(5-chloro-6-dimethylamino-pyridine-3-sulfonylamino)-2-oxo-pyrrolidin-1-yl]-propionic acid ethyl ester, (R)-3-(1-Amino-7-ethyl-isoquinolin-6-yl)-2-[(S)-3-(5-chloro-6-dimethylamino-pyridine-3-sulfonylamino)-2-oxo-pyrrolidin-1-yl]-propionic acid ethyl ester, (R)-3-(1-Amino-7-methyl-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-methyl-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-ethyl-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-ethyl-isoquinolin-6-yl)-2-[(S)-3-(2-dimethylamino-thiazole-5-sulfonylamino)-2-oxo-pyrrolidin-1-yl]-propionic acid ethyl ester, (R)-3-(1-Amino-7-ethyl-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-ethyl-isoquinolin-6-yl)-2-[(S)-2-oxo-3-(2-pyrrolidin-1-yl-thiazole-5-sulfonylamino)-pyrrolidin-1-yl]-propionic acid ethyl ester, (R)-3-(1-Amino-7-ethyl-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-ethyl-isoquinolin-6-yl)-2-[(S)-3-(6-dimethylamino-pyridine-3-sulfonylamino)-2-oxo-pyrrolidin-1-yl]-propionic acid ethyl ester, (R)-3-(1-Amino-7-ethyl-isoquinolin-6-yl)-2-[(S)-2-oxo-3-(6-pyrrolidin-1-yl-pyridine-3-sulfonylamino)-pyrrolidin-1-yl]-propionic acid, (R)-3-(1-Amino-7-ethyl-isoquinolin-6-yl)-2-[(S)-2-oxo-3-(6-pyrrolidin-1-yl-pyridine-3-sulfonylamino)-pyrrolidin-1-yl]-propionic acid ethyl ester, (R)-3-(1-Amino-7-ethyl-isoquinolin-6-yl)-2-[(S)-3-(5-chloro-6-dimethylamino-pyridine-3-sulfonylamino)-2-oxo-pyrrolidin-1-yl]-propionic acid, (R)-3-(1-Amino-7-methoxy-isoquinolin-6-yl)-2-[(S)-3-(5-chloro-6-dimethylamino-pyridine-3-sulfonylamino)-2-oxo-pyrrolidin-1-yl]-propionic acid ethyl ester, (R)-3-(1-Amino-7-fluoro-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-fluoro-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-fluoro-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid, (R)-3-(1-Amino-7-trifluoromethoxy-isoquinolin-6-yl)-2-[(S)-3-(2-dimethylamino-thiazole-5-sulfonylamino)-2-oxo-pyrrolidin-1-yl]-propionic acid methyl ester, (R)-3-(1-Amino-7-trifluoromethoxy-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-ethoxy-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-ethoxy-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-ethoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid, (R)-3-(1-Amino-7-hydroxy-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-chloro-isoquinolin-6-yl)-2-{(S)-3-[2-(cyclobutyl-methyl-amino)-thiazole-5-sulfonylamino]-2-oxo-pyrrolidin-1-yl}-propionic acid, (R)-3-(1-Amino-7-chloro-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-chloro-isoquinolin-6-yl)-2-[(S)-3-(2-dimethylamino-thiazole-5-sulfonylamino)-2-oxo-pyrrolidin-1-yl]-propionic acid methyl ester, (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid methyl ester, (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid methyl ester, (R)-3-(1-Amino-7-trifluoromethoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid methyl ester, (R)-3-(1-Amino-7-trifluoromethoxy-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid, (R)-3-(1-Amino-7-trifluoromethoxy-isoquinolin-6-yl)-2-[(S)-3-(2-azetidin-1-yl-thiazole-5-sulfonylamino)-2-oxo-pyrrolidin-1-yl]-propionic acid methyl ester, (R)-3-(1-Amino-7-trifluoromethoxy-isoquinolin-6-yl)-2-[(S)-3-(2-azetidin-1-yl-thiazole-5-sulfonylamino)-2-oxo-pyrrolidin-1-yl]-propionic acid, (R)-3-(1-Amino-7-trifluoromethoxy-isoquinolin-6-yl)-2-[(S)-3-(6-dimethylamino-pyridine-3-sulfonylamino)-2-oxo-pyrrolidin-1-yl]-propionic acid methyl ester, (R)-3-(1-Amino-7-trifluoromethoxy-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-chloro-isoquinolin-6-yl)-2-[(S)-3-(6-dimethylamino-pyridine-3-sulfonylamino)-2-oxo-pyrrolidin-1-yl]-propionic acid methyl ester, (R)-3-(1-Amino-7-chloro-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-fluoro-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-fluoro-isoquinolin-6-yl)-2-[(S)-3-(6-dimethylamino-pyridine-3-sulfonylamino)-2-oxo-pyrrolidin-1-yl]-propionic acid methyl ester, (R)-3-(1-Amino-7-chloro-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid methyl ester, (R)-3-(1-Amino-7-chloro-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid, (R)-3-(1-Amino-7-fluoro-isoquinolin-6-yl)-2-[(S)-3-(5-chloro-6-dimethylamino-pyridine-3-sulfonylamino)-2-oxo-pyrrolidin-1-yl]-propionic acid methyl ester, (R)-3-(1-Amino-7-fluoro-isoquinolin-6-yl)-2-[(S)-3-(5-chloro-6-dimethylamino-pyridine-3-sulfonylamino)-2-oxo-pyrrolidin-1-yl]-propionic acid, (R)-3-(1-Amino-7-chloro-isoquinolin-6-yl)-2-[(S)-3-(5-chloro-6-dimethylamino-pyridine-3-sulfonylamino)-2-oxo-pyrrolidin-1-yl]-propionic acid methyl ester, (R)-3-(1-Amino-7-chloro-isoquinolin-6-yl)-2-[(S)-3-(5-chloro-6-dimethylamino-pyridine-3-sulfonylamino)-2-oxo-pyrrolidin-1-yl]-propionic acid, (R)-3-(1-Amino-7-fluoro-isoquinolin-6-yl)-2-[(S)-3-(6-dimethylamino-5-methyl-pyridine-3-sulfonylamino)-2-oxo-pyrrolidin-1-yl]-propionic acid methyl ester, (R)-3-(1-Amino-7-trifluoromethoxy-isoquinolin-6-yl)-2-[(S)-3-(6-dimethylamino-5-methyl-pyridine-3-sulfonylamino)-2-oxo-pyrrolidin-1-yl]-propionic acid methyl ester, (R)-3-(1-Amino-7-fluoro-isoquinolin-6-yl)-2-[(S)-3-(6-dimethylamino-5-methyl-pyridine-3-sulfonylamino)-2-oxo-pyrrolidin-1-yl]-propionic acid, (R)-3-(1-Amino-7-trifluoromethoxy-isoquinolin-6-yl)-2-[(S)-3-(6-dimethylamino-5-methyl-pyridine-3-sulfonylamino)-2-oxo-pyrrolidin-1-yl]-propionic acid, (R)-3-(1-Amino-7-chloro-isoquinolin-6-yl)-2-[(S)-3-(6-dimethylamino-5-methyl-pyridine-3-sulfonylamino)-2-oxo-pyrrolidin-1-yl]-propionic acid methyl ester, (R)-3-(1-Amino-7-chloro-isoquinolin-6-yl)-2-[(S)-3-(6-dimethylamino-5-methyl-pyridine-3-sulfonylamino)-2-oxo-pyrrolidin-1-yl]-propionic acid, (R)-3-(1-Amino-7-trifluoromethoxy-isoquinolin-6-yl)-2-[(S)-3-(2-dimethylamino-thiazole-5-sulfonylamino)-2-oxo-pyrrolidin-1-yl]-propionic acid methyl ester, (R)-3-(1-Amino-7-trifluoromethyl-isoquinolin-6-yl)-2-[(S)-3-(2-dimethylamino-thiazole-5-sulfonylamino)-2-oxo-pyrrolidin-1-yl]-propionic acid methyl ester, (R)-3-(1-Amino-7-trifluoromethyl-isoquinolin-6-yl)-2-[(S)-3-(2-dimethylamino-thiazole-5-sulfonylamino)-2-oxo-pyrrolidin-1-yl]-propionic acid, (R)-3-(1-Amino-7-trifluoromethyl-isoquinolin-6-yl)-2-[(S)-2-oxo-3-(2-pyrrolidin-1-yl-thiazole-5-sulfonylamino)-pyrrolidin-1-yl]-propionic acid methyl ester, (R)-3-(1-Amino-7-trifluoromethyl-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-trifluoromethyl-isoquinolin-6-yl)-2-[(S)-3-(6-dimethylamino-pyridine-3-sulfonylamino)-2-oxo-pyrrolidin-1-yl]-propionic acid methyl ester, (R)-3-(1-Amino-7-trifluoromethyl-isoquinolin-6-yl)-2-[(S)-3-(6-dimethylamino-pyridine-3-sulfonylamino)-2-oxo-pyrrolidin-1-yl]-propionic acid, (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid ethyl ester, (R)-3-(1-Amino-7-chloro-isoquinolin-6-yl)-2-[(S)-3-(2-azetidin-1-yl-thiazole-5-sulfonylamino)-2-oxo-pyrrolidin-1-yl]-propionic acid methyl ester, (R)-3-(1-Amino-7-trifluoromethoxy-isoquinolin-6-yl)-2-[(S)-3-(5-chloro-6-dimethylamino-pyridine-3-sulfonylamino)-2-oxo-pyrrolidin-1-yl]-propionic acid methyl ester, (R)-3-(1-Amino-7-trifluoromethoxy-isoquinolin-6-yl)-2-[(S)-3-(5-chloro-6-dimethylamino-pyridine-3-sulfonylamino)-2-oxo-pyrrolidin-1-yl]-propionic acid, (R)-3-(1-Amino-7-trifluoromethyl-isoquinolin-6-yl)-2-[(S)-3-(2-azetidin-1-yl-thiazole-5-sulfonylamino)-2-oxo-pyrrolidin-1-yl]-propionic acid methyl ester, (R)-3-(1-Amino-7-trifluoromethyl-isoquinolin-6-yl)-2-[(S)-3-(2-azetidin-1-yl-thiazole-5-sulfonylamino)-2-oxo-pyrrolidin-1-yl]-propionic acid, (R)-3-(1-Amino-7-trifluoromethyl-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid methyl ester, (R)-3-(1-Amino-7-trifluoromethyl-isoquinolin-6-yl)-2-{(S)-3-[2-(3,3-difluoro-pyrrolidin-1-yl)-thiazole-5-sulfonylamino]-2-oxo-pyrrolidin-1-yl}-propionic acid, (R)-3-(1-Amino-7-chloro-isoquinolin-6-yl)-2-[(S)-3-(2-azetidin-1-yl-thiazole-5-sulfonylamino)-2-oxo-pyrrolidin-1-yl]-propionic acid, (R)-3-(1-Amino-7-chloro-isoquinolin-6-yl)-2-[(S)-2-oxo-3-(2-pyrrolidin-1-yl-thiazole-5-sulfonylamino)-pyrrolidin-1-yl]-propionic acid butyl ester, (R)-3-(1-Amino-7-cyano-isoquinolin-6-yl)-2-[(S)-2-oxo-3-(2-pyrrolidin-1-yl-thiazole-5-sulfonylamino)-pyrrolidin-1-yl]-propionic acid methyl ester, (R)-3-(1-Amino-7-cyano-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-isoquinolin-6-yl)-2-[(S)-2-oxo-3-(6-pyrrolidin-1-yl-pyridine-3-sulfonylamino)-pyrrolidin-1-yl]-propionic acid, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid ethyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid cyclopropylmethyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid butyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid isopropyl ester, (R)-3-[1-Amino-7-(2-methoxy-ethoxy)-isoquinolin-6-yl]-2-[(S)-3-(2-dimethylamino-thiazole-5-sulfonylamino)-2-oxo-pyrrolidin-1-yl]-propionic acid ethyl ester, (R)-3-[1-Amino-7-(2-methoxy-ethoxy)-isoquinolin-6-yl]-2-[(S)-3-(2-dimethylamino-thiazole-5-sulfonylamino)-2-oxo-pyrrolidin-1-yl]-propionic acid, (R)-3-(1-Amino-5-fluoro-3-methyl-isoquinolin-6-yl)-2-[(S)-2-oxo-3-(6-pyrrolidin-1-yl-pyridine-3-sulfonylamino)-pyrrolidin-1-yl]-propionic acid, (R)-3-(1-Amino-5-fluoro-3-methyl-isoquinolin-6-yl)-2-[(S)-2-oxo-3-(6-pyrrolidin-1-yl-pyridine-3-sulfonylamino)-pyrrolidin-1-yl]-propionic acid methyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 2-methoxyethyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 2,2-dimethylpropionyloxymethyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid 1-cyclohexyloxycarbonyloxy-ethyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid cyclohexyloxycarbonyloxymethyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid propyl ester, (R)-3-(1-Amino-7-trifluoromethoxy-isoquinolin-6-yl)-2-[(S)-2-oxo-3-(2-pyrrolidin-1-yl-thiazole-5-sulfonylamino)-pyrrolidin-1-yl]-propionic acid, or an enantiomer, diastereoisomer or mixture thereof, or a pharmaceutically acceptable salt thereof.

13. A compound of formula (A), (B), (C), (D) or (E):

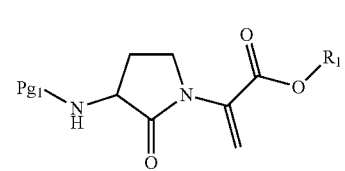

A

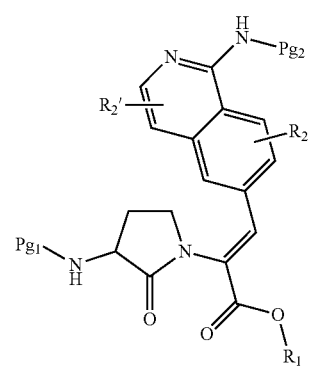

B

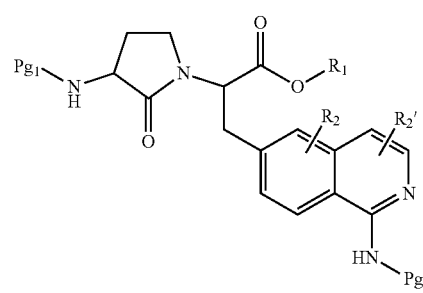

C

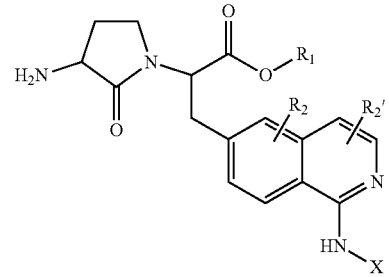

D

-continued

E

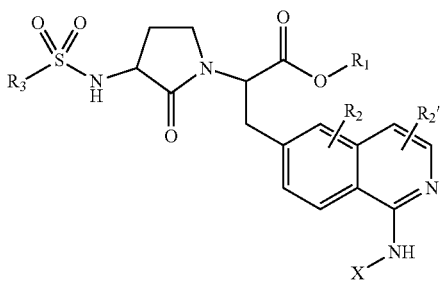

wherein
$R_1$ is H, alkyl, cycloalkyl or cycloalkylalkyl-;
$R_2$ is halogen, —OH, —CN, $(C_1\text{-}C_6)$alkyl or —O—$(C_1\text{-}C_6)$alkyl in which each $(C_1\text{-}C_6)$alkyl is non-substituted or substituted by one or more halogen, or Rg-O—Rh—O—, wherein Rg is $(C_1\text{-}C_6)$alkyl and Rh is $(C_1\text{-}C_6)$alkyl;
$R_2'$ is hydrogen or $(C_1\text{-}C_6)$alkyl;
$R_3$ is

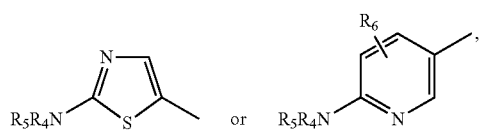

wherein $R_4$ and $R_5$ are, independently of one another, $(C_1\text{-}C_6)$alkyl or $(C_3\text{-}C_7)$cycloalkyl,
or $R_4$ and $R_5$, when taken together with the nitrogen atom to which they are attached, form a 3 to 7 membered heterocycloalkyl comprising from 1 to 2 heteroatoms chosen from nitrogen, oxygen and sulphur, the heterocycloalkyl being non-substituted or substituted by one or more groups independently selected from halogen, $(C_1\text{-}C_6)$alkyl, $(C_1\text{-}C_6)$alkoxy, —$CF_3$ and —$OCF_3$;
$Pg_1$ is an amino protective group; and
X is H or $Pg_2$, wherein $Pg_2$ is an amino protective group; or an enantiomer, diastereoisomer or mixture thereof, or pharmaceutically acceptable salt thereof.

14. A medicament comprising a compound of formula (I) according to claim 1 or an addition salt thereof, with a pharmaceutically acceptable acid or base or also a hydrate or a solvate of said compound of formula (I).

15. A pharmaceutical composition comprising as active principle, a compound of formula (I) according to claim 1, or a pharmaceutically acceptable salt thereof, a hydrate or a solvate of the said compound, and at least one pharmaceutically acceptable excipient.

16. A method for the treatment and/or prevention of thrombosis of arterial and/or venous origin comprising administering a compound of formula (I) according to claim 1, or an enantiomer, diastereoisomer or mixture thereof, or pharmaceutically acceptable salt thereof.

17. A method for the treatment and/or prevention of pathologies resulting from a modification of the homeostasis of the coagulation system, the method comprising administering to a patient in need thereof, a compound of formula (I) according to claim 1.

18. The method according to claim 17, wherein the homeostasis of the coagulation system appears during disorders of the cardiovascular and cerebrovascular systems.

19. The method according to claim 17, wherein the homeostasis of the coagulation system appears during thromboembolic disorders associated with atherosclerosis and diabetes, unstable angina, apoplexy, post-angioplasty restenosis, endarterectomy or during the insertion of endovascular prostheses.

20. The method according to claim 17, wherein the homeostasis of the coagulation system appears during thromboembolic disorders associated with rethrombosis after thrombolysis, with infarction, dementia of ischaemic origin, peripheral arterial diseases, haemodialysis or with auricular fibrillations.

21. The method according to claim 17, wherein the homeostasis of the coagulation system appears during the use of vascular prostheses for aortocoronary bypasses, thromboembolic pathologies of venous origin, pulmonary embolisms, thrombotic complications which appear during surgical operations or together with other pathologies, cancer and bacterial or viral infections.

22. A process for the preparation of the compound of formula (I) according to claim 1, the process comprising reacting a compound of formula (D):

(D)

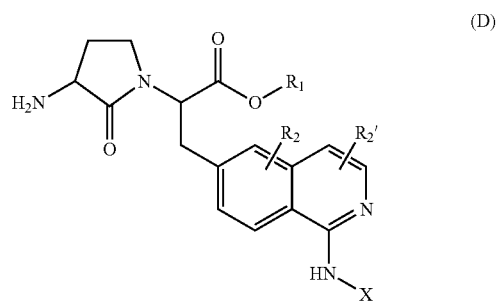

where
$R_1$ is H, alkyl, cycloalkyl or cycloalkylalkyl-,
$R_2$ is halogen, —OH, —CN, $(C_1\text{-}C_6)$alkyl or —O—$(C_1\text{-}C_6)$alkyl in which each $(C_1\text{-}C_6)$alkyl is non-substituted or substituted by one or more halogen identical to or different from one another, or Rg-O—Rh—O—, in which Rg is $(C_1\text{-}C_6)$alkyl and Rh is $(C_1\text{-}C_6)$alkyl,
$R_2'$ is hydrogen or $(C_1\text{-}C_6)$alkyl and
X is H or $Pg_2$, wherein $Pg_2$ is an amino protective group
with a compound of formula $R_3$—$SO_2$-Hal, wherein
$R_3$ is

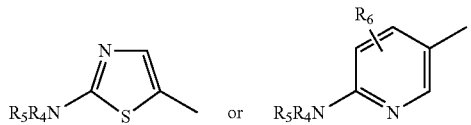

wherein $R_4$ and $R_5$ are, independently of one another, $(C_1\text{-}C_6)$alkyl or $(C_3\text{-}C_7)$cycloalkyl, or $R_4$ and $R_5$, when taken together with the nitrogen atom to which they are attached, form a 3 to 7 membered heterocycloalkyl comprising from 1 to 2 heteroatoms chosen from nitrogen, oxygen and sulphur, said heterocycloalkyl being non-substituted or substituted by one or more groups independently selected from halogen, $(C_1-C_6)$alkyl, $(C_1-C_6)$alkoxy, —$CF_3$ and —$OCF_3$, and Hal is a halogen atom;

optionally followed by deprotection of $Pg_2$, when X is $Pg_2$; and/or hydrolysis of $R_1$ to provide a compound of formula (I) in which $R_1$ is H, said hydrolysis being optionally followed by esterification of the compound of formula I in which $R_1$ is H with $R_1$-Hal, wherein Hal is halogen, to provide a compound of formula (I) wherein $R_1$ is $(C_1-C_6)$alkyl, $(C_3-C_7)$cycloalkyl, $(C_3-C_7)$cycloalkyl-$(C_1-C_6)$alkyl-, Rb—O—Ra— where Rb is $(C_1-C_6)$alkyl and Ra is $(C_1-C_6)$alkyl, Rd-O—C(O)—O—Rc- where Rd is $(C_1-C_6)$alkyl or $(C_3-C_7)$cycloalkyl and Rc is $(C_1-C_6)$alkyl, or Rf—C(O)—O—Re— where Re is $(C_1-C_6)$alkyl and Rf is $(C_1-C_6)$alkyl; or transesterification of $R_1$ with the corresponding $R_1$—OH, in the presence of an alkoxide, to provide a compound of formula (I) wherein $R_1$ is $(C_1-C_6)$alkyl, $(C_3-C_7)$cycloalkyl, $(C_3-C_7)$cycloalkyl-$(C_1-C_6)$alkyl-, Rb—O—Ra— where Rb is $(C_1-C_6)$alkyl and Ra is $(C_1-C_6)$alkyl, Rd-O—C(O)—O-Rc- where Rd is $(C_1-C_6)$alkyl or $(C_3-C_7)$cycloalkyl and Rc is $(C_1-C_6)$alkyl, or Rf—C(O)—O—Re— where Re is $(C_1-C_6)$alkyl and Rf is $(C_1-C_6)$alkyl.

23. The process according to claim 22, further comprising isolating the compound of formula (I).

* * * * *